(12) United States Patent
Mabjeesh

(10) Patent No.: US 8,785,373 B2
(45) Date of Patent: Jul. 22, 2014

(54) AGENTS CAPABLE OF DOWNREGULATING AN MSF-A-DEPENDENT HIF-1ALPHA AND USE THEREOF IN CANCER TREATMENT

(75) Inventor: Nicola J. Mabjeesh, Tel-Aviv (IL)

(73) Assignee: The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 0 days.

(21) Appl. No.: 13/366,390

(22) Filed: Feb. 6, 2012

(65) Prior Publication Data

US 2012/0128659 A1    May 24, 2012

Related U.S. Application Data

(62) Division of application No. 11/632,231, filed as application No. PCT/IL2005/000736 on Jul. 12, 2005.

(60) Provisional application No. 60/586,697, filed on Jul. 12, 2004.

(51) Int. Cl.
*A61P 13/08* (2006.01)
*A61K 38/17* (2006.01)
*C07K 14/47* (2006.01)

(52) U.S. Cl.
USPC .......................... 514/1.2; 514/19.5; 514/21.3

(58) Field of Classification Search
None
See application file for complete search history.

(56) References Cited

U.S. PATENT DOCUMENTS

| | | | |
|---|---|---|---|
| 5,849,556 A | 12/1998 | Hillman et al. | |
| 2003/0082758 A1* | 5/2003 | Rosen et al. | 435/183 |
| 2004/0072154 A1* | 4/2004 | Morris et al. | 435/6 |
| 2004/0259247 A1 | 12/2004 | Tuschl et al. | |
| 2009/0098127 A1 | 4/2009 | Mabjeesh | |

FOREIGN PATENT DOCUMENTS

| WO | WO 2004/074441 | 9/2004 |
|---|---|---|
| WO | WO 2006/038208 | 4/2006 |

OTHER PUBLICATIONS

Requisition Dated Feb. 19, 2013 From the Canadian Intellectual Property Office Re. Application No. 2,576,293.
Office Action Dated Sep. 9, 2012 From the Israel Patent Office Re. Application No. 180584 and Its Translation Into English.
Requisition Dated Feb. 8, 2012 From the Canadian Intellectual Property Office Re. Application No. 2,576,293.
Communication Under Rule 71(3) EPC Dated Feb. 8, 2013 From the European Patent Office Re.: Application No. 05759367.5.
Communication Pursuant to Article 94(3) EPC Dated Feb. 13, 2008 From the European Patent Office Re.: Application No. 05759367.5.
International Preliminary Report on Patentability Dated Apr. 12, 2007 From the International Bureau of WIPO Re.: Application No. PCT/IL2005/000736.
Invitation to Pay Additional Fees Dated Jun. 27, 2006 From the International Searching Authority Re.: Application No. PCT/IL05/00736.
Communication Pursuant to Article 94(3) EPC Dated Aug. 21, 2009 From the European Patent Office Re.: Application No. 05759367.5.
Communication Pursuant to Article 94(3) EPC Dated Nov. 30, 2010 From the European Patent Office Re.: Application No. 05759367.5.
International Search Report and the Written Opinion Dated Feb. 2, 2007 From the International Searching Authority Re.: Application No. PCT/IL05/00736.
Notice of Allowance Dated Oct. 19, 2011 From the US Patent and Trademark Office Re.: U.S. Appl. No. 11/632,231.
Notice of Non-Compliant Amendment Dated Sep. 9, 2011 From the US Patent and Trademark Office Re.: U.S. Appl. No. 11/632,231.
Office Action Dated Feb. 7, 2010 From the Israel Patent Office Re.: Application No. 180584 and Its Translation Into English.
Office Action Dated Jun. 20, 2011 From the Israel Patent Office Re.: Application No. 180584 and Its Translation Into English.
Official Action Dated Sep. 2, 2010 From the US Patent and Trademark Office Re.: U.S. Appl. No. 11/632,231.
Official Action Dated May 10, 2010 From the US Patent and Trademark Office Re.: U.S. Appl. No. 11/632,231.
Official Action Dated Jul. 23, 2009 From the US Patent and Trademark Office Re.: U.S. Appl. No. 11/632,231.
Official Action Dated Dec. 31, 2009 From the US Patent and Trademark Office Re.: U.S. Appl. No. 11/632,231.
Response Dated Dec. 1, 2010 to Official Action of Sep. 2, 2010 From the US Patent and Trademark Office Re.: U.S. Appl. No. 11/632,231.
Response Dated Jun. 7, 2010 to Office Action of Feb. 7, 2010 From the Israel Patent Office Re.: Application No. 180584.
Response Dated Aug. 10, 2010 to Official Action of May 10, 2010 From the US Patent and Trademark Office Re.: U.S. Appl. No. 11/632,231.
Response Dated Sep. 13, 2011 to the Interview With the Examiner of Sep. 8, 2011 From the US Patent and Trademark Office Re.: U.S Appl. No. 11/632,231.
Response Dated Dec. 15, 2009 to Communication Pursuant to Article 94(3) EPC of Aug. 21, 2009 From the european Patent Office Re.: Application No. 05759367.5.
Response Dated Mar. 22, 2010 to Official Action of Dec. 31, 2009 From the US Patent and Trademark Office Re.: U.S. Appl. No. 11/632,231.
Response Dated Oct. 23, 2011 to Office Action of Jun. 20, 2011 From the Israel Patent Office Re.: Application No. 180584.

(Continued)

*Primary Examiner* — Maury Audet
*Assistant Examiner* — Joseph Fischer

(57) ABSTRACT

Methods and pharmaceutical compositions for the treatment of cancer or acute ischemia are provided. Also provided are methods of identifying agents capable of preventing the formation of or dissociating the MSF-A-HIF-1alpha protein complex, and methods of determining the prognosis of an individual having cancer by identifying the presence or absence of such a protein complex.

3 Claims, 45 Drawing Sheets
(11 of 45 Drawing Sheet(s) Filed in Color)

(56) References Cited

OTHER PUBLICATIONS

Response Dated Mar. 27, 2011 to Communication Pursuant to Article 94(3) EPC of Nov. 30, 2010 From the European Patent Office Re.: Application No. 05759367.5.

Supplementary European Search Report and the European Search Opinion Dated Oct. 1, 2007 From the European Patent Office Re.: Application No. 05759367.5.

Amir et al. "MSF-A Interacts With Hypoxia-Inducible Factor-1α and Augments Hypoxia-Inducible Factor Transcriptional Activation to Affect Tumorigenicity and Angiogenesis", Cancer Research, 66(2): 856-866, 2006. p. 856-866.

Graat et al. "Enhanced Tumor Cell Kill by Combined Treatment With a Small-Molecule Antagonist of Mouse Double Minute 2 and Adenoviruses Encoding P53", Molecular Cancer Therapy, 6(5): 1552-1561, May 2007.

Kalikin et al. "Genomic and Expression Analyses of Alternatively Spliced Transcripts of the MLL Septin-Like Fusion Gene (MSF) That Map to a 17q25 Region of Loss in Breast and Ovarian Tumors", Genomics, 63: 165-172, 2000.

Lee et al. "Inhibition of Hypoxia-Induced Angiogenesis by FK228, A Specific Histone Deacetylase Inhibitor, Via Suppression of HIF-1? Activity", Biochemical and Biophysical Research Communications, 300: 241-246, 2003.

Montagna et al. "The Septin 9 (NSF) Gene Is Amplified and Overexpressed in Mouse Mammary Gland Adenocarcinomas and Human Breast Cancer Cell Lines", Cancer Research, 63: 2179-2187, May 1, 2003.

Nagata et al. "Filament Formation of MSF-A, A Mammalian Septin, in Human Mammary Epithelial Cells Depends on Interactions With Microtubules", The Journal of Biological Chemistry, 278(20): 18538-18543, 2003.

Nagata et al. "Filament Formation of MSF-A, A Mammalian Septin, in Mammary HMEC Cells Depends on Interactions With Microtubules", Molecular Biology of the Cell, 13(Suppl.): 189a/No. 1061, 2002. & 42nd Annual Meetin of the American Society for Cell Biology, San Francisco, CA, USA, 2002. Abstract.

Nagata et al. "The High Level of hCDC10 Gene Expression in Neuroblastoma May Be Associated With Favorable Characteristics of the Tumor", The Journal of Surgical Research, 92(2): 267-275, Aug. 2000. Abstract.

Russell et al. "Isolation and Mapping of a Human Septin Gene to a Region on Chromosome 17q, Commonly Deleted in Sporadic Epithelial Ovarian Tumors", Cancer Research, 6007): 4729-4734, 2000. p. 4729, r-h Col., Lines 27-34, p. 4731, r-h Col., § 3, p. 4734, 1-h Col., § 2, Fig.3.

Schindl et al. "Overexpression of Hypoxia-Inducible Factor 1Alpha Is Associated With an Unfavorable Prognosis in Lymph Node-Positive Breast Cancer", Clinical Cancer Research, 8: 1831-1837, 2002.

Surka et al. "The Mammalian Septin MSF Localizes With Microtubules and Is Required for Completion of Cytokinesis", Molecular Biology of the Cell, 13: 3532-3545, 2002. p. 3533, r-h Col., § 3, p. 3534, r-h Col., § 4—p. 3535, 1-h Col., § 1, p. 3538, r-h Col., § 2—p. 3541, r-h Col., Line 2, p. 3543, r-h Col., § 2.

Communication Pursuant to Article 94(3) EPC Dated Jun. 11, 2012 From the European Patent Office Re.: Application No. 05759367.5.

Communication Under Rule 71(3) EPC Dated Sep. 11, 2013 From the European Patent Office Re. Application No. 05759367.5.

Requisition by the Examiner Dated Jan. 15, 2014 From the Canadian Intellectual Property Office Re. Application No. 2,576,293.

* cited by examiner

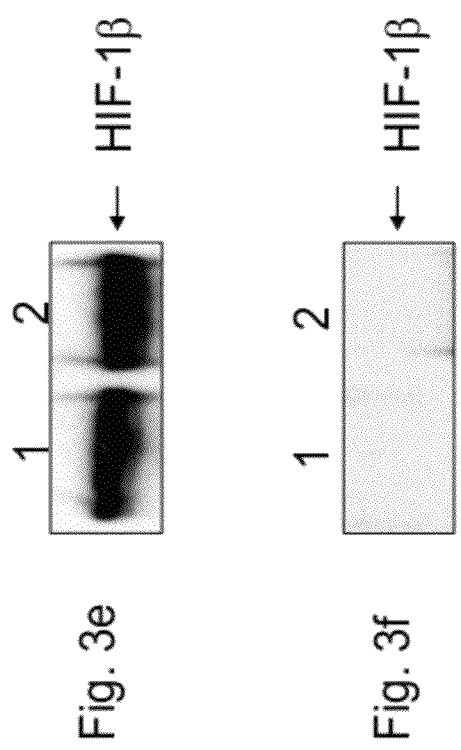

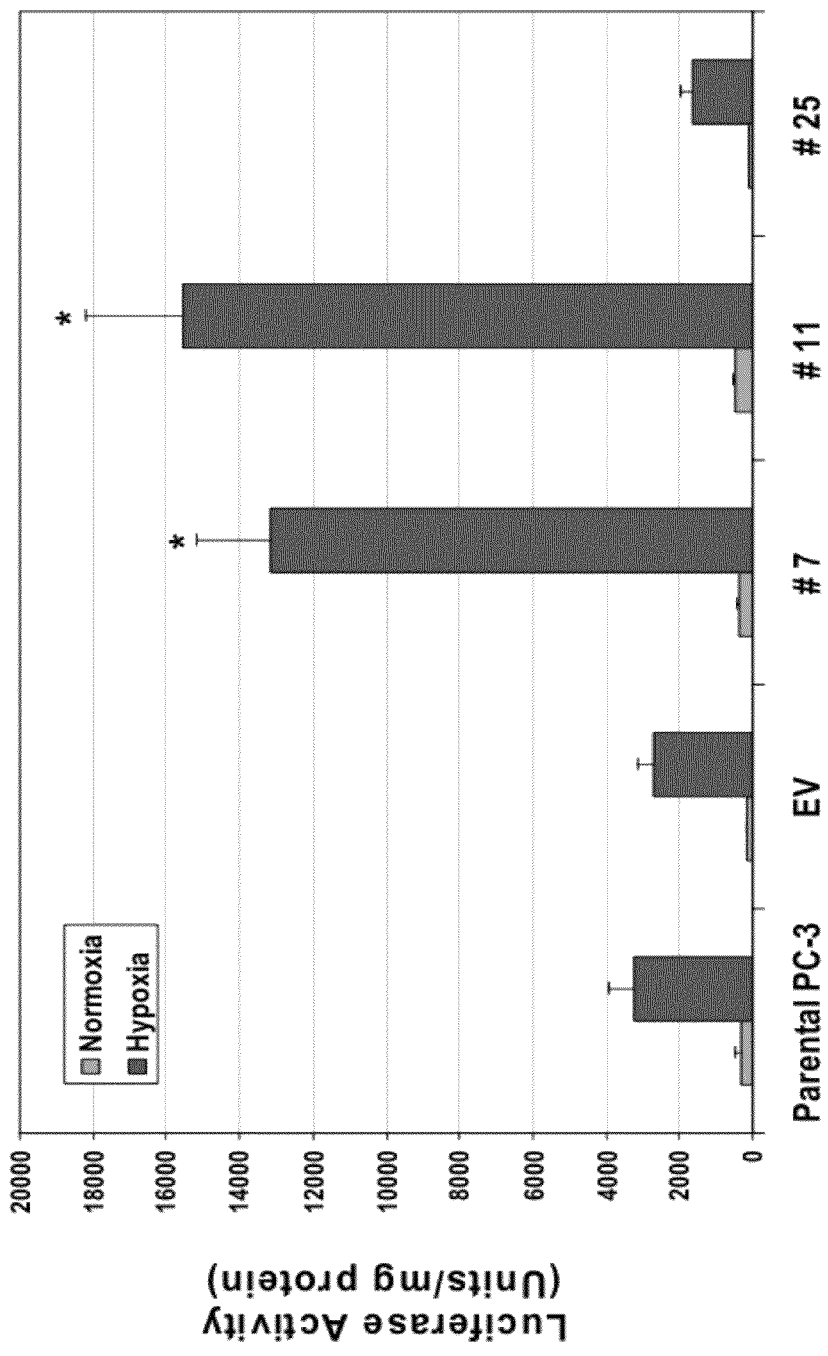

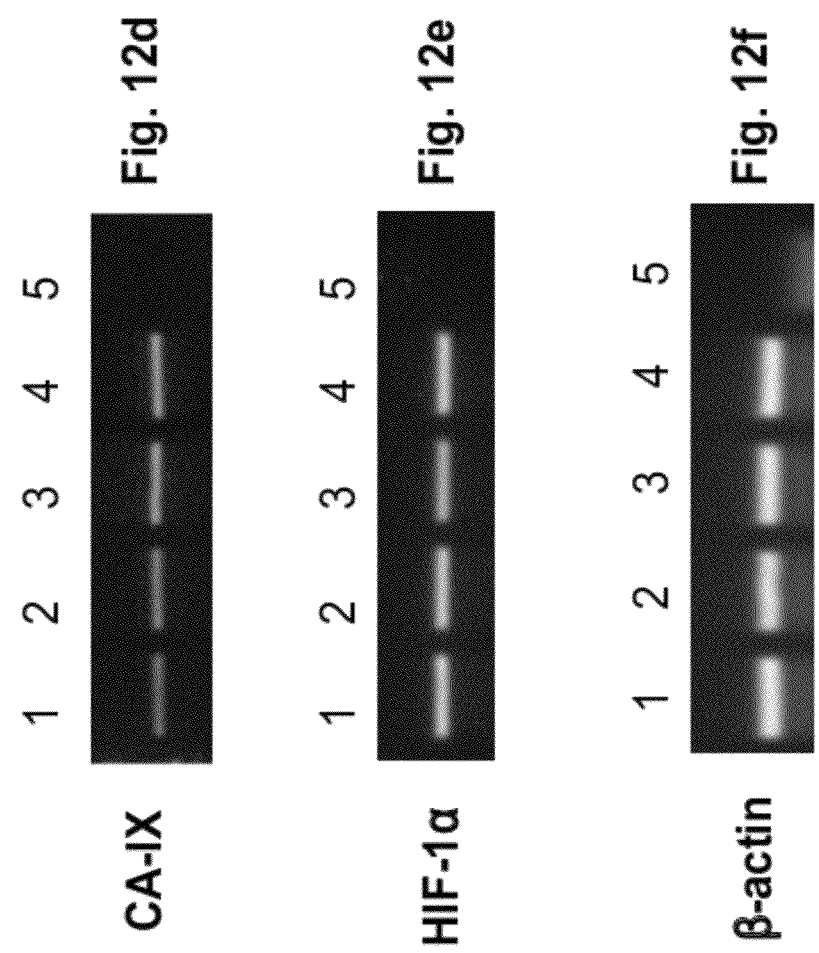

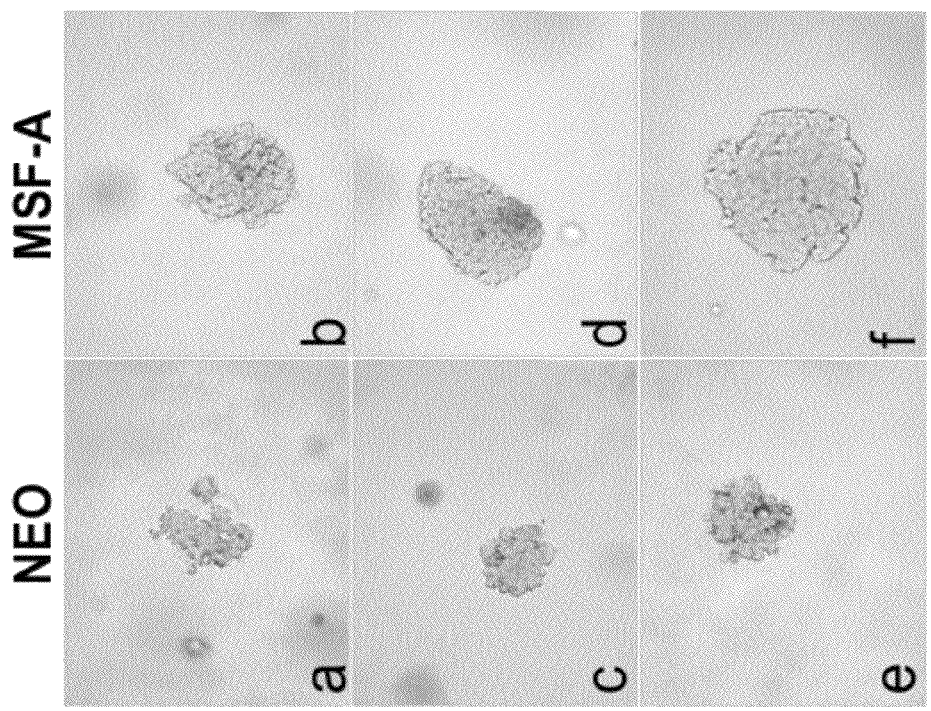
Figs. 14a-f

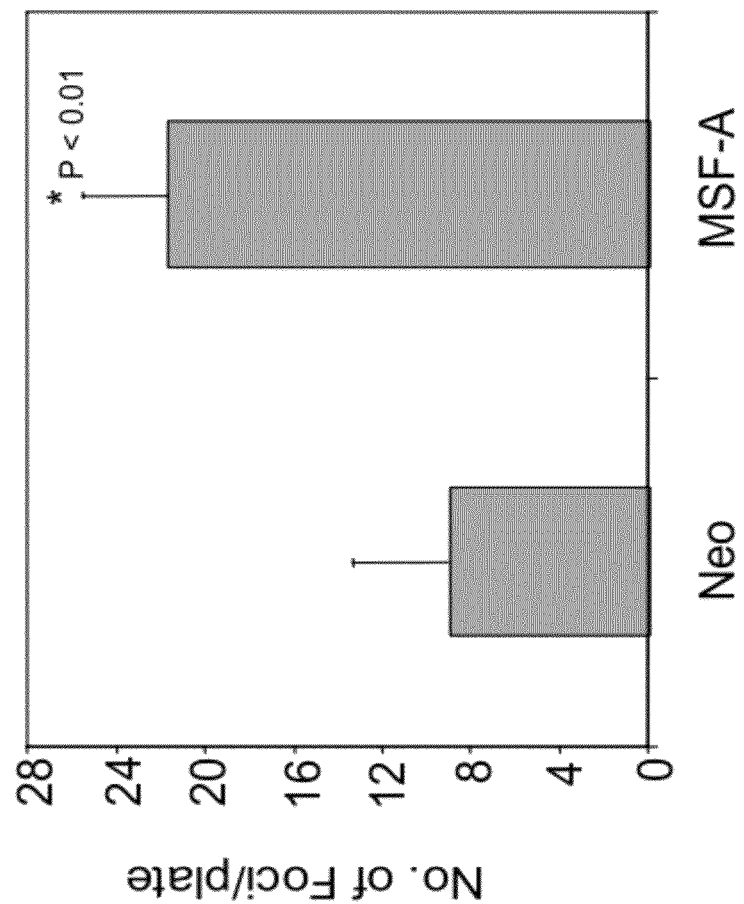

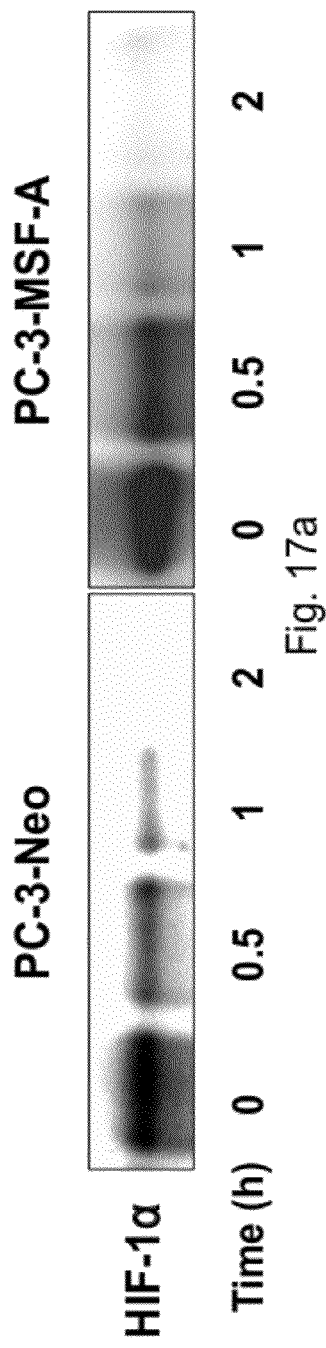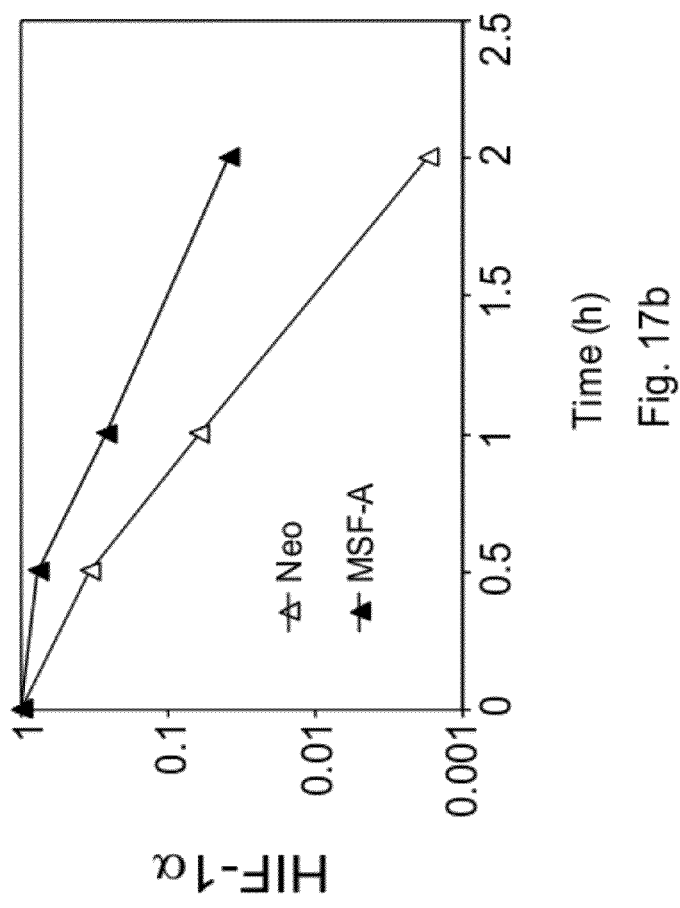
Fig. 17a
Fig. 17b

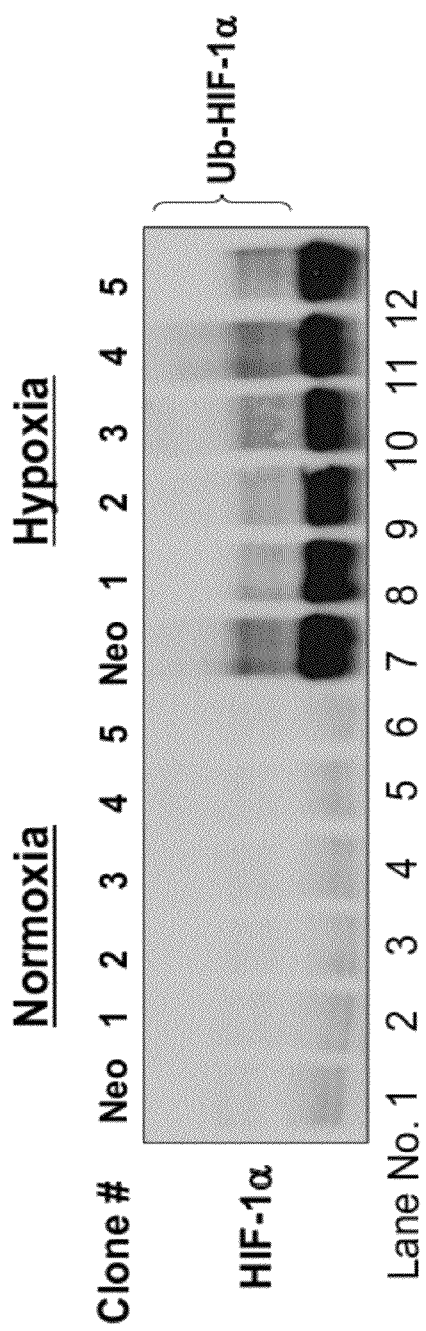
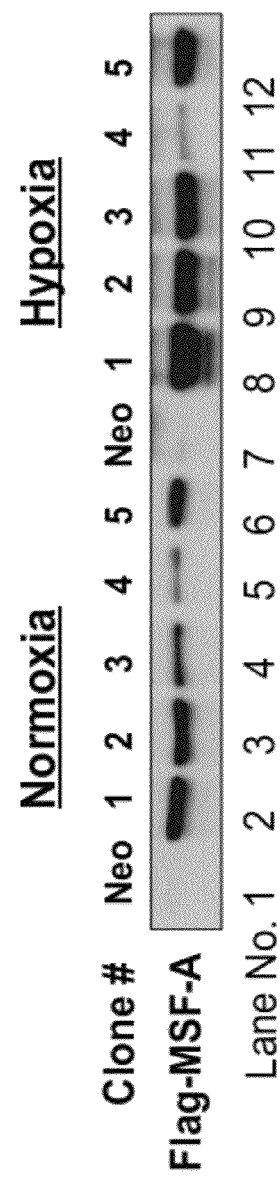
Fig. 18a
Fig. 18b

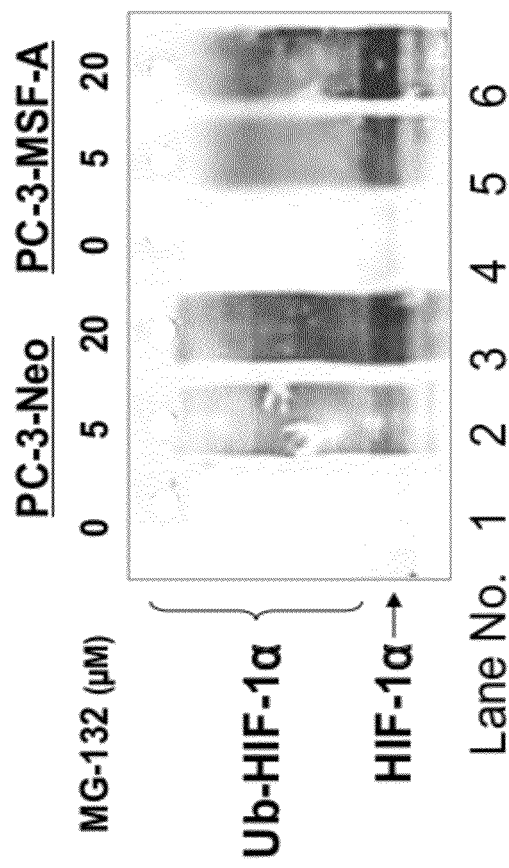
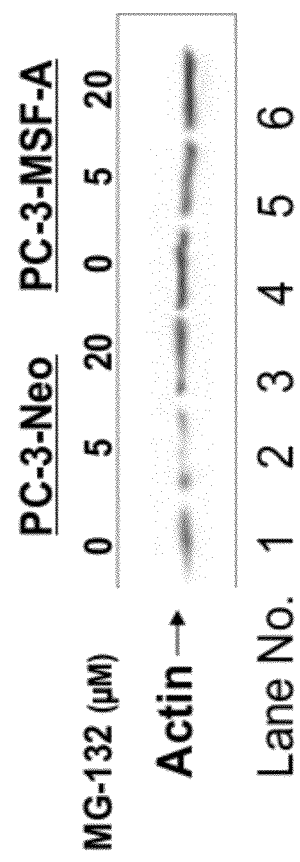

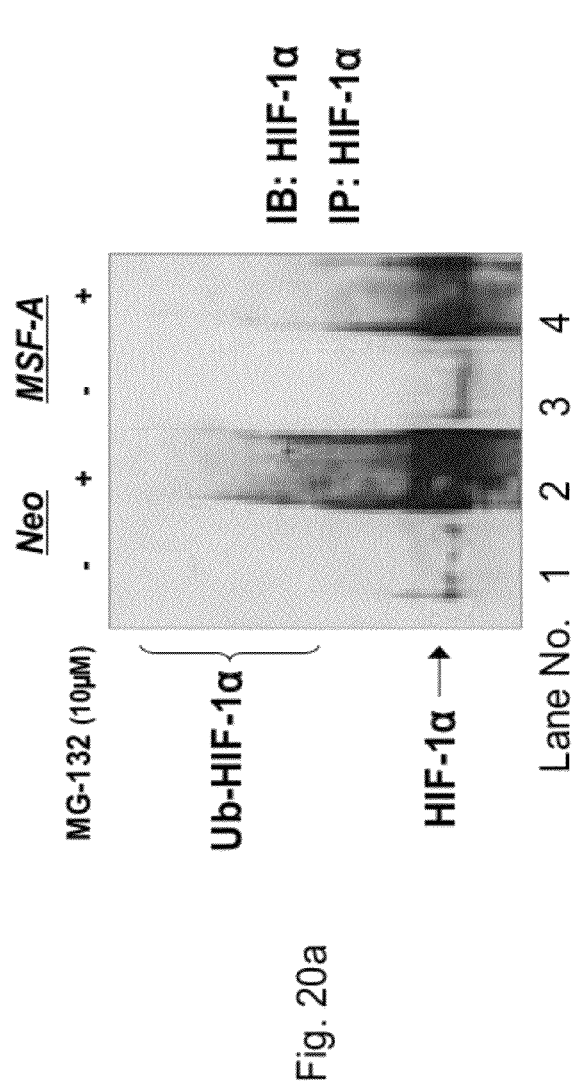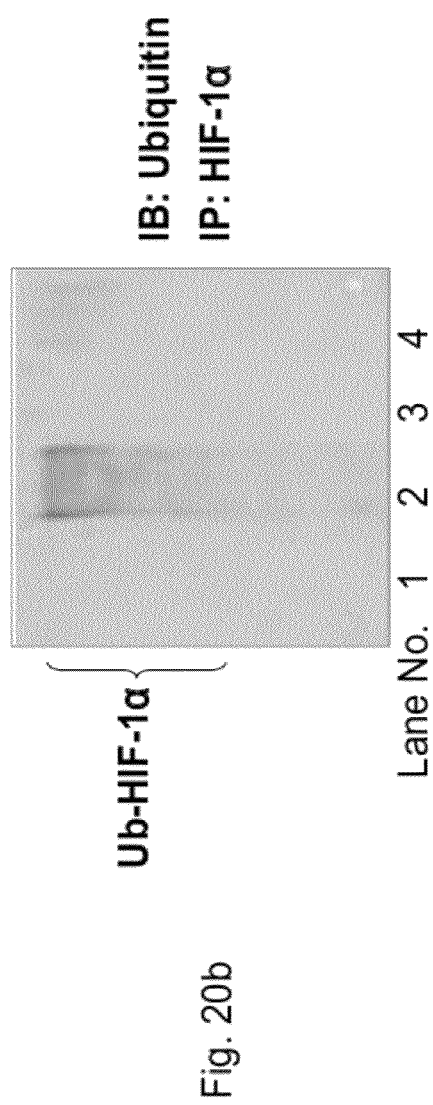
Fig. 20a
Fig. 20b

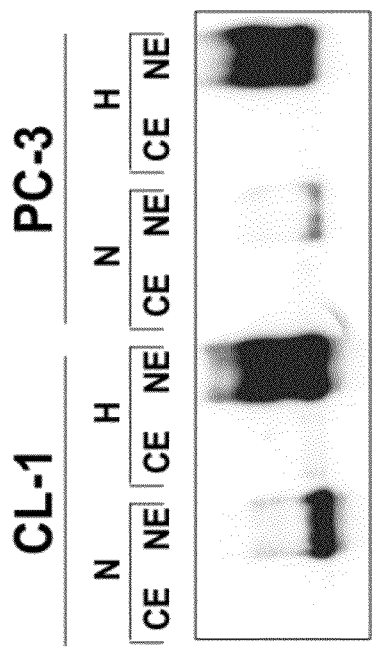
Fig. 23a  HIF-1α
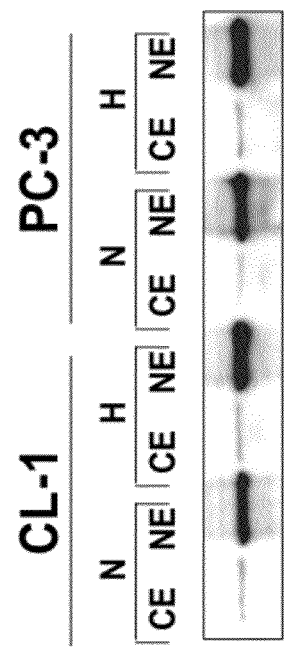
Fig. 23b  MSF-A
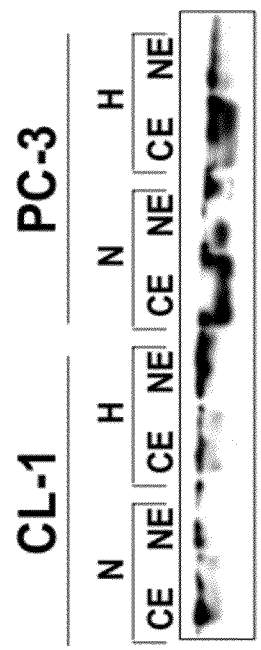
Fig. 23c  α-tubulin

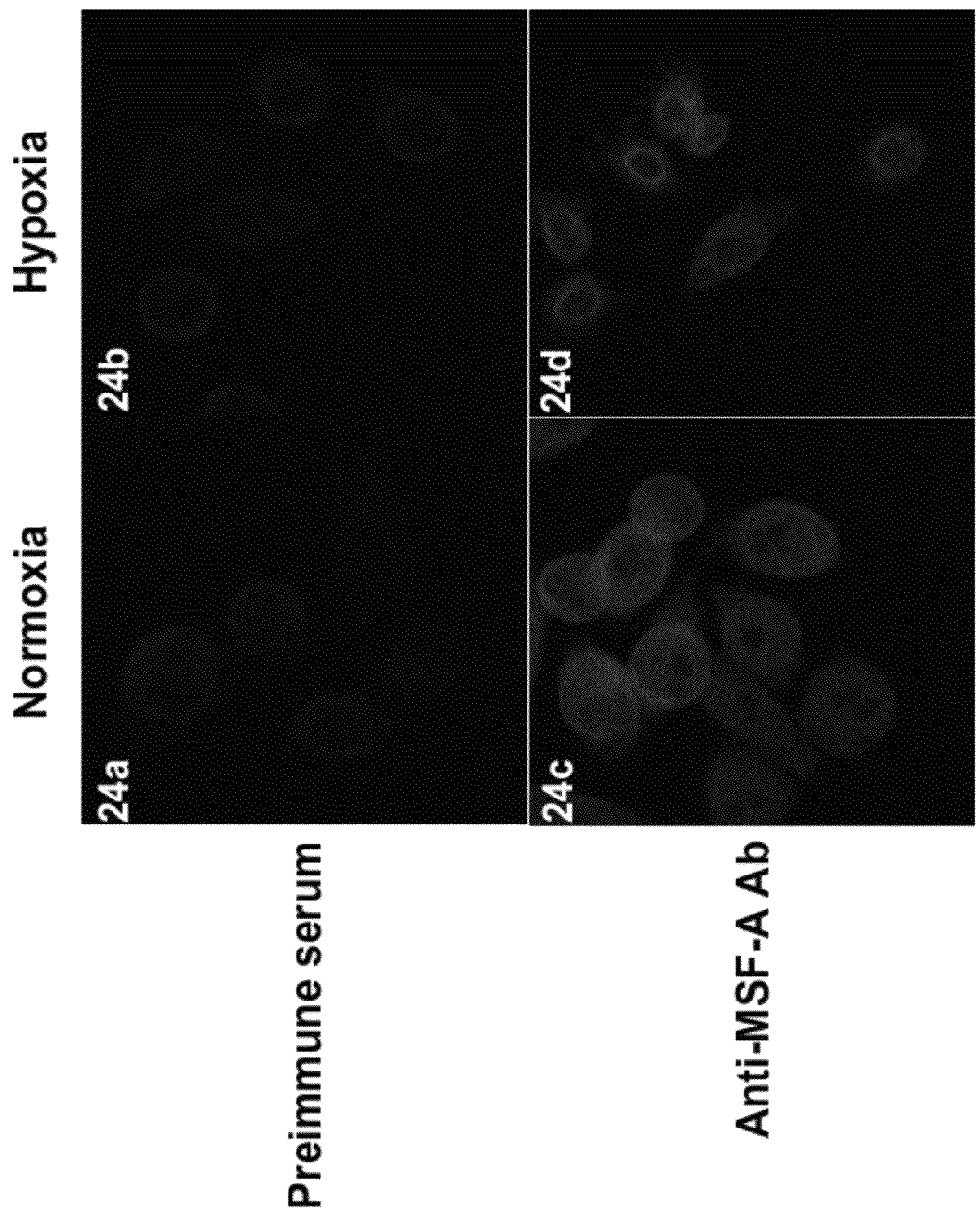
Figs. 24a-d

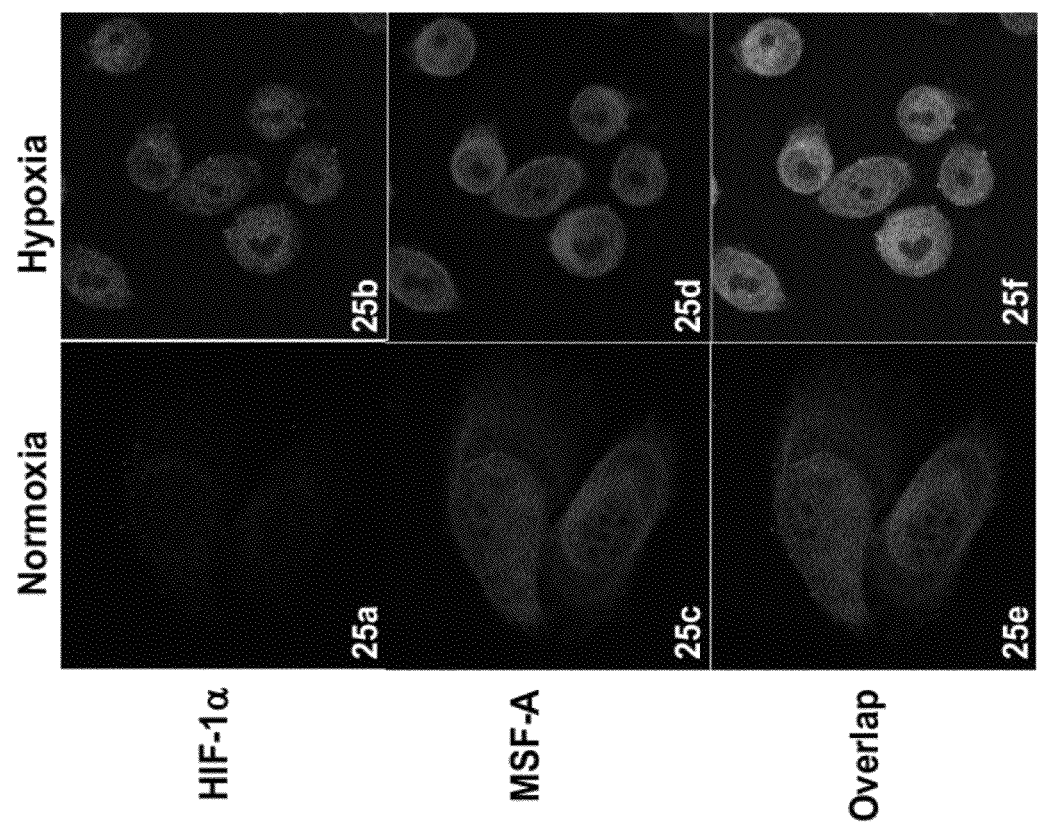
Figs. 25a-f

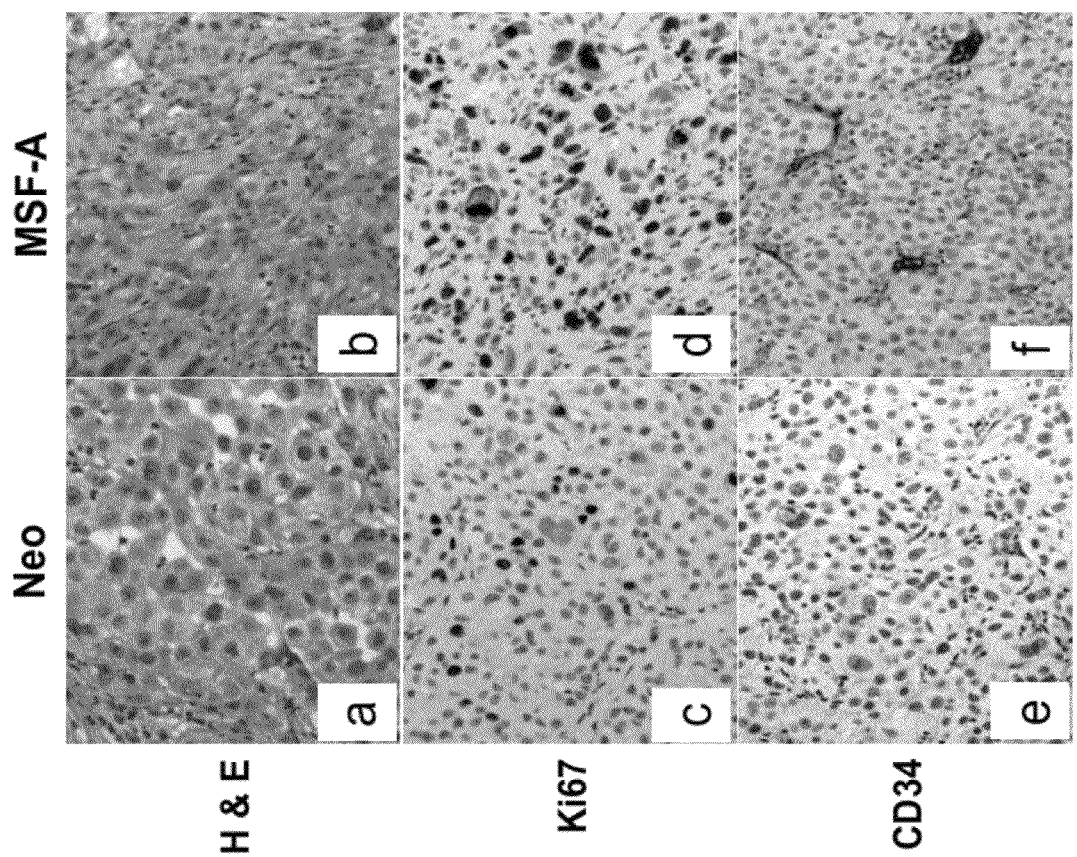
Figs. 30a-f

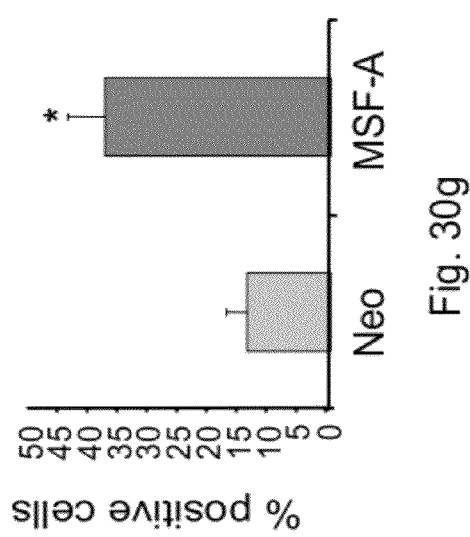
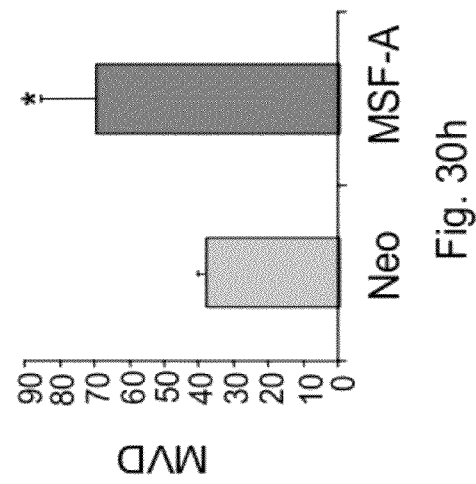

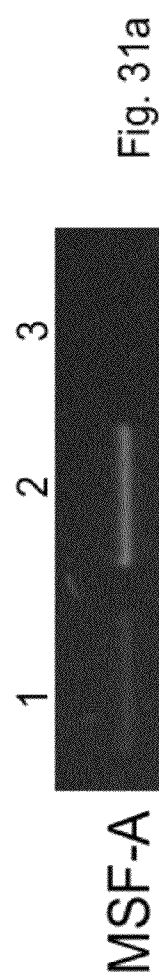
Fig. 31a MSF-A
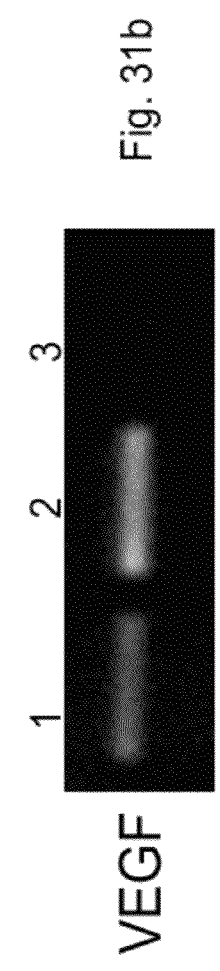
Fig. 31b VEGF
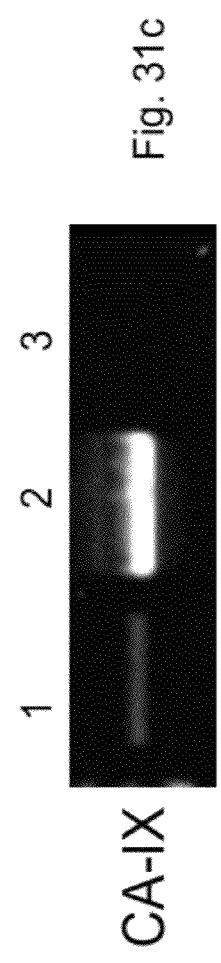
Fig. 31c CA-IX

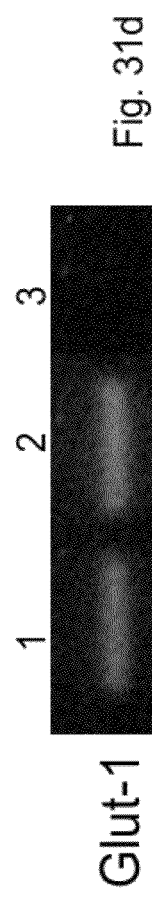
Fig. 31d Glut-1
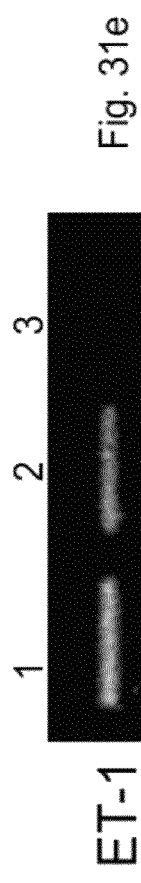
Fig. 31e ET-1
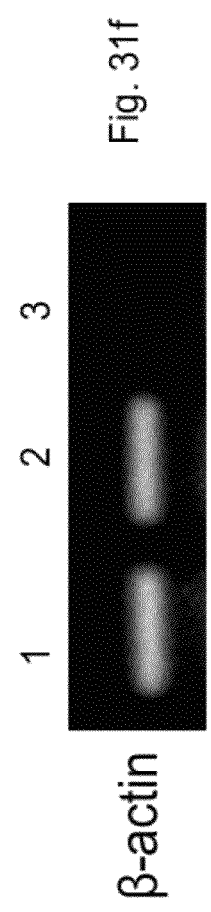
Fig. 31f β-actin

AGENTS CAPABLE OF DOWNREGULATING AN MSF-A-DEPENDENT HIF-1ALPHA AND USE THEREOF IN CANCER TREATMENT

RELATED APPLICATIONS

This application is a divisional of U.S. patent application Ser. No. 11/632,231 filed on Jan. 11, 2007 which is a National Phase of PCT Patent Application No. PCT/IL2005/000736 having International Filing Date of Jul. 12, 2005, which claims the benefit of priority of U.S. Provisional Patent Application No. 60/586,697 filed on Jul. 12, 2004. The contents of the above applications are all incorporated herein by reference.

FIELD AND BACKGROUND OF THE INVENTION

The present invention relates to agents which can prevent the formation of, or dissociate or destabilize an MSF-A-HIF1α protein complex and, more particularly, to the use of such agents in treating cancer.

Hypoxia-inducible factors (HIFs) are transcription factors involved in the transcription activation of several genes including, angiogenic factors (e.g., VEGF and FLT1), glucose transporters (Glut-1 and Glut-3), and glycolytic enzymes which are involved in the production of ATP in the absence of $O_2$ (for overview see Semenza G L. 2003; Nat. Rev. Cancer 3: 721-732; Paul S A, Simons J W, Mabjeesh N J. 2004; J. Cell Physiol. 200: 20-30). HIF transcription factors are composed of two subunits, HIF-α and HIF-β. While the HIF-β is constitutively expressed, the expression of HIF-α is regulated by the level of oxygen. Thus, in the presence of normal oxygen tension (i.e., normoxia), HIF-1α is hydroxylated at the two critical proline residues (402 and 564 of GenBank Accession No. NP_001521) by members of the prolyl hydroxylase protein (PHD) family (PHD-1, -2, and -3). Hydroxylated-HIF-1α can then bind the von Hippel-Lindau (VHL) tumor suppressor protein, which recruits the E3 ubiquitin-ligase complex to targeting the HIF-α protein to proteasomal degradation. However, since oxygen is the rate-limiting co-factor of PHD enzymes, at low oxygen tension (i.e., hypoxia conditions), the prolyl hydroxylases are unable to hydroxylate HIF-α. As a result, no VHL interaction occurs and the E3 ubiquitin-ligase complex is unable to target HIF-1α to proteasomal degradation, resulting in stabilization of HIF. Stabilized HIF-1α can then form a heterodimer with the HIF-1β, which interacts with the basic helix-loop-helix domain of the hypoxia response element (HRE) in target genes.

In addition, hydroxylation of an asparagine residue in the C-terminal transactivation domain (TAD) of HIF-α (at position 803) by the factor inhibiting HIF-1 (FIH-1) negatively regulates transcriptional activity of HIF by preventing its interaction with p300 and CBP transactivators.

Elevated levels of HIF-1α protein are found in the majority of solid tumors and cancer metastases in the areas of profound hypoxia (Quintero M, Mackenzie N, Brennan P A. 2004; Eur. J. Surg. Oncol. 30: 465-8). In addition, a number of oncogenes such as AKT, Src, and oncogenic Ras were found to induce HIF expression (Li J, et al., 2004; Cancer Res. 64: 94-101). Moreover, p53 and Hsp90 were found to positively and negatively regulate HIF-1α degradation, respectively, i.e., while under normoxia P53 promotes HIF-1α degradation (Choi K S et al., 2003; J. Biochem. Mol. Biol. 36: 120-7), Hsp90 has a protective role in VHL-independent degradation of HIF-1α (Isaacs J S et al., J. Biol. Chem. 2004; 279: 16128-35). In addition, in many cases, the major reason for the failure of cancer therapy is the resistance of hypoxic cancer cells to both chemotherapy and radiation (Escuin D et al., 2004; Cancer Biol Ther. 3(7). Epub ahead of print). Thus, HIF-1α has been recognized as a possible target for anti cancer therapy (Welsh S J and Powis G. 2003; Curr Cancer Drug Targets. 3(6): 391-405; Macpherson G R and Figg W D, 2004; Cancer Biol. Ther. 3(6). Epub ahead of print).

Several agents capable of downregulating HIF-1 have been identified as potential anti-cancer agents including FK228, a histone deacetylase (HDAC) inhibitor (Mie Lee Y et al., 2003. Biochem. Biophys. Res. Commun 300: 241-6), PX-478, a small-molecule HIF-1 inhibitor, (Macpherson G R, Figg W D. 2004. Cancer Biol. Ther. 3(6) Epub ahead of print) and Bisphenol A, an environmental endocrine-disrupting chemical (Kubo T et al., 2004; Biochem. Biophys. Res. Commun 318(4): 1006-11). However, although desired, the mechanisms leading to up- or down-regulation of HIFs in cancerous tumors are not yet clear, thus, limiting the use of HIF-1 inhibitors/suppressors as anti cancer agents.

While reducing the present invention to practice, the present inventor has uncovered that MSF-A, a myeloid/lymphoid leukemia septin-like fusion protein A, regulates HIF-1α activity and thus contributing to cancer progression.

SUMMARY OF THE INVENTION

According to one aspect of the present invention there is provided a method of treating cancer and/or inhibiting a growth of a cancerous tumor and/or metastases in an individual comprising providing to the individual an agent capable of downregulating an MSF-A-dependent HIF-1α activity in cells of the individual thereby treating the cancer and/or inhibiting the growth of the cancerous tumor and/or the metastases in the individual.

According to another aspect of the present invention there is provided an antibody or antibody fragment capable of specifically binding to an MSF-A polypeptide.

According to yet another aspect of the present invention there is provided a method of treating acute ischemia in cells of an individual comprising providing to the individual an agent capable of increasing an MSF-A-dependent HIF-1α activity in cells of the individual to thereby treat the acute ischemia.

According to still another aspect of the present invention there is provided a method of identifying putative anti cancer agents, the method comprising identifying agents being capable of preventing the formation of and/or dissociating an MSF-A-HIF-1α protein complex, thereby identifying the putative anti cancer agents.

According to an additional aspect of the present invention there is provided a method of determining if a molecule is capable of preventing the formation of and/or dissociating an MSF-A-HIF-1α protein complex, comprising incubating the MSF-A-HIF-1α protein complex or cells harboring the MSF-A-HIF-1α protein complex with the molecule and determining the presence or absence of the MSF-A-HIF-1α protein complex following the incubating, wherein the absence of the MSF-A-HIF-1α protein complex is indicative of the capacity of the molecule to prevent the formation of and/or dissociate the MSF-A-HIF-1α protein complex.

According to yet an additional aspect of the present invention there is provided a method of determining the prognosis of an individual having cancer, comprising determining the presence or absence of an MSF-A-HIF-1α protein complex in cancerous cells derived from the individual, wherein the presence of the MSF-A-HIF-1α protein complex is indicative of poor prognosis of the individual.

According to further features in preferred embodiments of the invention described below, downregulating the MSF-A-dependent HIF-1α activity is effected by preventing a formation of an MSF-A-HIF-1α complex and/or dissociating the MSF-A-HIF-1α complex.

According to still further features in the described preferred embodiments the agent capable of preventing formation of the MSF-A-HIF-1α complex is capable of downregulating and/or preventing an association between MSF-A and HIF-1α.

According to still further features in the described preferred embodiments the agent capable of preventing the formation of and/or dissociating the MSF-A-HIF-1α protein complex is selected from the group consisting of an MSF-A antisense oligonucleotide, an MSF-A siRNA, an MSF-A DNAzyme, an MSF-A Ribozyme, an MSF-A antibody or antibody fragment, a non-functional MSF-A polypeptide, an MSF-A derived peptide or peptide analog, a non-functional HIF-1α polypeptide and an HIF-1α derived peptide or peptide analog.

According to still further features in the described preferred embodiments the MSF-A antibody or antibody fragment is capable of specifically binding to the polypeptide set forth by SEQ ID NO:3.

According to still further features in the described preferred embodiments the non-functional MSF-A polypeptide is set forth by SEQ ID NO:10.

According to still further features in the described preferred embodiments the MSF-A derived peptide or peptide analog includes the amino acid sequence set forth in SEQ ID NOs:2463-4193 or 4213.

According to still further features in the described preferred embodiments the HIF-1α derived peptide or peptide analog includes the amino acid sequence set forth in SEQ ID NOs:12-2462.

According to still further features in the described preferred embodiments the cancer and/or the cancerous tumor is selected from the group consisting of prostate cancer, breast cancer, chemotherapy-induced MLL, stomach cancer, cervical cancer, endometrial cancer, and ovarian cancer.

According to still further features in the described preferred embodiments the antibody is capable of preventing the formation of and/or dissociating an MSF-A-HIF-1α protein complex.

According to still further features in the described preferred embodiments the acute ischemia is a result of stroke and/or acute myocardium infraction. According to still further features in the described preferred embodiments increasing the MSF-A-dependent HIF-1α activity is effected by upregulating formation of an MSF-A-HIF-1α protein complex and/or stabilizing the MSF-A-HIF-1α protein complex.

According to still further features in the described preferred embodiments the agent capable of upregulating the MSF-A-HIF-1α protein complex is capable of increasing the association between MSF-A and HIF-1α.

According to still further features in the described preferred embodiments the agent capable of upregulating and/or stabilizing the MSF-A-HIF-1α protein complex is selected from the group consisting of an exogenous polynucleotide encoding at least a functional portion of MSF-A, an exogenous polynucleotide encoding at least a functional portion of HIF-1α, an exogenous polypeptide including at least a functional portion of MSF-A, an exogenous polypeptide including at least a functional portion of HIF-1α, a polypeptide capable of stabilizing the MSF-A-HIF1α protein complex.

According to still further features in the described preferred embodiments the agents are selected from the group consisting of chemicals, antibodies, aptamers, peptides, and peptide analogs.

According to still further features in the described preferred embodiments the peptide or peptide analog is derived from MSF-A or HIF-1α. According to still further features in the described preferred embodiments the peptide or peptide analog includes the amino acid sequence set forth in SEQ ID NOs: 2463-4193, 4213 or 12-2462.

According to still further features in the described preferred embodiments incubating is effected for a time period selected from the range of 1-48 hours.

According to still further features in the described preferred embodiments the presence or the absence of the MSF-A-HIF-1α protein complex is effected using anti-MSF-A and/or anti-HIF-1α antibody.

According to still further features in the described preferred embodiments determining the presence or the absence of the MSF-A-HIF-1α protein complex is effected by sequentially and/or simultaneously exposing the MSF-A-HIF-1α protein complex or the cells harboring the MSF-A-HIF-1α protein complex to the anti-MSF-A and the anti-HIF-1α antibodies.

According to still further features in the described preferred embodiments determining the presence or the absence of the MSF-A-HIF-1α protein complex is effected using an immunological detection method.

According to still further features in the described preferred embodiments the immunological detection method utilizes an anti-MSF-A and/or an anti-HIF-1α antibody or antibody fragment.

The present invention successfully addresses the shortcomings of the presently known configurations by providing methods of treating cancer or acute ischemia.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is an autoradiogram illustrating HIF-1α-immunoprecipitation from whole cell lysates of $^{35}$S-metabolically labeled PC-3 cells.

FIG. 2 is a Western Blot analysis illustrating the expression of recombinant MSF-A protein in HEK 293 transfected cells. HEK 293 cells were transiently transfected with the p3xFlag-MSF-A vector and the expression of the recombinant MSF-A protein was detected at the indicated time points using an anti-Flag antibody (Sigma-Aldrich Corp., St Louis, Mo., USA).

Figure 3A:
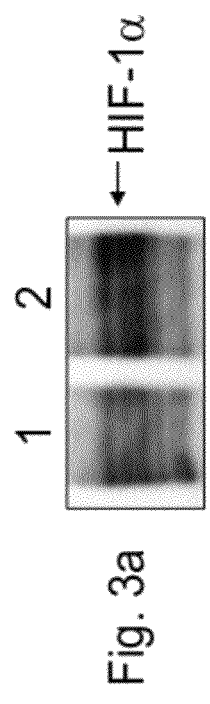
Figure 3B:
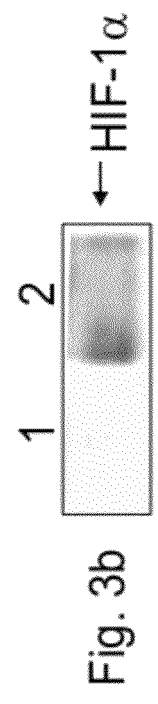
Figure 3C:
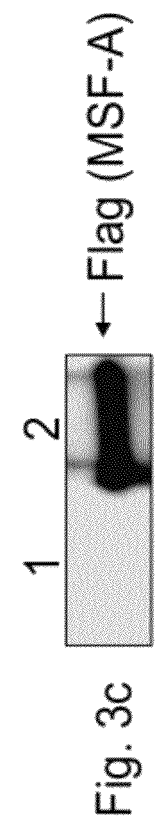
Figure 3D:
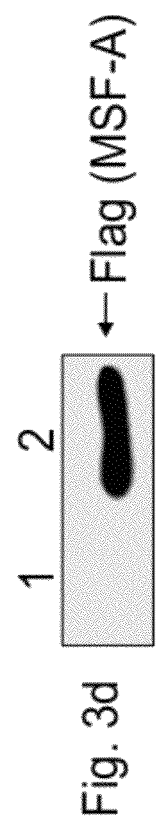

FIGS. 3a-f are autoradiograms illustrating HIF-1α immunoblotting of FLAG immunoprecipitates (IP) (FIG. 3b) or whole cell extracts (WCE) (FIG. 3a), FLAG immunoblotting of HIF-1α IP (FIG. 3d) or WCE (FIG. 3c), and HIF-1β immunoblotting of FLAG IP (FIG. 3f) or WCE (FIG. 3e). HEK 293 cells were transiently co-transfected with two of the following expression vectors: p3xFlag-cmv-25 (EV), pcdna3.1-HIF-1α (HIF-1α) or p3xFlag-MSF-A (MSF-A), and two days following transfection under normoxic conditions WCE or IP were subjected to immunoblot (IB) analysis. Lane 1-EV and HIF-1α; lane 2-MSF-A and HIF-1α.

Figure 4A:
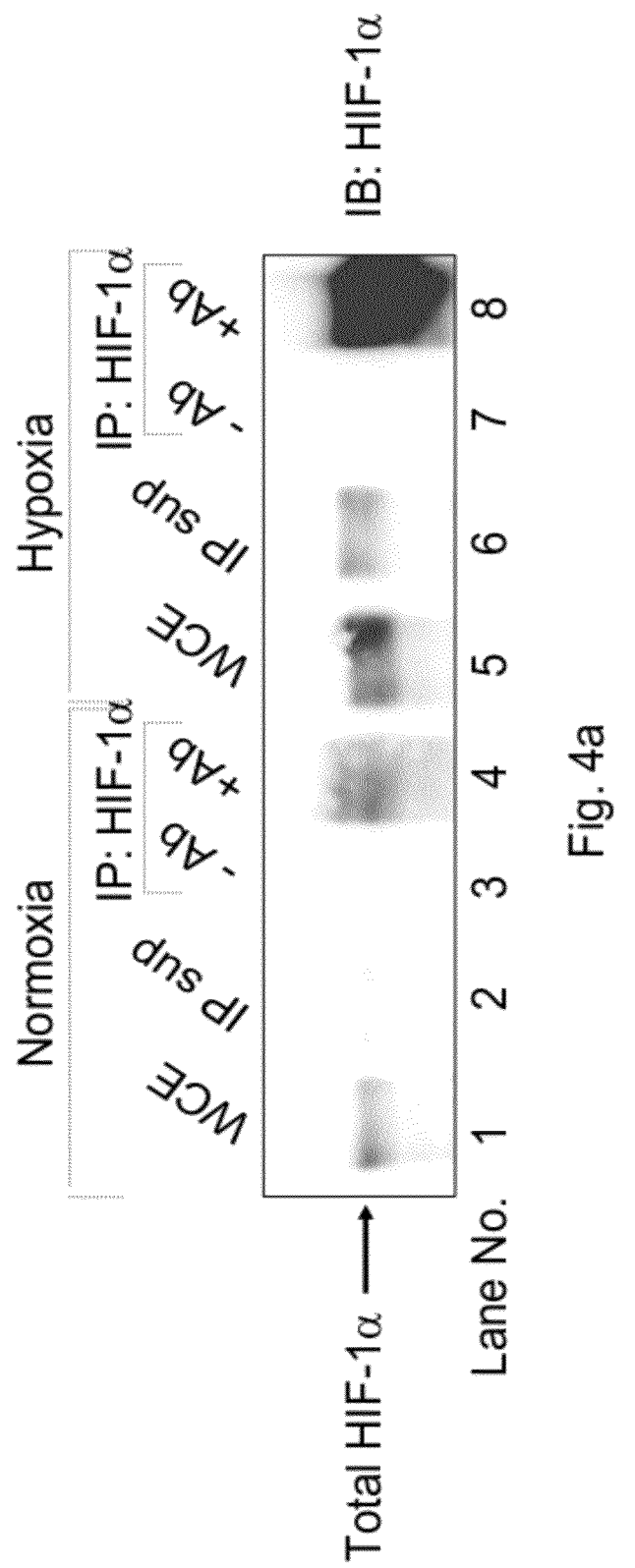
Figure 4B:
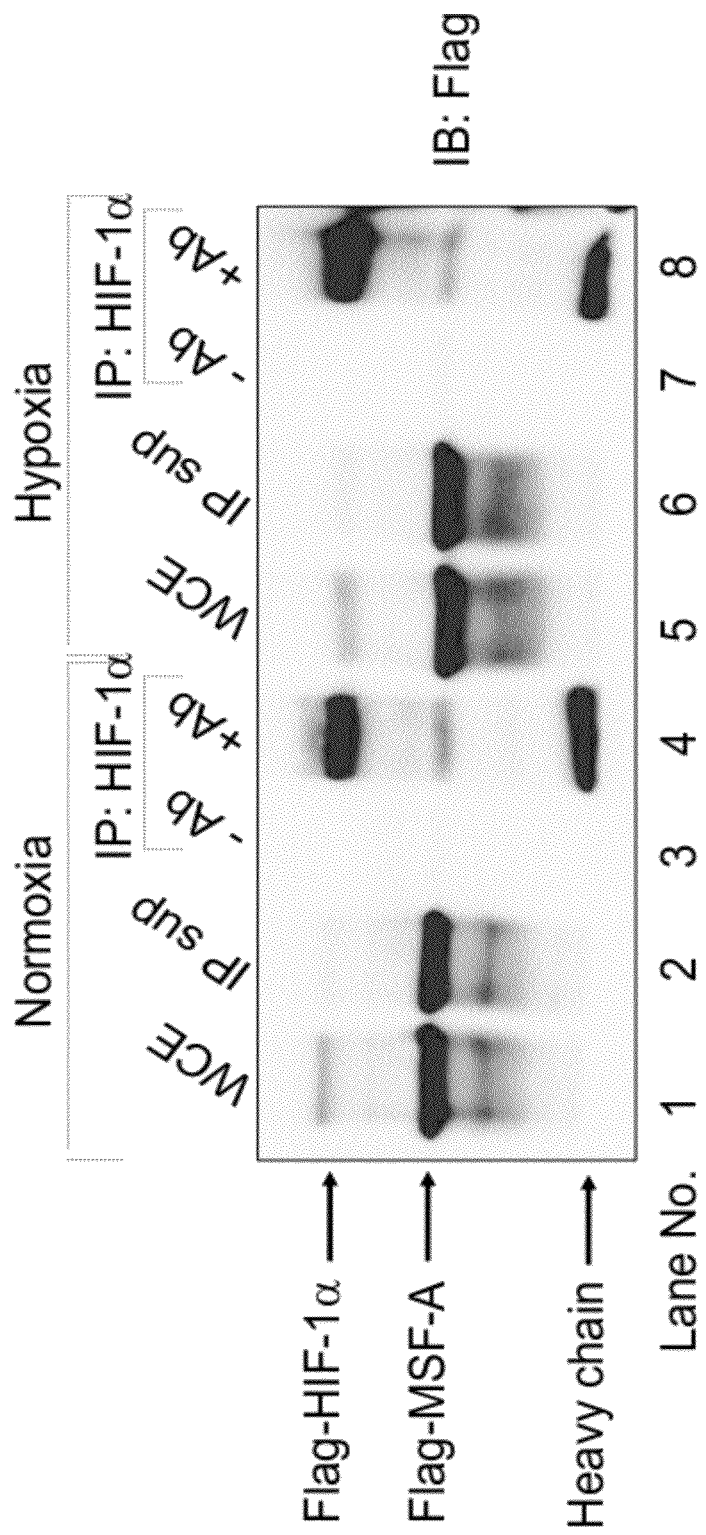

FIGS. 4a-b are autoradiograms depicting HIF-1α (FIG. 4a) or Flag (FIG. 4b) immunoblotting of HIF-1α immunoprecipitates. HEK 293 cells were co-transfected with the p3xFlag-HIF-1α and p3xFlag-MSF-A vectors and 24 hours following transfection the cell were subjected to either normoxia (lanes 1-4) or hypoxia (lanes 5-8) for another 24 hours. Lanes 1 and 5=WCE, lanes 2 and 6=IP sup, lanes 3 and 7=HIF-1α IP without an antibody (negative control), lanes 4 and 8=HIF-1α IP; WCE=whole cell extracts; IP sup=immunoprecipitation supernatant; Ab=antibody.

Figure 5A:
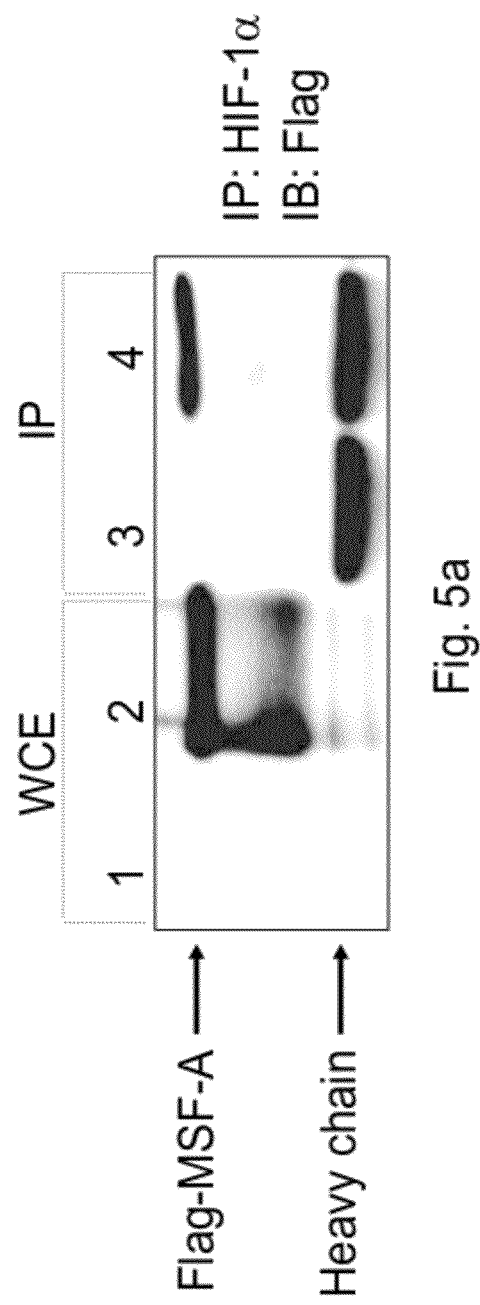
Figure 5B:
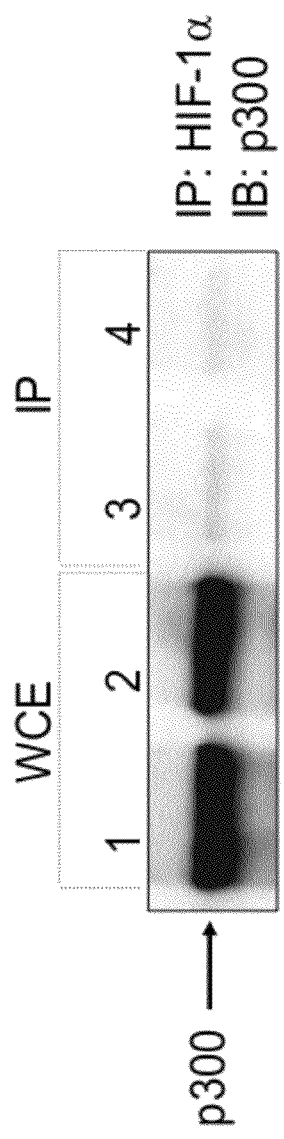
Figure 5C:
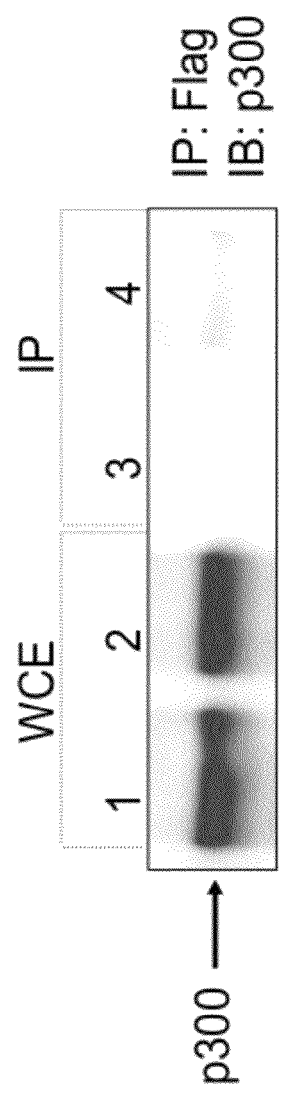

FIGS. 5a-c are autoradiograms illustrating MSF-A association to the HIF-1α complex. HEK 293 cells were co-transfected with two of the three expression vectors as in FIGS. 3a-f, and two days following transfection the cells were subjected to IP analysis using anti-HIF-1α (FIGS. 5a-b) or anti-Flag (FIG. 5c) antibodies, followed by IB using the anti-Flag (FIG. 5a) or anti-p300 (FIGS. 5b-c; Santa Cruz Biotechnology Inc., Santa Cruz, Calif.) antibodies. Lanes 1 and 3-EV and HIF-1α; lanes 2 and 4-MSF-A and HIF-1α.

Figure 6:
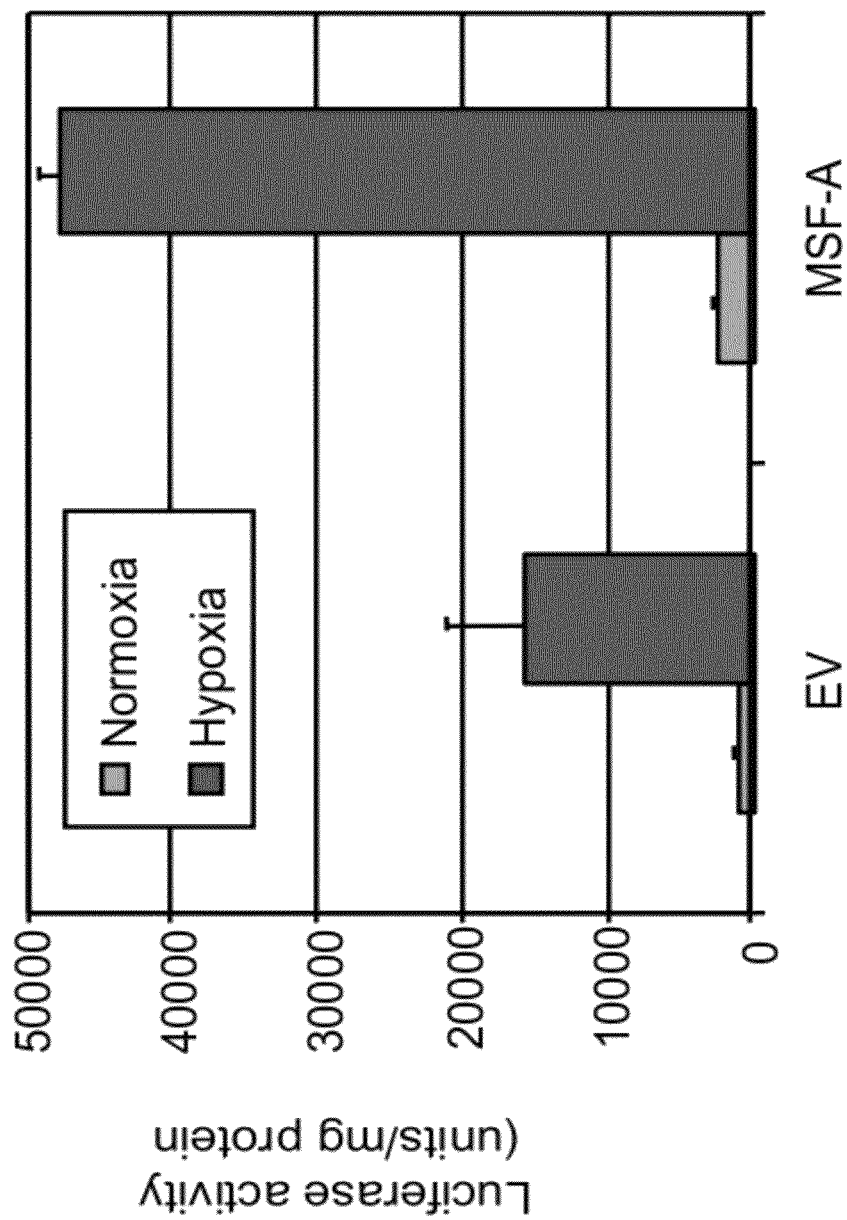

FIG. 6 is a graph illustrating reporter gene activity under normoxia or hypoxia. PC-3 cells were co-transfected with a plasmid expressing the luciferase gene under the control of hypoxia response element (HRE) and with either the p3xFlag-cmv-25 (EV) or the p3xFlag-MSF-A vector. Twenty-four hours following transfection, cells were left under normoxia or were subjected to hypoxia for overnight, following which the luciferase luminescence assay was employed. Results are expressed as average of triplicates. P value<0.05.

Figure 7:
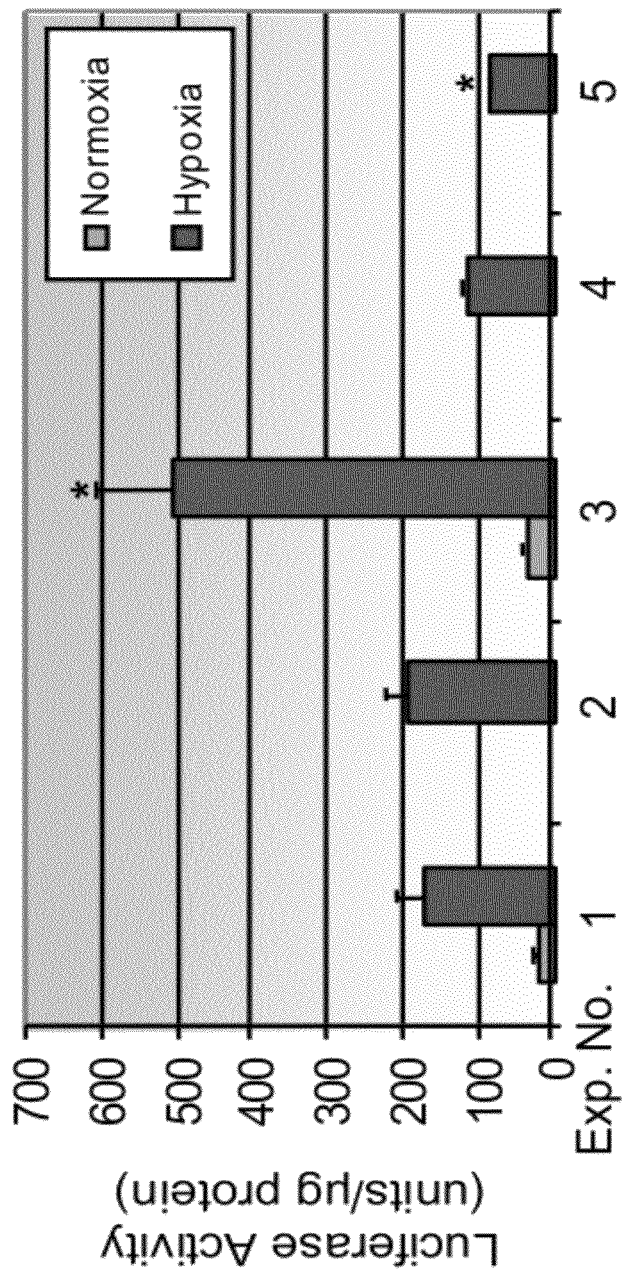

FIG. 7 is a graph depicting luciferase activity (a reporter of HIF-1α transcriptional activation) as a function of the presence or absence of the N-terminus of the MSF-A protein. HEK 293 cells were co-transfected with 0.1 μg HRE-dependent luciferase reporter 1pBI-GL V6L (Post, D. E., and Van Meir, E. G. 2001. Generation of bidirectional hypoxia/HIF-responsive expression vectors to target gene expression to hypoxic cells. Gene Ther 8, 1801-1807., Mabjeesh, N. J., et al., 2002, Geldanamycin induces degradation of hypoxia-inducible factor 1alpha protein via the proteasome pathway in prostate cancer cells. Cancer Res 62, 2478-2482) and the wild type (WT) MSF-A (p3xFlag-MSF-A), ΔN-MSF-A (ΔN) (p3xFlag-ΔN-MSF-A) or empty vector (EV) (p3xFlag-cmv-25) constructs as follows: Experiment (Exp.) No. 1=1 μg EV; Exp. No. 2=0.5 μg EV and 0.5 μg WT; Exp. No. 3—1 μg WT; Exp. No. 4=0.5 μg EV and 0.5 μg ΔN; Exp. No. 5=1 μg ΔN. After 24 hours of transfection, cells were subjected to normoxia or hypoxia for overnight and then analyzed for luciferase luminescence assay. Luciferase activity is presented as relative units per μg protein in each experiment. Columns represent means; bars represent SD; n=3; *, p<0.05 compared to hypoxia of EV. Note the significant decrease of luciferase activity in cells grown under hypoxia and transfected with the N-terminus truncated form (ΔN) of MSF-A as compared with cells transfected with the wild-type form of MSF-A. Also note that under normoxia, when the luciferase activity is hardly detected, no significant difference is obtained.

Figure 8:
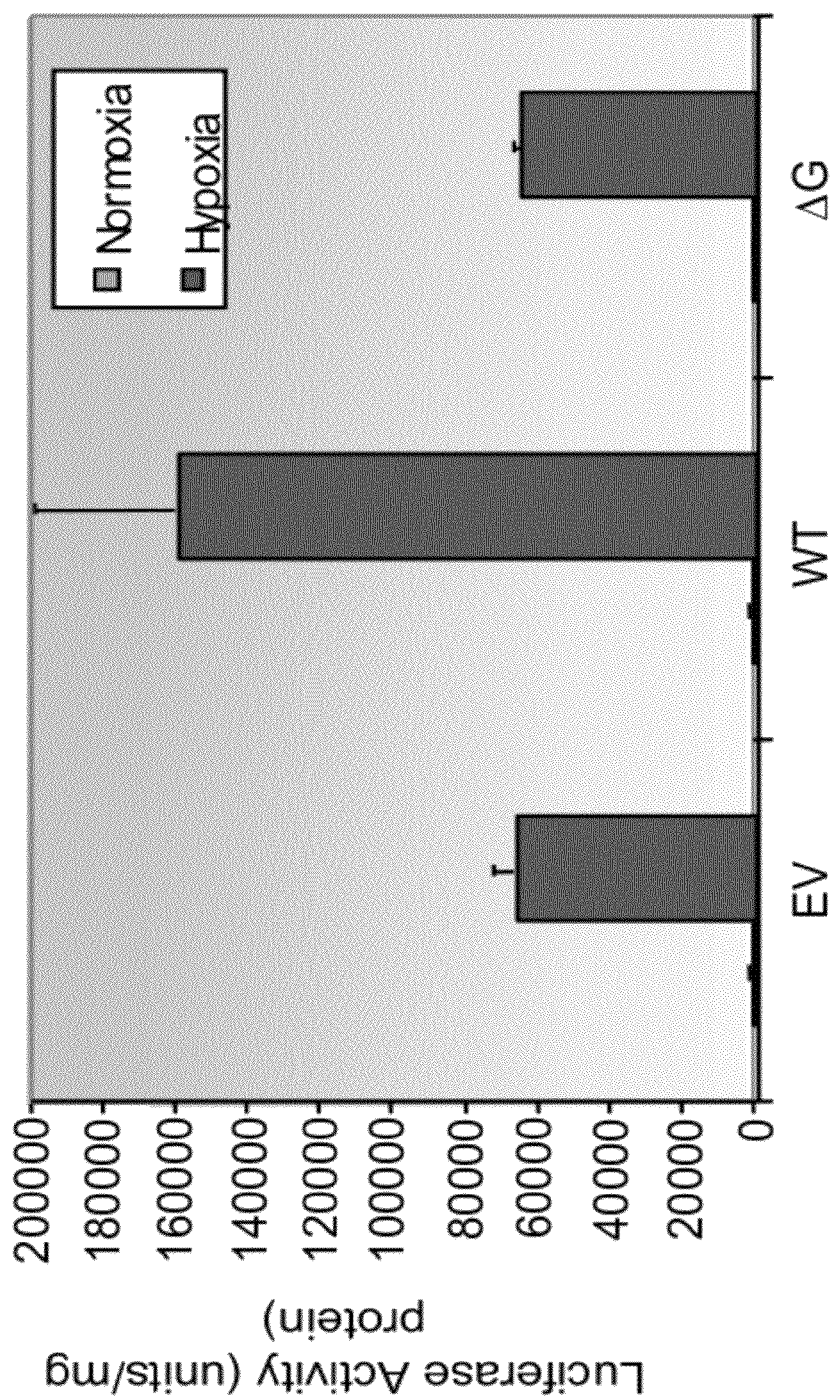

FIG. 8 is a graph depicting luciferase activity (a reporter of HIF-1α transcriptional activation) as a function of the presence or absence of the GTP binding site of MSF-A (ΔG). HEK 293 cells were cotransfected with HRE-dependent luciferase reporter and the expression vector encoding wild-type MSF-A (WT) (p3xFlag-MSF-A), the deleted GTP binding site form of MSF-A (ΔG) (p3xFlag-ΔG-MSF-A) or empty vector (EV) (p3xFlag-cmv-25) and then were exposed to hypoxia conditions as described in the description of FIG. 4, hereinabove. Luciferase activity is presented as relative units per μg protein in each experiment. Columns represent means; bars represent SD; n=3. Note the non-significant effect of the ΔG-MSF-A on HIF-1α activity.

Figure 9A:
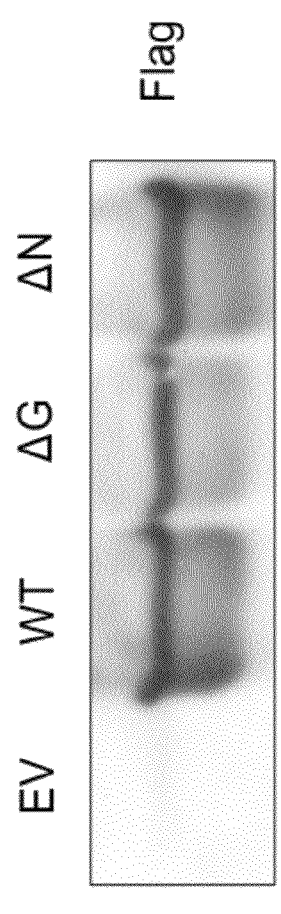
Figure 9B:
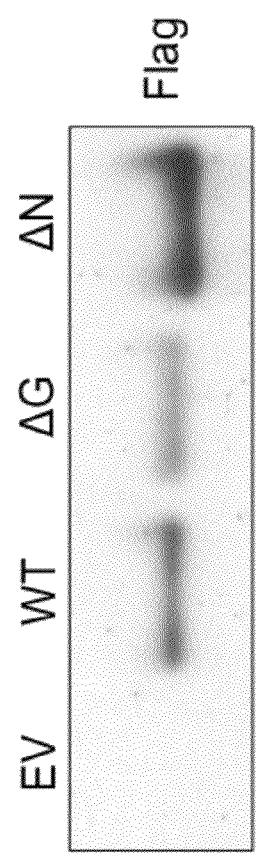
Figure 9C:
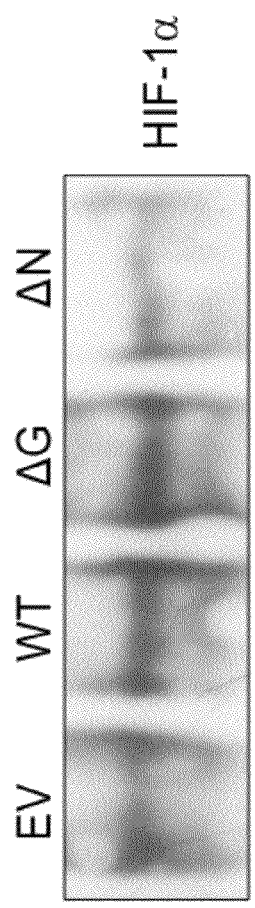

FIGS. 9a-c are Western blot analyses of FLAG (MSF-A; FIGS. 9a and b) and HIF-1α (FIG. 9c) depicting the interaction between HIF-1α and the WT or deleted forms of MSF-A. HEK 293 cells were transiently co-transfected with expression vector encoding Flag-MSF-A (WT; p3xFlag-MSF-A), Flag-ΔG (ΔG; p3xFlag-ΔG-MSF-A), Flag-ΔN (ΔN; p3xFlag-ΔN-MSF-A) or empty vector (EV; p3xFlag-cmv-25). After 48 hours, the cells were lysed, subjected for immunoprecipitation (IP) using HIF-1α antibody and then immunoblotted (IB) with HIF-1α or Flag antibodies. FIG. 9a—whole cell extracts (WCE) subjected to IB with the Flag antibody (MSF-A); FIG. 9b—IP prepared by the HIF-1α antibody were subjected to IB with the Flag antibody (MSF-A); FIG. 9c—IP prepared by the HIF-1α antibody were subjected to IB with the HIF-1α antibody.

FIGS. 10a-b depict MSF-A expression (FIG. 10a) and activation of HIF-1α (FIG. 10b) in MSF-A stably transfected PC-3 cells. FIG. 10a is an immunoblot of PC-3 cells stably transfected with the MSF-A vector (p3xFLAG-MSF-A; clones numbers 8, 9, 10, 11, 12, 13, 15, 16, 17, 20, 22, 23, 24, 25, 28, 29, 30) or the EV (p3xFlag-cmv-25) using the anti-Flag antibody. Neomycin-resistant clones were grown under normoxic conditions, harvested and analyzed for MSF-A expression by immunoblotting with Flag antibody. Note the high expression level of MSF-A in stably transfected clones numbers (#) 7, 8, 9, 10, 11, 12, 13, 15, 16, and 17. FIG. 10b is a graph depicting luciferase activity in various stably MSF-A transfected cells. Parental PC-3 cells and selected stably transfected clones [transfected with the EV or MSF-A (clone numbers 7, 11 and 25)] were transiently transfected with 1 μg of the HRE-dependent luciferase reporter (pBI-GL V6L) for HIF-1 transcriptional activity. Luciferase activity is presented in units per mg protein in each transfected cells. Columns=means; bars=SD; n=3; *, p<0.05 compared to hypoxia of EV.

Figure 11:
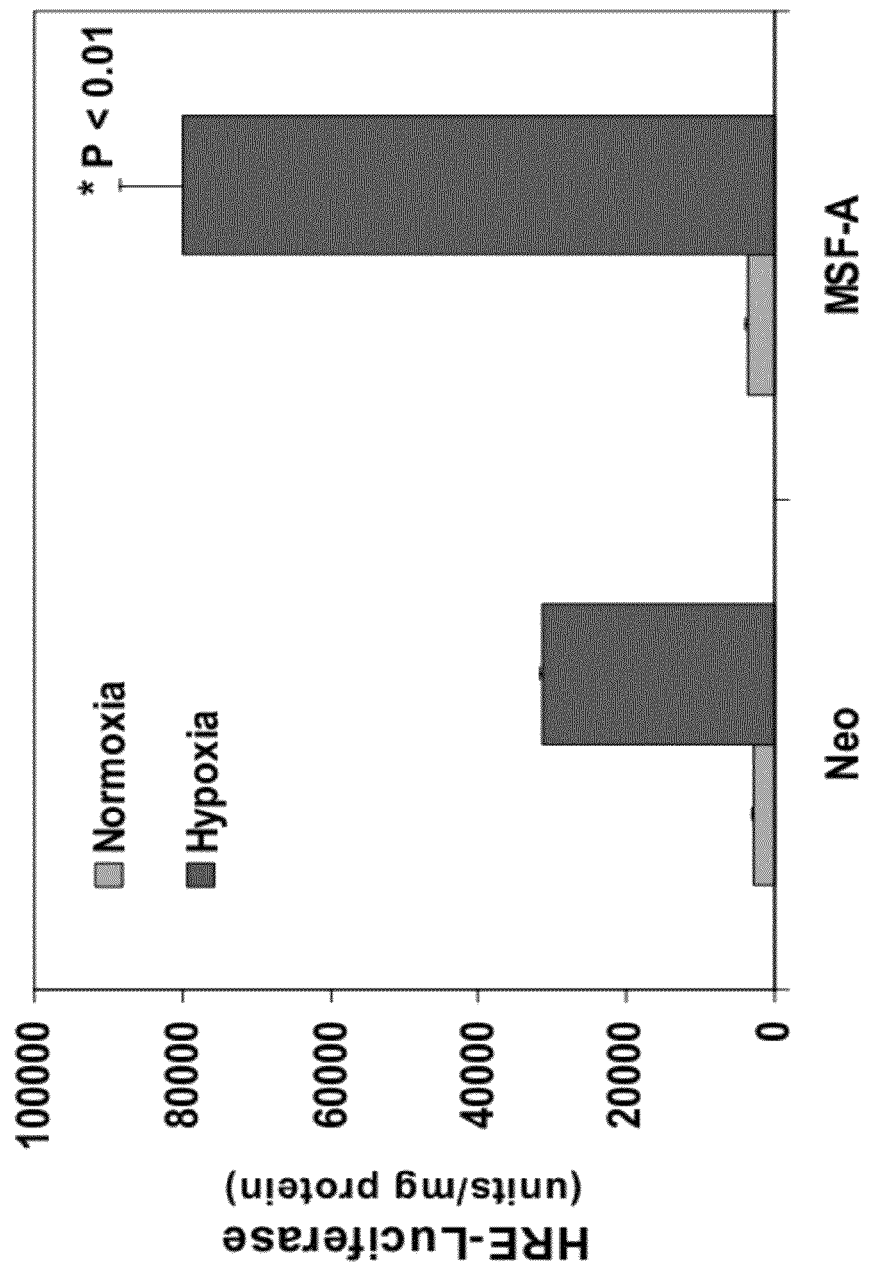

FIG. 11 is a graph depicting enhancement of luciferase activity in cells stably transfected with MSF-A. Pooled clones of PC-3 cells stably transfected with the MSF-A expression vector (MSF-A) or the empty vector (Neo) were subjected to reporter luciferase assay under normoxia or hypoxia conditions. Note the significant difference in luciferase activity under hypoxia in cells stably expressing the MSF-A protein as compared with cells transfected with the empty vector.

FIGS. 12a-f are RT-PCR analyses depicting HIF-1α mediated activation of various genes in cells transfected with the expression vector alone (Neo) or the MSF-A expression vector (MSF-A). Total RNA was isolated from PC-3-Neo and PC-3-MSF-A cells grown under normoxic (lanes 1 and 2) and hypoxic (lanes 3 and 4) conditions. Semi-quantitative RT-PCR analysis was performed using VEGF, Glut-1, ET-1, CA-IX, HIF-1α and β-actin primers (SEQ ID NOs:4200-4211 as described under General Materials and Experimental Methods). Lane 1—Neo, lane 2—MSF-A, lane 3—Neo, lane 4—MSF-A, lane 5—water (negative control). Note the significant increased expression of VEGF in PC-3-MSF-A cells grown under hypoxia (lane 4 in FIG. 12a) as compared with PC-3-MSF-A cells grown under normoxia (lanes 2 in FIG. 12a) as well as compared with PC-3-Neo cells grown under either hypoxia (lane 3 in FIG. 12a) or normoxia (lane 1 in FIG. 12a).

Figure 13:
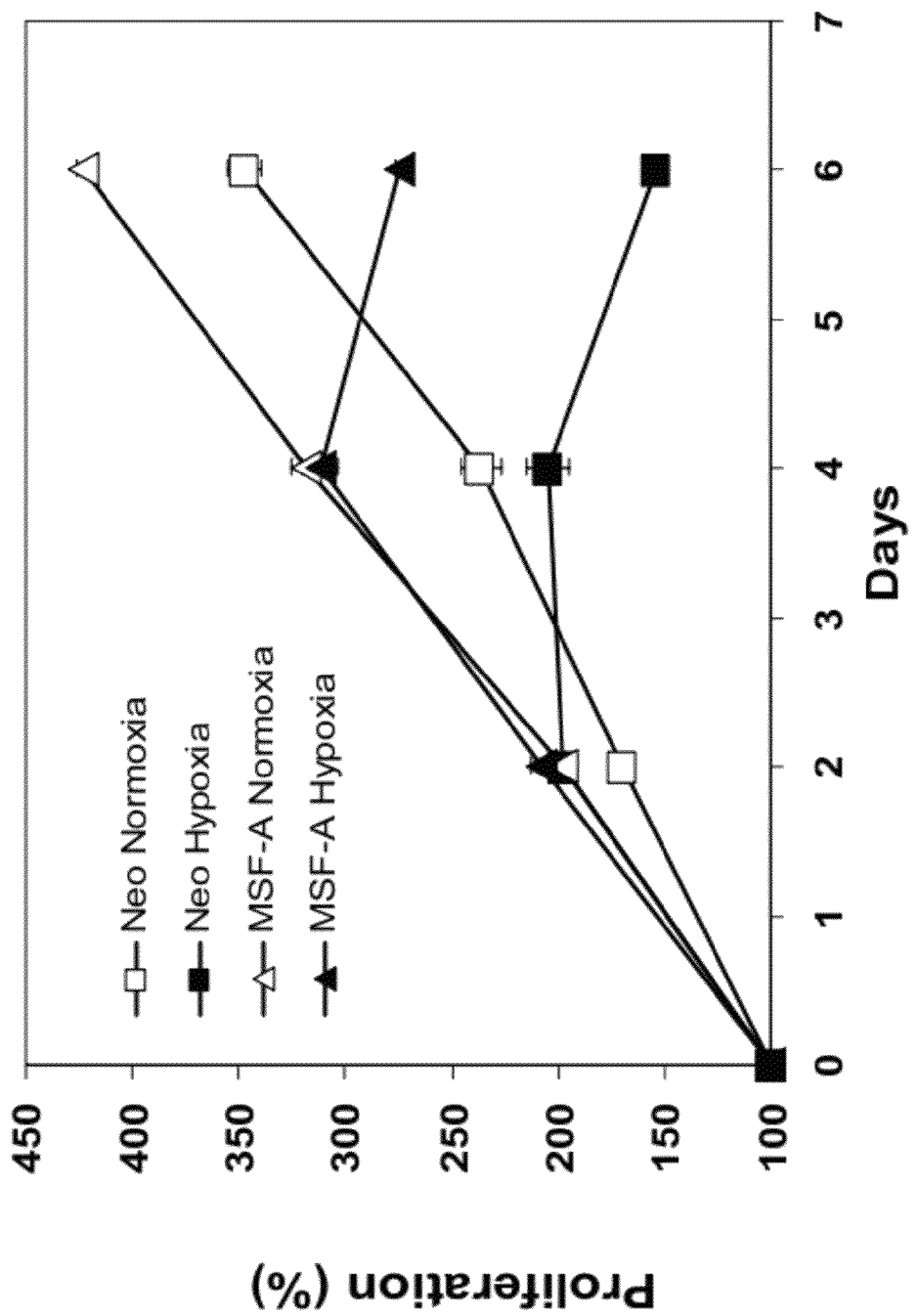

FIG. 13 is a graph depicting the effect of MSF-A over-expression on cell proliferation. PC-3-Neo and PC-3-MSF-A cells were grown under normoxic and hypoxic conditions for the indicated time and then analyzed for proliferation using XTT assay. Proliferation was expressed as increase in % of the initial O.D. measured on the next day of seeding which was considered 100%. Growth media were not changed until the end of the experiment.

FIGS. 14a-g are microscopic photographs (FIGS. 14a-f) and a graph depicting the effect of MSF-A over-expression on colony formation and growth (FIG. 14g). PC-3-Neo and PC-3-MSF-A cells were grown for 4 weeks in soft agar under normoxic conditions. Colonies were observed and counted. FIGS. 14a, c, and e—representative colonies from each plate seeded with PC-3-Neo cells; FIGS. 14b, d, and f—representative colonies from each plate seeded with PC-3-MSF-A cells; FIG. 14g-quantitative analysis of colony number from each cell type. Columns=means; bars=SD; n=3.

Figure 15A:
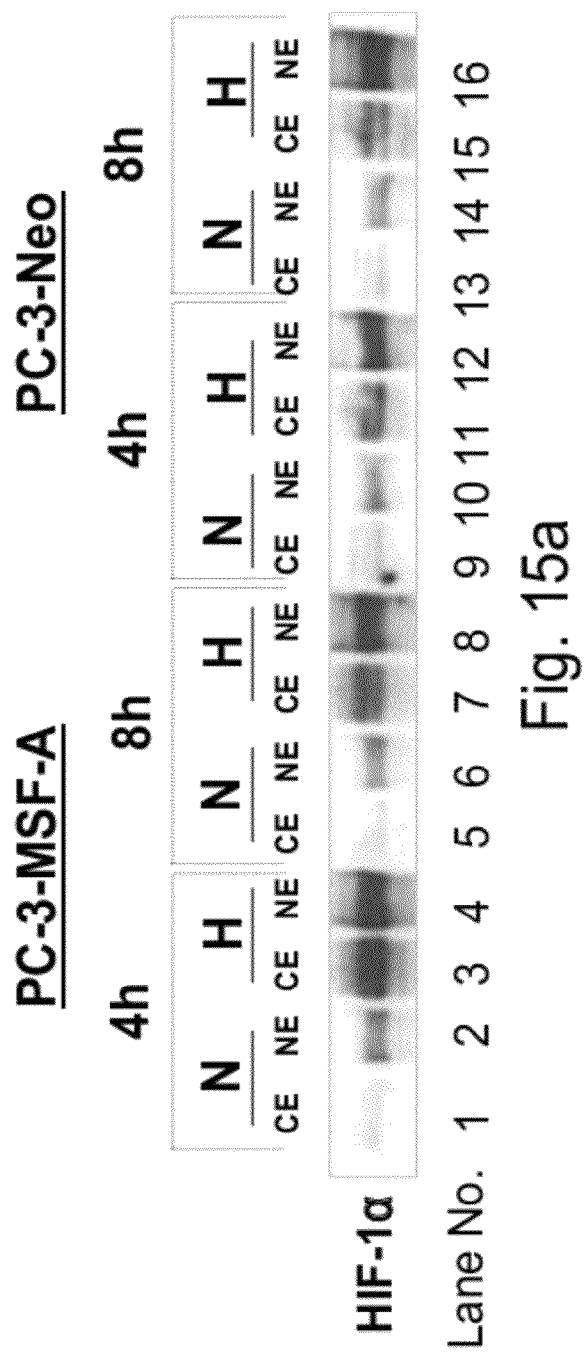
Figure 15B:
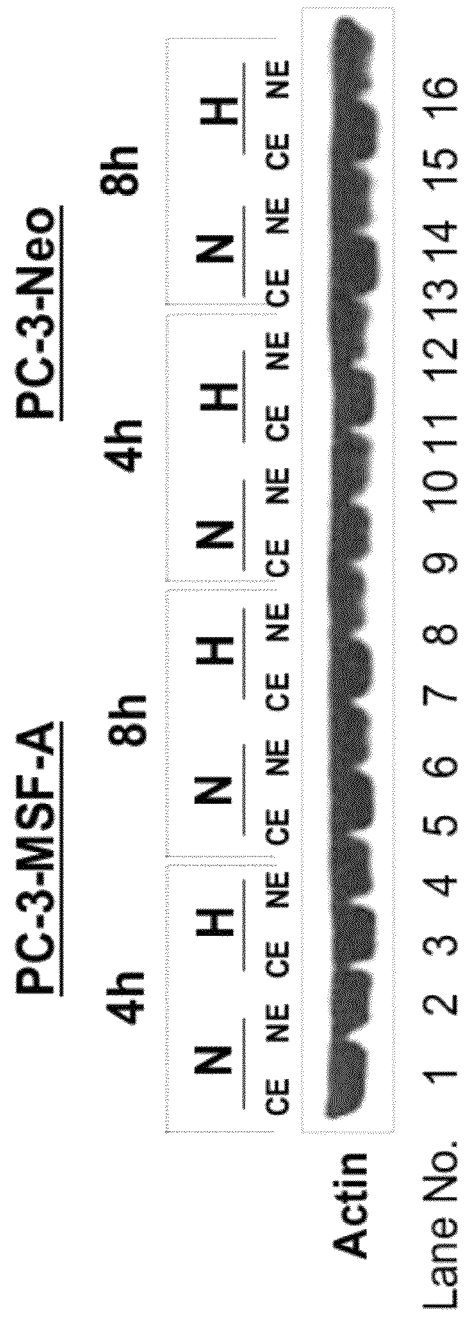

FIGS. 15a-b are Western blot analyses depicting HIF-1α (FIG. 15a) and actin (FIG. 15b) expression level in PC-3-Neo and PC-3-MSF-A cells grown under normoxia (N) or subjected to hypoxia (H). PC-3-Neo cells (lanes 9-16) or PC-3-MSF-A cells (lanes 1-8) were grown under normoxia (lanes 1-2,5-6, 9-10, 13-14) or hypoxia (lanes 2-4,7-8, 11-12, 15-16) for 4 hours (lanes 1-4 and 9-12) or 8 hours (lanes 5-6 and 13-16) as indicated. Cytosolic (CE; lanes 1, 3, 5, 7, 9, 11, 13, and 15) or nuclear (NE; lanes 2, 4, 6, 8, 10, 12, 14, and 16) extracts were prepared, analyzed by SDS-PAGE, and immunoblotted with antibodies to HIF-1α and actin.

Figure 16A:
Figure 16B:
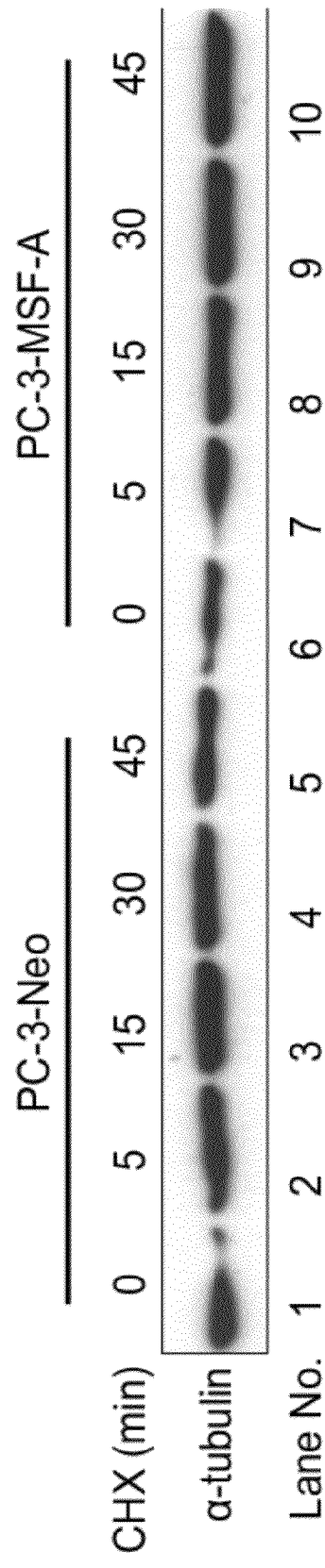
Figure 16C:
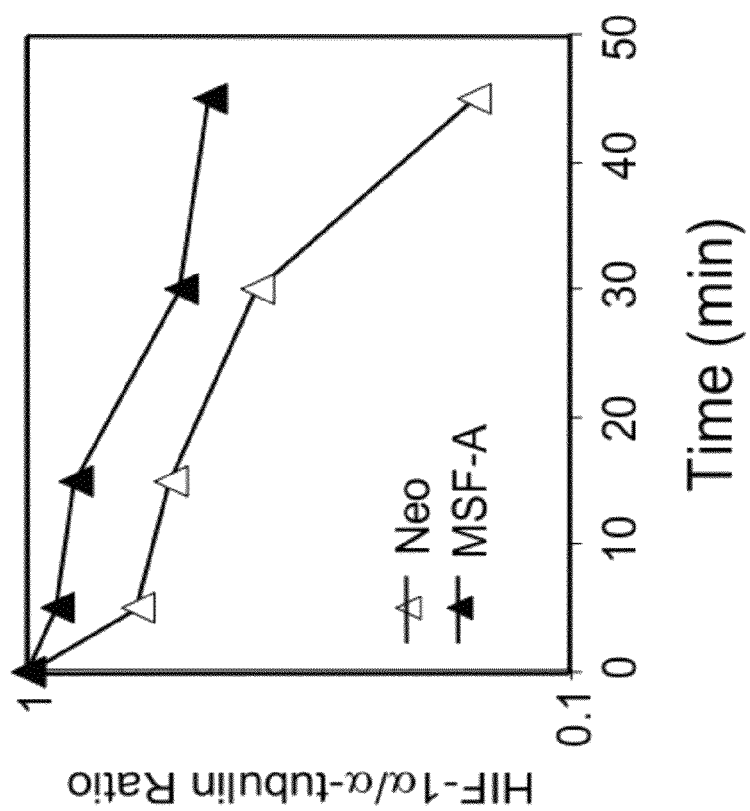

FIGS. 16a-c are Western blot analyses depicting the effect of cycloheximide (CHX) on the expression level of HIF-1α (FIG. 16a) and α-tubulin (FIG. 16b) in PC-3-Neo or PC-3-MSF-A cells grown under normoxia. CHX was added to PC-3-Neo (lanes 1-5) or PC-3-MSF-A (lanes 6-10) at a final concentration of 10 μg/ml, for 0 (lanes 1 and 6), 5 (lanes 2 and 7), 15 (lanes 3 and 8), 30 (lanes 4 and 9) and 45 (lanes 5 and 10) minutes. Whole cell extracts were prepared and resolved by SDS-PAGE and Western blotting was performed with antibodies against HIF-1α (FIG. 16a) or α-tubulin (FIG. 16b). FIG. 16c is a graph depicting quantitation of the results obtained in FIGS. 16a and b expressed as the ratio of HIF-1α expression level normalized to that of α-tubulin. Note, the relatively slow degradation of HIF-1α in cells over-expressing the MSF-A protein, with a degradation half-life of 40 minutes as compared to the degradation half-life of less than 20 minutes in PC-3-Neo cells (FIG. 16c).

FIGS. 17a-b depict pulse-chase analysis of HIF-1α. PC-3-Neo and PC-3-MSF-A cells were labeled with $^{35}$S-methionine and pulse-chased in complete medium containing for the indicated time in hours (h). FIG. 17a-equal amounts of protein from each cell lysate were subjected to immunoprecipitation with anti-HIF-1α antibody, resolved by SDS-PAGE and subjected to autoradiography. FIG. 17b-quantification of the autoradiographic HIF-1α signal by densitometry. Note, the relatively slower degradation of HIF-1α in cells over-expressing the MSF-A protein, with a degradation half-life of 45 minutes as compared to the degradation half-life of 25 minutes in PC-3-Neo cells.

FIGS. 18a-b depict stabilization of HIF-1α in PC-3-MSF-A stably transfected cells. Whole cell lysates from single clones of stably transfected PC-3 cells (expressing different amounts of Flag-MSF-A protein) were grown under normoxia (lanes 1-6) or hypoxia (lanes 7-12) were analyzed on SDS-PAGE and immunoblotted with HIF-1α (FIG. 18a) and Flag (FIG. 18b) antibodies. Note the significant reduction (under hypoxia conditions) in the ubiquitinated species of HIF-1α in MSF-A stably transfected cells (clones 1-5; lanes 8-10 and 12 in FIG. 18a) as compared to cells transfected with the expression vector alone (Neo; lane 7 in FIG. 18a). Also note the correlation between the level of MSF-A expression and the inverse effect on HIF-1α ubiquitinated species (compare e.g., lane 11 to 8 in FIGS. 18a and b).

FIGS. 19a-b are Western blot analyses depicting the effect of proteasome inhibition on HIF-1α (FIG. 19a) or actin (FIG. 19b) expression levels in PC-3-MSF-A or PC-3-Neo cells. PC-3-Neo (lanes 1-3) and PC-3-MSF-A (lanes 4-6) cells were treated for 4 hours with either 0.1 DMSO (lanes 1 and 4) or with 5 (lanes 2 and 5) and 20 (lanes 3 and 6) μM MG-132. Whole cell lysates were prepared and equal amounts of protein from each cell lysate were resolved by SDS-PAGE, transferred and immunoblotted with antibodies against HIF-1α (FIG. 19a) and actin (FIG. 19b). Ub-HIF-1α points to ubiquitinated HIF-1α protein species.

FIGS. 20a-b are Western blot analyses of HIF-1α immunoprecipitates depicting the expression level of HIF-1α (FIG. 20a) and ubiquitin (FIG. 20b) in PC-3-Neo and PC-3-MSF-A cells. PC-3-Neo (lanes 1-2) and PC-3-MSF-A (lanes 3-4) cells were treated for 4 hours with either 0.1 DMSO (lanes 1 and 3) or with 10 μM MG-132 (lanes 2 and 4). Whole cell lysates were prepared and subjected to immunoprecipitation (IP) with HIF-1α antibody Immunoprecipitates were resolved on SDS-PAGE and immunoblotted (IB) with HIF-1α (FIG. 20a) and ubiquitin (FIG. 20b) antibodies. Ub-HIF-1α points to ubiquitinated HIF-1α protein species.

Figure 21A:
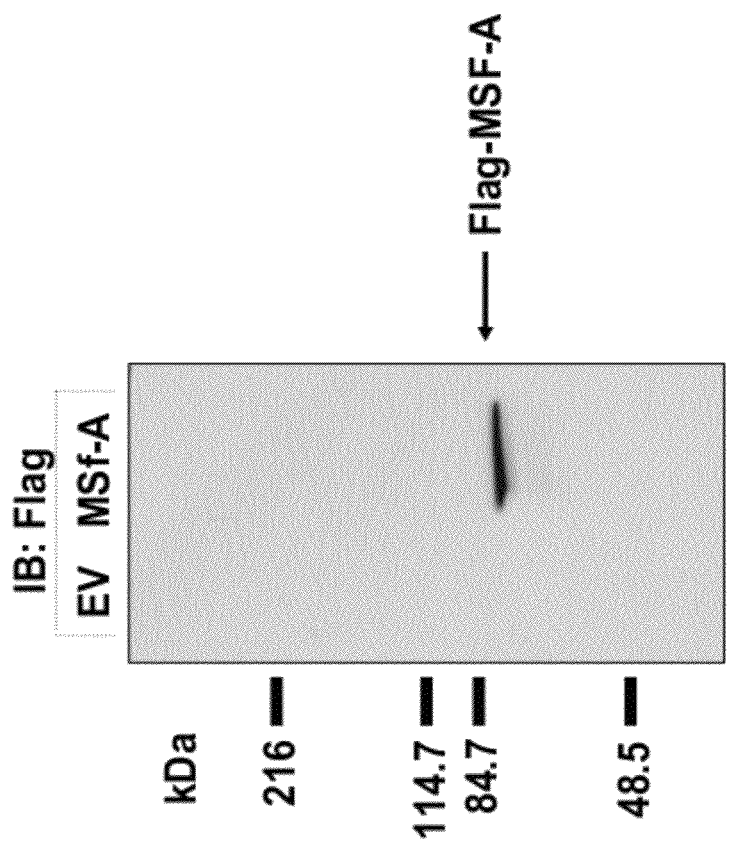
Figure 21B:
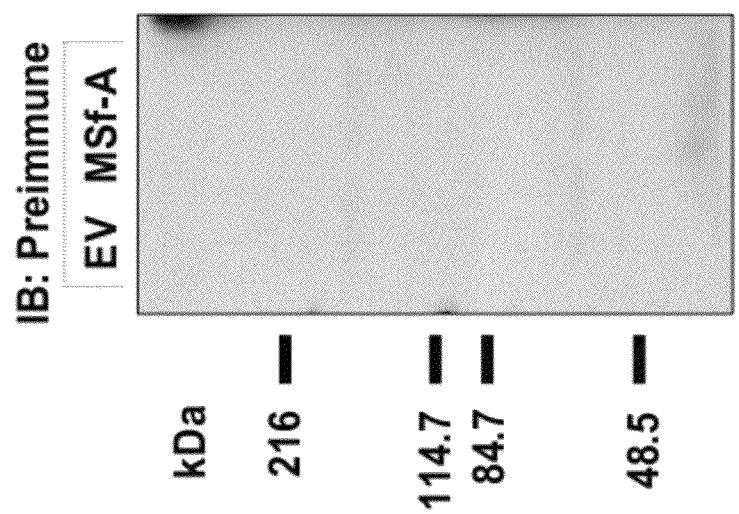
Figure 21C:
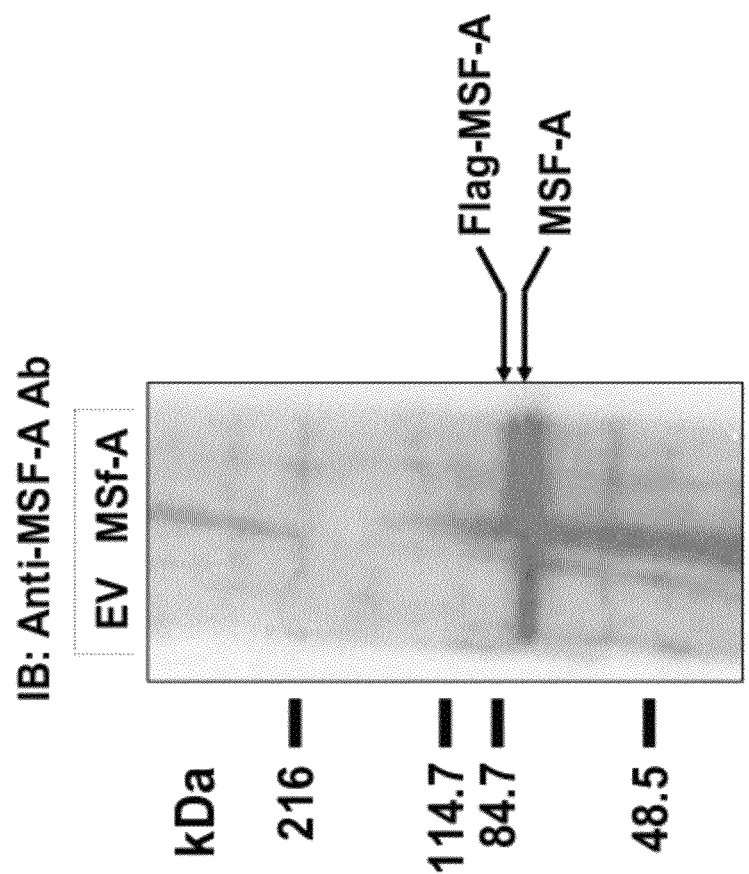

FIGS. 21a-c are Western Blot analyses illustrating the specificity of the anti-MSF-A immune serum. PC-3 cells were transfected with either the expression vector (EV) or the p3xFlag-MSF-A vector (MSF-A) and were subjected to Western Blot analyses (IB) using the anti-Flag antibody (FIG. 21a), preimmune serum (FIG. 21b) or serum after immunization with a peptide corresponding to the N-terminal of MSF-A protein (FIG. 21c). Note the presence of two MSF-A positive bands in PC-3 cells transfected with the p3xFlag-MSF-A vector, corresponding to the Flag—and endogenous MSF-A proteins (FIG. 21c).

Figure 22A:
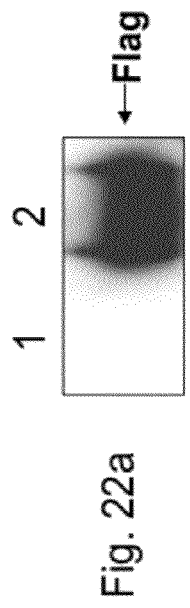
Figure 22B:
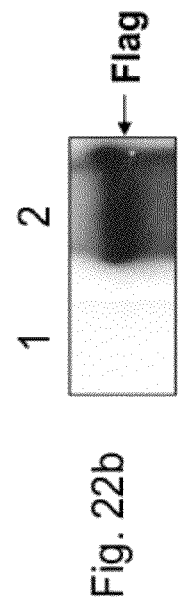
Figure 22C:
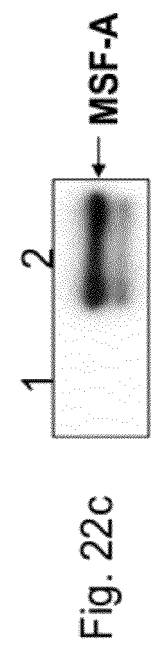
Figure 22D:
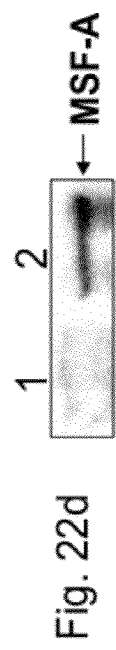

FIGS. 22a-d FLAG (FIGS. 22a-b) or sera-raised MSF-A (FIGS. 22c-d) immunoblot analyses of FLAG IP (FIGS. 22a and c) or whole cell extracts (FIGS. 22b and d). HEK 293 were transfected with expression vector encoding Flag-MSF-A (lane 2) or empty vector (EV, lane 1) and whole cell extracts were prepared. Lysates were subjected to immunoprecipitation (IP) with Flag antibody Immunoprecipitates were resolved on SDS-PAGE and analyzed by immunoblotting (IB) with Flag antibody or sera raised against the N-terminus of MSF-A. FIG. 22a—IP with FLAG and IB with FLAG; FIG. 22b—no IP and IB with FLAG; FIG. 22c—IP with FLAG and IB with sera-raised MSF-A; FIG. 22d—no IP and IB with the sera-raised MSF-A.

FIGS. 23a-c are Western blot analyses depicting the expression of HIF-1α (FIG. 23a) and MSF-A (FIG. 23b) in the nuclear rather than the cytosolic cell fraction. PC-3 or CL-1 cells were grown for 24 hours under either normoxia or hypoxia following which the expression level of HIF-1α (FIG. 23a), MSF-A (FIG. 23b) or α-tubulin (FIG. 23c) was detected using Western blot analysis. CE=cytosolic extract; NE=nuclear extract; N=normoxia; H=hypoxia. Note that while MSF-A and HIF-1α localize at the cell nuclear fraction, the α-tubulin protein localizes at both the nuclear and cytoplasm fractions.

FIGS. 24a-d illustrate MSF-A immunofluorescence staining in PC-3 cells using MSF-A preimmune (FIGS. 24c-d) or immune sera (FIGS. 24e-f) under normoxia (FIGS. 24c and e) or hypoxia (FIGS. 24d and f).

FIGS. 25a-f illustrate HIF-1α and MSF-A co-localization in PC-3 cells using anti-HIF-1α (FIGS. 25a-b), anti-MSF-A (FIGS. 25c-d) or both antibodies (FIGS. 25e-f) under normoxia (FIGS. 25a, c, e) or hypoxia (FIGS. 25b, d, f).

Figure 26A:
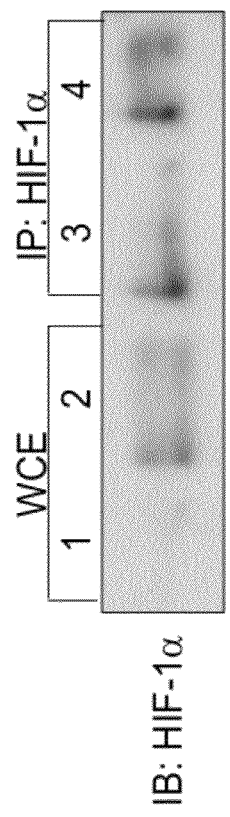
Figure 26B:
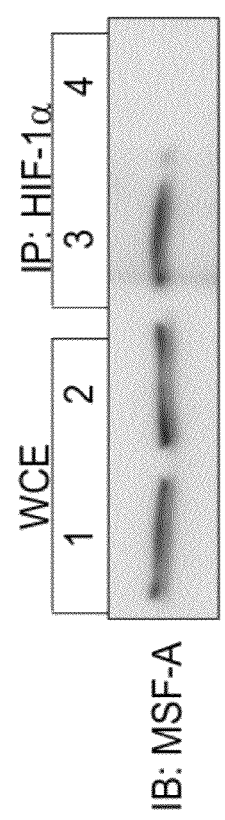
Figure 26C:
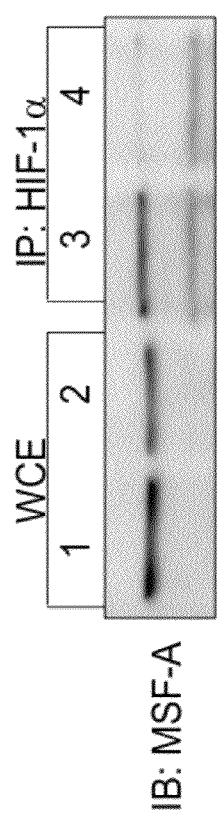

FIGS. 26a-c are Western Blot analyses of whole cell extracts (WCE) or HIF-1α-IP using anti-HIF-1α (FIG. 26a) or anti-MSF-A (FIGS. 26b-c) antibodies. PC-3 (FIGS. 26a-b) or CL-1 (FIG. 26c) cells were grown under normoxia or hypoxia and whole cell extracts or HIF-1α-immunoprecipitates were subjected to Western Blot analyses. Lanes 1 and 3—normoxia; lanes 2 and 4—hypoxia.

Figure 27:
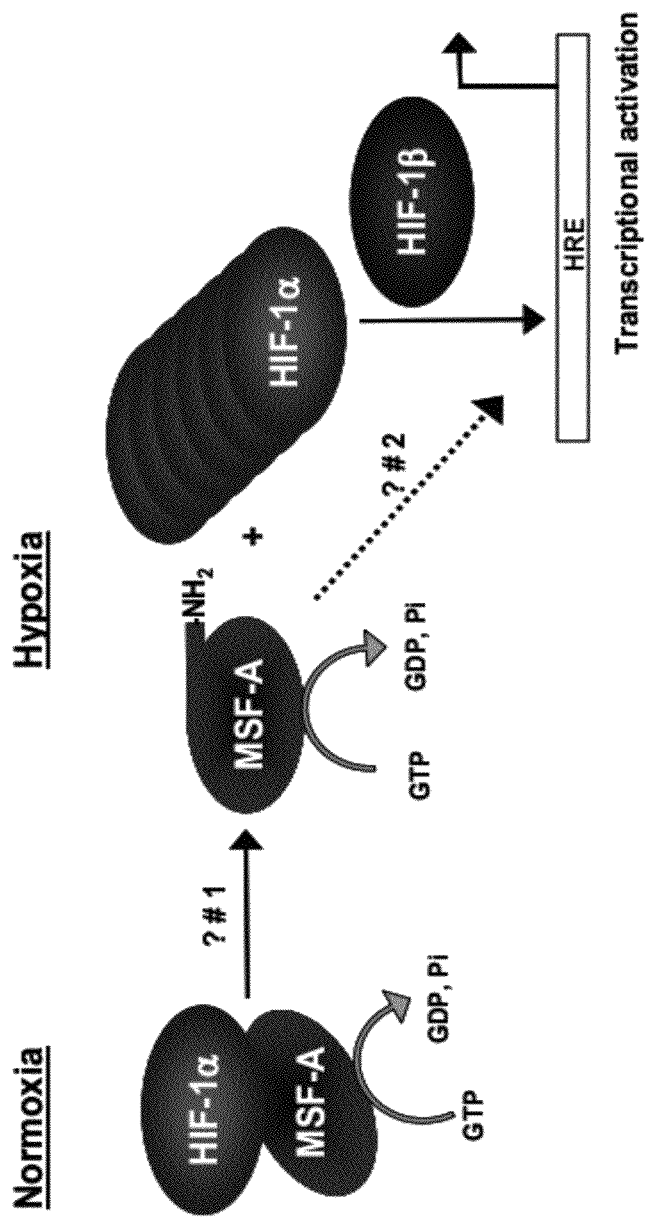

FIG. 27 is a schematic presentation depicting MSF-A involvement in the regulation of HIF.

Figure 28:
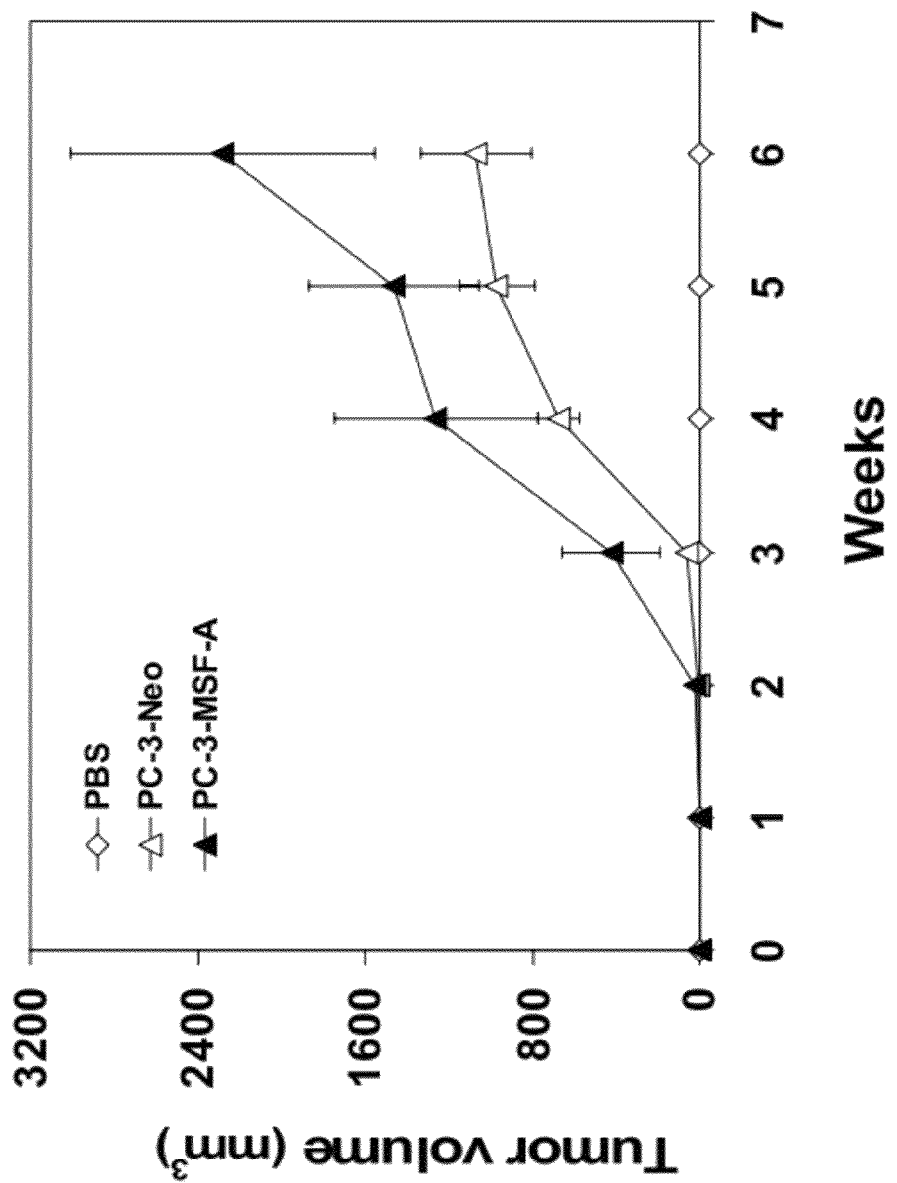

FIG. 28 is a graph depicting the effect of MSF-A over-expression on tumor volume. A prostate cancer xenograft model was established using PC-3-Neo and PC-3-MSF-A cells ($3 \times 10^6$) which were implanted subcutaneously into the right hind of nude mice. PBS was used as a negative control Animals were monitored for tumor volume measurements. Tumor volume measurements were calculated using the formula width$^2 \times$length$\times 0.52$. Mean±SEM (n=5) of representative experiments is shown. Note the significant increase in tumor volume in xenografts injected with cells over-expressing the MSF-A protein (PC-3-MSF-A).

Figure 29:
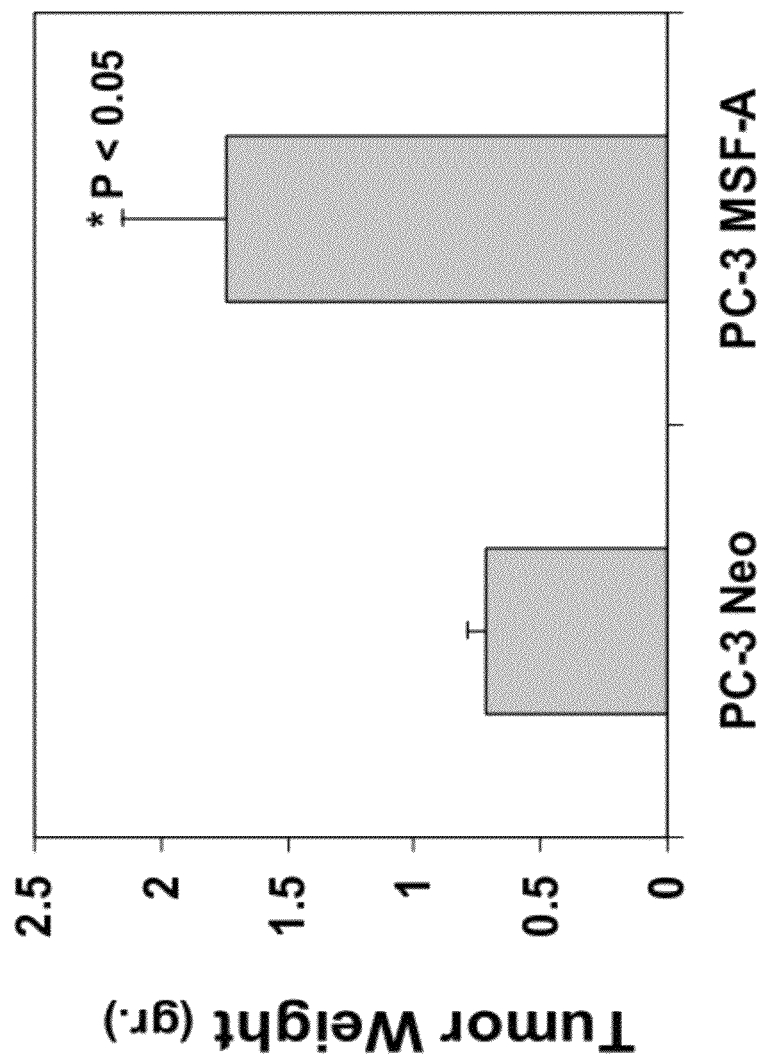

FIG. 29 is a graph depicting the effect of MSF-A over-expression on tumor weight. A prostate cancer xenograft model was established as described in FIG. 28. Mice were sacrificed after 6 weeks and tumors were processed for tumor weight measurements. Tumors were weighed immediately after dissection. Columns, means; bars, SEM; n=5; *, p<0.05. Note the significant increase in tumor weight in xenografts injected with cells over-expressing the MSF-A protein (PC-3-MSF-A).

FIGS. 30a-h are photomicrographs (FIGS. 30a-f) and graphs (FIGS. 30g-h) depicting MSF-A over-expression in tumors and angiogenesis in a prostate cancer xenograft model. Sections from both PC-3-Neo (FIGS. 30a, c, and e) and PC-3-MSF-A (FIGS. 30b, d, and f) tumors were subjected for Hematoxylin-eosin (H& E; FIGS. 30a-b) and immunostaining with Ki67 (FIGS. 30c and d) and CD34 (FIGS. 30e and f). FIG. 30g-Ki67 staining (%) was quantified by dividing the number of positive nuclei by the number of total nuclei in 40× magnification field multiplied by 100, of 5 paraffin-embedded tumor sections from each animal per group. Columns, average of the means of Ki67 staining from each animal; bars, SEM; n=5; *, p<0.05. FIG. 30h-Microvessel density (MVD) was determined by counting the capillaries positive for CD34 staining in 4× magnification field per total section area excluding necrotic areas in 5 paraffin-embedded tumor sections from each animal per group. Columns, average of the means of MVD from each animal; bars, SEM; n=5; *, p<0.05.

FIGS. 31a-f are RT-PCR analyses of MSF-A (FIG. 31a), VEGF (FIG. 31b), CA-IX (FIG. 31c), Glut-1 (FIG. 31d), ET-1 (FIGS. 31e) and β-actin (FIG. 31f) of RNA isolated from either PC-3-Neo (lane 1) or PC-3-MSF-A (lane 2)-derived tumors. Lane 3=water (negative control).

Figure 32A:
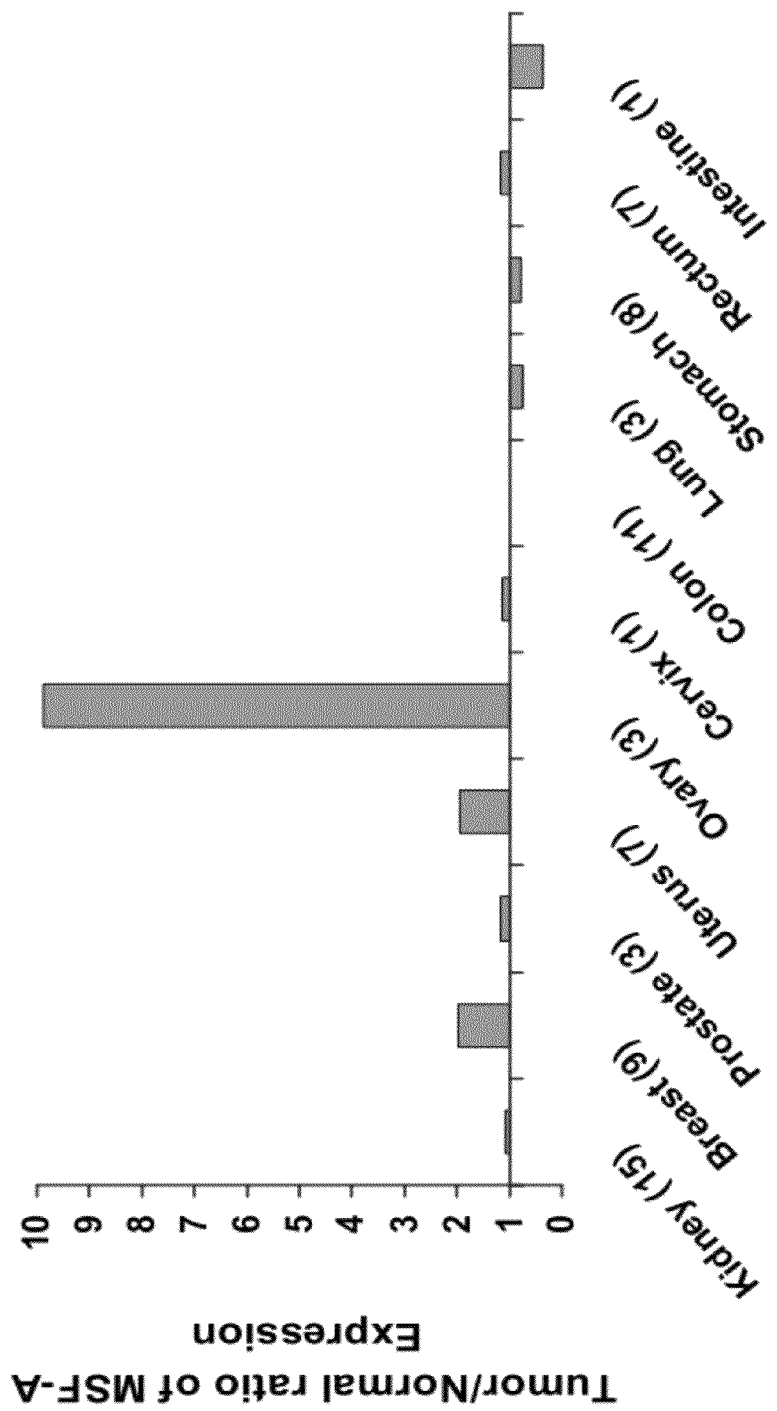
Figure 32B:
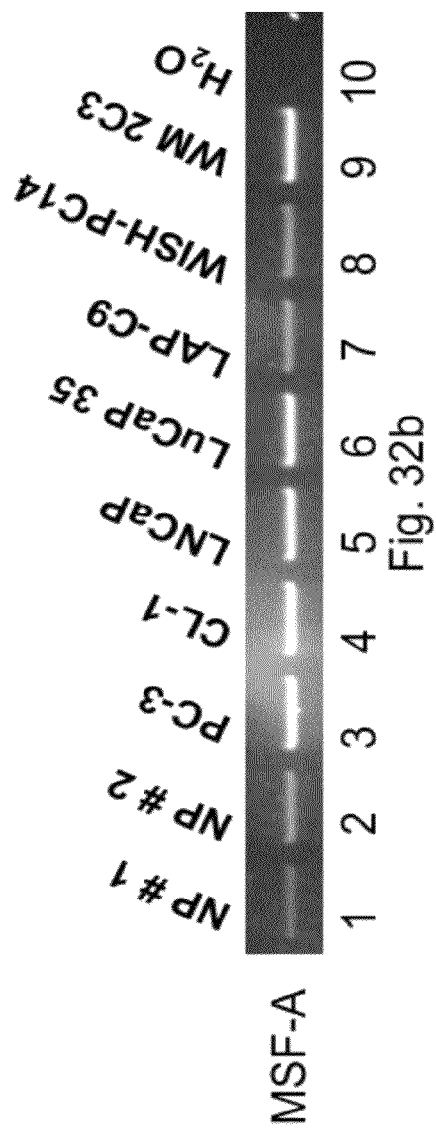
Figure 32C:
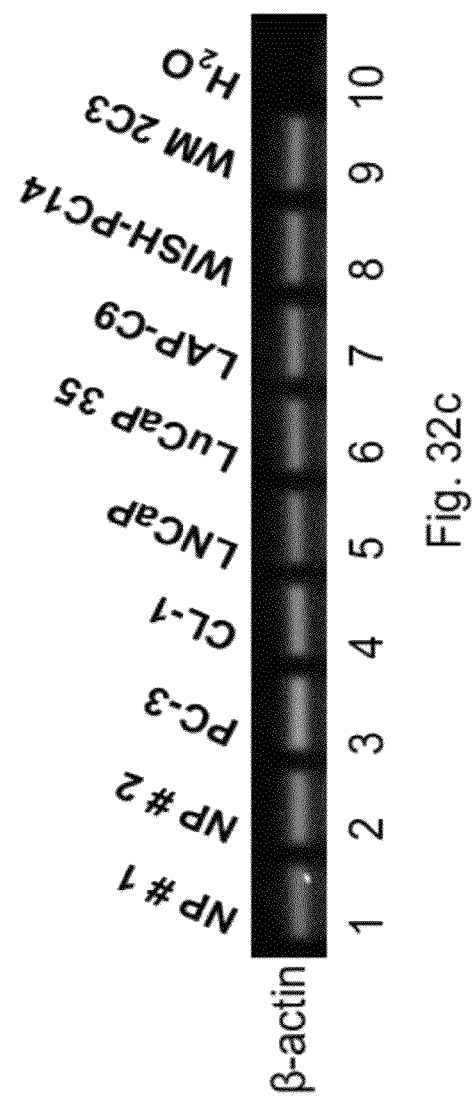
Figure 32D:
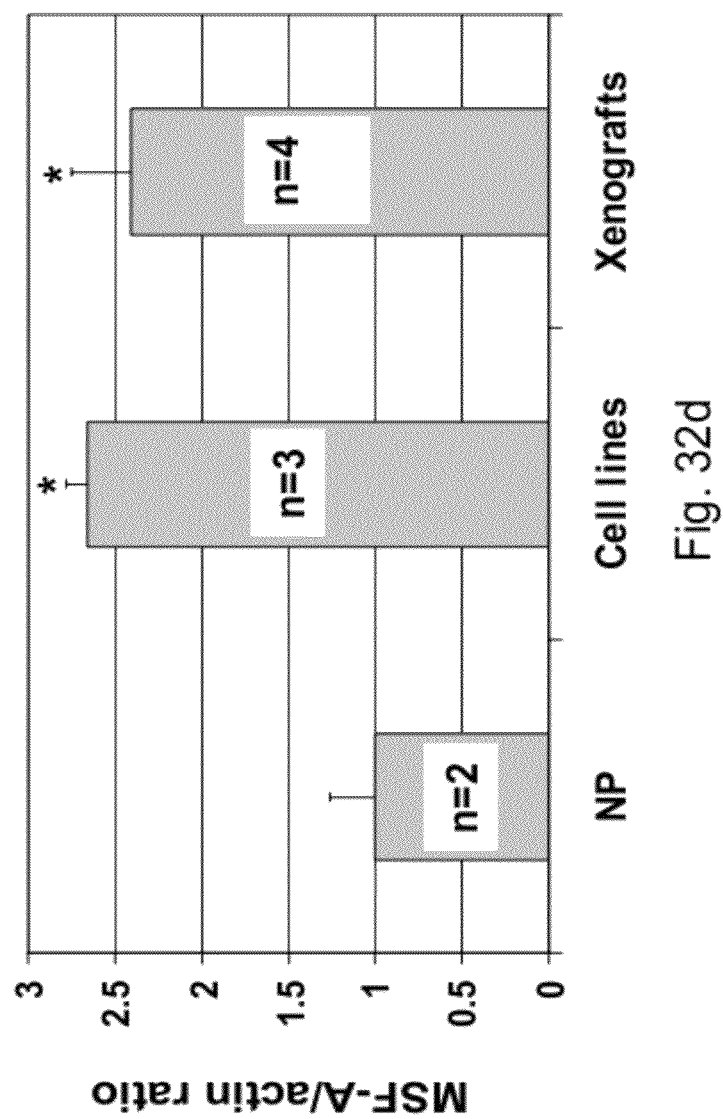

FIGS. 32a-d depict MSF-A mRNA expression in human tumors. FIG. 32a is a graph depicting normalized MSF-A expression levels in various tumors. Human Matched Tumor/Normal Expression Array (containing 68 pairs of tumor/normal different tissues) was hybridized with probe to MSF-A (SEQ ID NO:4214, the probe also reacts with other SEPT9 transcripts) and to β-actin (Ambion). Autoradiograms were analyzed, and the expression ratio of each tumor/normal was depicted in the graph. Numbers in parenthesis point to the number of pairs of each tumor type. FIGS. 32b-c are RT-PCR analyses of MSF-A (FIGS. 32b) and β-actin (FIG. 32c) in various normal and cancerous tissues or cells. Total RNA was isolated from two different normal prostate tissues [NP, NP#1 (lane 1), NP#2 (lane 2)], prostate cancer cell lines [PC-3 (lane 3), CL-1 (lane 4), LNCaP (lane 5)1 and prostate cancer xenografts [LuCaP 35 (lane 6), LAP-C9 (lane 7), WISH-PC-14 (lane 8), WM 2C3 (lane 9)], and was analyzed by RT-PCR using primers specific to MSF-A (SEQ ID NOs:4 and 4199) and β-actin (SEQ ID NOs:4202-4205). FIG. 32d is a graph depicting normalization of the RT-PCR analyses shown in FIGS. 32b and c. Shown are the average densitometric quantification of MSF-A/actin expression in the normal prostate tissues (NP), the prostate cancer cell lines and xenografts.

DESCRIPTION OF THE PREFERRED EMBODIMENTS

The present invention is of agents capable of preventing the formation of, and/or dissociating an MSF-A-HIF-1α protein complex or of agents capable of stabilizing the MSF-A-HIF-1α protein complex which can be used to treat cancer or acute ischemia, respectively. Specifically, the present invention can be used to treat individuals having cancer using agents capable of downregulating the MSF-A and/or HIF-1α proteins.

The principles and operation of the methods of treating cancer or acute ischemia according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Over-expression of HIF-1α is found in the majority of solid tumors and cancer metastases in the areas of profound hypoxia [Quintero, 2004 (Supra)]. In addition, in many cases, the major reason for the failure of anti cancer therapy is the resistance of hypoxic cancer cells to both chemotherapy and radiation [Escuin, 2004 (Supra)]. Thus, HIF-1α has been recognized as a possible target for anti cancer therapy [Welsh, 2003 (Supra)].

Several agents capable of downregulating HIF-1 have been identified as potential anti-cancer agents including FK228, a histone deacetylase (HDAC) inhibitor [Mie Lee, 2003 (Supra)], PX-478, a small-molecule HIF-1 inhibitor, [Macpherson, 2004 (Supra)] and Bisphenol A, an environmental endocrine-disrupting chemical [Kubo, 2004 (Supra)]. However, the mechanisms leading to up- or down-regulation of HIFs in cancerous tumors are not yet clear, thus, limiting the use of HIF-1 inhibitors/suppressors as anti cancer agents.

While reducing the present invention to practice, the present inventor has uncovered that MSF-A, a myeloid/lymphoid leukemia septin-like fusion protein A, associates with HIF-1α both in vitro and in vivo (Example 1, FIGS. 1-5) and that MSF-A over-expression upregulates HIF-1α transcriptional activity (Example 2, FIG. 6). When in a complex with HIF-1α, MSF-A prevents proteasomal degradation of HIF-1α (Example 5, FIGS. 15-20). Moreover, as is further shown in FIGS. 28-32 and is described in Examples 8 and 9 of the Examples section which follows, MSF-A is over-expressed in various tumors and is capable of inducing tumor growth, angiogenesis and proliferation in vivo. These findings have led the present inventor to design agents which can be used to treat cancer by downregulating MSF-A dependent HIF-1α activity.

As described in Example 3 of the Examples section which follows, transfection of cells with the p3xFlag-ΔN-MSF-A expression vector encoding an N-terminal truncated form of the MSF-A protein resulted in inhibition of HIF-1α activation below the level observed in cells transfected with the empty vector (i.e., wild type, FIG. 7). In addition, transfection of cells with the p3xFlag-ΔG-MSF (lacking the GTP binding domain of MSF-A) resulted in lack of activation of HIF-1α transcriptional activity (levels of activation were similar to those observed with the empty vector, FIG. 8). On the other hand, as is shown in FIGS. 9*a*-*c*, both of these mutants (i.e., ΔG-MSF and ΔN-MSF) were co-immunoprecipitated with the HIF-1α protein demonstrating their ability to interfere with HIF-1α activity via the formation of the protein complex between HIF-1α and MSF-A.

Thus, according to one aspect of the present invention there is provided a method of treating cancer and/or inhibiting a growth of a cancerous tumor and/or metastases in an individual. The method is effected by providing to the individual an agent capable of downregulating an MSF-A-dependent HIF-1α activity in cells of the individual thereby treating the cancer and/or inhibiting the growth of the cancerous tumor and/or the metastases in the individual.

As used herein, the term "individual" includes mammals, preferably human beings at any age. Preferably, this term encompasses individuals which have been diagnosed with cancer, i.e., they have cancerous cells, a cancerous tumor and/or cancer metastases.

The phrase "treating" refers to inhibiting or arresting the development of a disease, and/or causing the reduction, remission, or regression of a disease, in an individual suffering from, or diagnosed with, the disease. Those of skill in the art will be aware of various methodologies and assays which can be used to assess the development of a disease, and similarly, various methodologies and assays which can be used to assess the reduction, remission or regression of a disease.

The terms "cancer" and/or "cancerous tumor" as used herein encompass solid and non-solid tumors such as prostate cancer, breast cancer, chemotherapy-induced MLL, stomach cancer, cervical cancer, endometrial cancer, ovarian cancer and the like.

As used herein the term "HIF-1α" refers to the hypoxia-inducible factor 1, alpha subunit isoform 1 (SEQ ID NO:11; GenBank Accession No. AAP88778), which is a member of the Per-ARNT-Sim (PAS) superfamily 1 and an aryl hydrocarbon receptor nuclear translocator (ARNT) interacting protein.

The phrase "MSF-A-dependent HIF-1α activity" as used herein, refers to HIF-1α protein activity (e.g., transcriptional activation of genes such as VEGF) which is dependent on the direct or indirect interaction with MSF-A, and/or on the activation, stabilization and/or prevention of degradation which is mediated by MSF-A.

As used herein the term "MSF-A: refers to the myeloid/lymphoid leukemia septin-like fusion protein A (MSF-A, GenBank Accession No. AAF23374, SEQ ID NO:3).

Downregulating an MSF-A-dependent HIF-1α activity can be effected by various approaches including, for example, directly or indirectly interfering with MSF-A dependent HIF-1α protein stabilization, promoting MSF-A dependent HIF-1α protein degradation and/or preventing the formation of MSF-A-HIF-1α complex or dissociating a pre-existing MSF-A-HIF-1α complex.

It will be appreciated that several approaches can be used to prevent the formation of and/or dissociate the MSF-A-HIF-1α protein complex in cells. These include downregulation of the expression level and/or activity of any of the proteins in the protein complex (i.e., MSF-A and/or HIF-1α) and thus preventing MSF-A-HIF-1α complex formation, interference with the protein complex or destabilization thereof.

Downregulation of MSF-A and/or HIF-1α can be effected on the genomic and/or the transcript level using a variety of molecules which interfere with transcription and/or translation (e.g., antisense, siRNA, Ribozyme, DNAzyme), or on the protein level using e.g., antagonists, antibodies, enzymes that cleave the polypeptide and the like. Preferably, agents which are capable of preventing the association between HIF-1α and MSF-A are suitable for use along with the present invention.

Following is a list of agents capable of downregulating expression level and/or activity of MSF-A or HIF-1α and as such are suitable for use with the method of the present invention.

One example of an agent capable of downregulating MSF-A-dependent HIF-1α activity, preventing the formation of an MSF-A-HIF-1α complex or destabilizing an already formed complex is an antibody or antibody fragment capable of specifically binding MSF-A or HIF-1α. Such an antibody can be a neutralizing antibody which binds an epitope on MSF of HIF-1α and thus inhibits MSF-A-dependent HIF-1α activity. Preferably, the antibody specifically binds at least one epitope of a MSF-A or HIF-1α. Non-limiting examples of such epitopes are set forth by SEQ ID NO:4213 or 4198. Measures are taken though, to select an epitope which will be specifically recognized by the neutralizing antibody. For example, a suitable antibody which can be used along with the present invention is an anti-MSF-A antibody or antibody fragment as described in Example 6 of the Examples section which follows, which is capable of specifically binding to the polypeptide set forth by SEQ ID NO:3.

As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three-dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference and the Material and Experimental Methods section of Example 3 in the Examples section which follows).

Antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (1972)]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946, 778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin Hones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995). It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

To prepare an intracellular antibody expression vector, the cDNA encoding the antibody light and heavy chains specific for the target protein of interest are isolated, typically from a hybridoma that secretes a monoclonal antibody specific for the marker. Hybridomas secreting anti-marker monoclonal antibodies, or recombinant monoclonal antibodies, can be prepared using methods known in the art. Once a monoclonal antibody specific for the marker protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

As is shown in FIGS. 23-27 and is described in Example 7 of the Examples section which follows, both the MSF-A and HIF-1α are co-localized in the cell nucleus. To direct the specific expression of an antibody to the cell nuclei, a nuclear localization signal coding sequence (e.g., PKKKRKV; Eguchi A, et al., 2005, J. Control Release. 104: 507-19) is preferably ligated to a nucleic acid construct encoding the antibody, preferably, downstream of the coding sequence of the antibody. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit marker activity in a cell, the expression vector encoding the intracellular antibody is introduced into the cell by standard transfection methods, as discussed hereinbefore.

Another agent capable of downregulating MSF-A-dependent HIF-α activity, or preventing the formation of an MSF-A-HIF-1α complex is a small interfering RNA (siRNA) molecule which is capable of downregulating expression of MSF-A or HIF-1α. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr. Opin. Genetics and Development 12:225-232 (2002); and Bernstein Nature 409:363-366 (2001)]. In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Cum Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the MSF-A and/or HIF-1α mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl, T. 2001, ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Suitable anti-MSF-A siRNAs can be for example the 5'-GCCUCCUGAGUAAGACUUCtt (SEQ ID NO:4194) or the 5'-CGUGCCUCCUGAGUAAGACtt (SEQ ID NO:4195) siRNA sequences.

Another agent capable of downregulating MSF-A-dependent HIF-α activity, or preventing the formation of an MSF-A-HIF-1α complex is a DNAzyme molecule capable of specifically cleaving an mRNA transcript or DNA sequence of the MSF-A and/or HIF-1α. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther. www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

Downregulation of MSF-A or HIF-1α can also be effected by using an antisense polynucleotide capable of specifically hybridizing with an mRNA transcript encoding the MSF-A and/or HIF-1α and thus preventing the association between MSF-A and HIF-1α.

Design of antisense molecules which can be used to efficiently down-regulate MSF-A or HIF-1α must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Suitable antisense oligonucleotides which can be utilized to down-regulate MSF-A or HIF-1α expression are exemplified by 5'-GCTCCCTCCAACCAGACTCA-3' (SEQ ID NO:4196) or 5'-GGGTTCTTTGCTTCTGTGTC-3' (SEQ ID NO:4197), respectively.

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating MSF-A-dependent HIF-α activity, or preventing the formation of an MSF-A-HIF-1α complex is a ribozyme molecule capable of specifically cleaving an mRNA transcript encoding MSF-A or HIF-1α. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating MSF-A-dependent HIF-1α activity, preventing the formation of an MSF-A-HIF-1α complex or destabilizing an already formed complex can be any molecule which binds to and/or cleaves MSF-A or HIF-1α (e.g., antagonists, or inhibitory peptides) or prevents MSF-A or HIF-1α activation or substrate binding. An example of such a molecule is a non-functional MSF-A polypeptide and/or a non-functional HIF-1α polypeptide.

As used herein, the phrases "non-functional MSF-A polypeptide" and/or a "non-functional HIF-1α polypeptide" refer to any polypeptide lacking at least one function of the MSF-A and/or HIF-1α polypeptides, including, but not limited to, substrate binding or interaction with other proteins. Such a polypeptide can include at least one insertion, deletion or substitution of an amino acid which results in an altered function of the MSF-A and/or the HIF-1α proteins. Non-limiting examples of non-functional MSF-A polypeptides are the N-terminal deleted form of the MSF-A protein as set forth by SEQ ID NO:10 which is encoded by SEQ ID NO:7 and/or the GTP-binding site deleted form of the MSF-A protein as set forth by SEQ ID NO:4215.

It will be appreciated that a non-functional analogue of at least a catalytic or binding portion of either MSF-A or HIF-1α can be also used to prevent the formation of the MSF-A-HIF-1α protein complex. For example, an MSF-A analogue consisting of at least one substituted, inserted or deleted amino acid at the N-terminal of MSF-A (i.e., any of the first 25 amino acids as set forth in SEQ ID NO:3) can be used to prevent MSF-A-dependent activation of HIF-1α.

Such non-functional MSF-A or HIF-1α polypeptides can be utilized per se or can be expressed in cells by ligating a polynucleotide encoding the non-functional MSF-A or HIF-1α polypeptide into an expression vector as is further described hereinbelow.

In addition to the non-functional polypeptides described above, the present invention can also employ peptides, peptide analogues or mimetics thereof which are derived from either the HIF-1α or the MSF-A and which are capable of preventing the formation of, or dissociating, the MSF-A-HIF-1α protein complex.

Such peptides, peptide analogues or mimetics thereof are preferably short amino acid sequences of at least 2 or 3 amino acids, preferably at least 4, more preferably, at least 5, more preferably, in the range of 5-30, even more preferably in the range of 5-25 amino acids which are derived from either the HIF-1α or the MSF-A proteins. A non-limiting example of such a peptide can be the 25 mer peptide derived from the unique N-terminal sequence of MSF-A (SEQ ID NO:3). The amino acid sequence of such a peptide is: Met Lys Lys Ser Tyr Ser Gly Gly Thr Arg Thr Ser Ser Gly Arg Leu Arg Arg Leu Gly Asp Ser Ser Gly Pro as set forth by SEQ ID NO:4213.

As used herein the term "mimetics" refers to molecular structures, which serve as substitutes for the peptide of the present invention in prevention of the formation of or dissociation of the MSF-A-HIF-1α protein complex (Morgan et al. (1989) Ann. Reports Med. Chem. 24:243-252 for a review of peptide mimetics). Peptide mimetics, as used herein, include synthetic structures (known and yet unknown), which may or may not contain amino acids and/or peptide bonds, but retain the structural and functional features of preventing the formation of or dissociating the HIF-1α-MSF-A protein complex. Types of amino acids which can be utilized to generate mimetics are further described hereinbelow. The term, "peptide mimetics" also includes peptoids and oligopeptoids, which are peptides or oligomers of N-substituted amino acids [Simon et al. (1972) Proc. Natl. Acad. Sci. USA 89:9367-9371]. Further included as peptide mimetics are peptide libraries, which are collections of peptides designed to be of a given amino acid length and representing all conceivable sequences of amino acids corresponding thereto. Non-limiting examples of such peptide libraries are provided in SEQ ID NOs:12-2462 or 2463-4193 for peptides derived from HIF-1α or MSF-A, respectively. Methods of producing peptide mimetics are described hereinbelow.

The term "peptide" as used herein encompasses native peptides (either degradation products, synthetically synthesized peptides or recombinant peptides) and as mentioned hereinabove, peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated bonds (—N(CH3)—CO—), ester bonds (—C(R)H—C—O—O—C(R)—N—), ketomethylen bonds (—CO—CH2—), a-aza bonds (—NH—N(R)—CO—), wherein R is any alkyl, e.g., methyl, carba bonds (—CH2—NH—), hydroxyethylene bonds (—CH(OH)—CH2—), thioamide bonds (—CS—NH—), olefinic double bonds (—CH=CH—), retro amide bonds (—NH—CO—), peptide derivatives (—N(R)—CH2—CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as Phenylglycine, TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1) and non-conventional or modified amino acids (Table 2) which can be used with the present invention.

TABLE 1

| Amino Acid | Three-Letter Abbreviation | One-letter Symbol |
|---|---|---|
| alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| glycine | Gly | G |
| Histidine | His | H |
| isoleucine | Iie | I |
| leucine | Leu | L |
| Lysine | Lys | K |
| Methionine | Met | M |
| phenylalanine | Phe | F |
| Proline | Pro | P |
| Serine | Ser | S |
| Threonine | Thr | T |
| tryptophan | Trp | W |
| tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcyclopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |

TABLE 2-continued

| Non-conventional amino acid | Code | Non-conventional amino acid | Code |
|---|---|---|---|
| D-α-methyltyrosine | Dmty | N-cyclodecylglycine | Ncdec |
| D-α-methylvaline | Dmval | N-cyclododeclglycine | Ncdod |
| D-α-methylalnine | Dnmala | N-cyclooctylglycine | Ncoct |
| D-α-methylarginine | Dnmarg | N-cyclopropylglycine | Ncpro |
| D-α-methylasparagine | Dnmasn | N-cycloundecylglycine | Ncund |
| D-α-methylasparatate | Dnmasp | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylyethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomo phenylalanine | Mhphe |
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl) carbamylmethyl-glycine | Nnbhm | N-(N-(3,3-diphenylpropyl) carbamylmethyl(1)glycine | Nnbhe |
| 1-carboxy-1-(2,2-diphenyl ethylamino)cyclopropane | Nmbc | | |

Since the present peptides are preferably utilized in therapeutics or diagnostics which require the peptides to be in soluble form, the peptides of the present invention preferably include one or more non-natural or natural polar amino acids, including but not limited to serine and threonine which are capable of increasing peptide solubility due to their hydroxyl-containing side chain.

The peptides of the present invention are preferably utilized in a linear form, although it will be appreciated that in cases where cyclicization does not severely interfere with peptide characteristics, cyclic forms of the peptide can also be utilized.

The peptides of present invention can be biochemically synthesized such as by using standard solid phase techniques. These methods include exclusive solid phase synthesis, partial solid phase synthesis methods, fragment condensation and classical solution synthesis. These methods are preferably used when the peptide is relatively short (i.e., 10 kDa)

and/or when it cannot be produced by recombinant techniques (i.e., not encoded by a nucleic acid sequence) and therefore involve different chemistry.

Solid phase peptide synthesis procedures are well known in the art and further described by John Morrow Stewart and Janis Dillaha Young, Solid Phase Peptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

In cases where large amounts of the peptides of the present invention are desired, the peptides of the present invention can be generated using recombinant techniques such as described by Bitter et al., (1987) Methods in Enzymol. 153: 516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680, Brogli et al., (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

Generation of peptide mimetics, as described hereinabove, is effected using various approaches, including, for example, display techniques, using a plurality of display vehicles (such as phages, viruses or bacteria) each displaying a short peptide sequence as described hereinabove. For example, a display library containing peptides derived from HIF-1α or MSF-A (as set forth by SEQ ID NOs:12-2462 or 2463-4193, respectively) can be screened with MSF-A or HIF-1α (respectively) in order to identify peptides capable of binding one or both constituents of this protein complex. Such peptides would be potentially capable of preventing the formation of the complex or capable of destabilizing the complex.

Methods of constructing and screening peptide display libraries are well known in the art. Such methods are described in, for example, Young A C, et al., "The three-dimensional structures of a polysaccharide binding antibody to Cryptococcus neoformans and its complex with a peptide from a phage display library: implications for the identification of peptide mimotopes" J Mol Biol 1997 Dec. 12; 274(4): 622-34; Giebel L B et al. "Screening of cyclic peptide phage libraries identifies ligands that bind streptavidin with high affinities" Biochemistry 1995 Nov. 28; 34(47):15430-5; Davies E L et al., "Selection of specific phage-display antibodies using libraries derived from chicken immunoglobulin genes" J Immunol Methods 1995 Oct. 12; 186(1):125-35; Jones C RT al. "Current trends in molecular recognition and bioseparation" J Chromatogr A 1995 Jul. 14; 707(1):3-22; Deng S J et al. "Basis for selection of improved carbohydrate-binding single-chain antibodies from synthetic gene libraries" Proc Natl Acad Sci USA 1995 May 23; 92(11):4992-6; and Deng S J et al. "Selection of antibody single-chain variable fragments with improved carbohydrate binding by phage display" J Biol Chem 1994 Apr. 1; 269(13):9533-8, which are incorporated herein by reference.

Peptide mimetics can also be uncovered using computational biology. For example, various compounds can be computationally analyzed for an ability to prevent the formation of or dissociate the MSF-A-HIF-1α protein complex using a variety of three-dimensional computational tools. Software programs useful for displaying three-dimensional structural models, such as RIBBONS (Carson, M., 1997. Methods in Enzymology 277, 25), 0 (Jones, T A. et al., 1991. Acta Crystallogr. A47, 110), DINO (DINO: Visualizing Structural Biology (2001) http://www.dino3d.org); and QUANTA, INSIGHT, SYBYL, MACROMODE, ICM, MOLMOL, RASMOL and GRASP (reviewed in Kraulis, J., 1991. Appl Crystallogr. 24, 946) can be utilized to model interactions between the MSF-A-HIF-1α protein complex and prospective peptide mimetics to thereby identify peptides which display the highest probability of binding and interfering of the association between MSF-A and HIF-1α. Computational modeling of protein-peptide interactions has been successfully used in rational drug design, for further detail, see Lam et al., 1994. Science 263, 380; Wlodawer et al., 1993. Ann Rev Biochem. 62, 543; Appelt, 1993. Perspectives in Drug Discovery and Design 1, 23; Erickson, 1993. Perspectives in Drug Discovery and Design 1, 109, and Mauro M J. et al., 2002. J Clin Oncol. 20, 325-34.

Aptamers are nucleic acids or oligonucleotide molecules, typically of 10-15 kDa in size (30-45 nucleotides) which are capable of specifically binding to selected targets and altering their activity.

Aptamers may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'—NH2), which may improve a desired property, e.g., resistance to nucleases or longer lifetime in vivo. Aptamers may be conjugated to other molecules, e.g., a high molecular weight carrier to slow the clearance of the aptamer from the circulatory system, or they can be specifically cross-linked to their cognate ligands, e.g., by photoactivation of a cross-linker (See, e.g., Brody, E. N. and L. Gold (2000) J. Biotechnol. 74:5-13.)

Aptamers are produced using in vitro selection processes which allow the specificity and affinity of the aptamer to be tightly controlled.

A suitable method for generating an aptamer to a target of interest (e.g., the MSF-A, the HIF-1α and/or the MSF-A-HIF1α complex) is the "Systematic Evolution of Ligands by EXponential Enrichment" (SELEX™). The SELEX™ method is described in U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Briefly, a mixture of nucleic acids is contacted with the target molecule under conditions favorable for binding. The unbound nucleic acids are partitioned from the bound nucleic acids, and the nucleic acid-target complexes are dissociated. Then the dissociated nucleic acids are amplified to yield a ligand-enriched mixture of nucleic acids, which is subjected to repeated cycles of binding, partitioning, dissociating and amplifying as desired to yield highly specific high affinity nucleic acid ligands to the target molecule.

Aptamers have been generated for over 100 proteins including growth factors, transcription factors, enzymes, immunoglobulins, and receptors. Typical aptamers bind to their targets with sub-nanomolar affinity and discriminate against closely related targets (i.e., other proteins from the same gene family). A series of structural studies have shown that aptamers are capable of using the same types of binding interactions (hydrogen bonding, electrostatic complementarity, hydrophobic contacts, and steric exclusion) that drive affinity and specificity in antibody-antigen complexes.

Thus, the teachings of the present invention can be used to treat cancer or cancerous tumors. Briefly, an agent capable of preventing the formation of or dissociating the MSF-A-HIF-1α protein complex such as the siRNA set forth by SEQ ID NO:4195 which is designed for downregulating the MSF-A mRNA is administered to the individual as part of a pharmaceutical composition (as described hereinbelow) along with a pharmaceutical acceptable carrier (e.g., calcium carbonate). It should be noted that since siRNA molecules typically have a limited half-life the treatment described above is preferably repeated periodically in order to prevent tumor growth or progression of cancer.

Although as described hereinabove, activation of HIF-1α through the HIF-1α-MSF-A protein complex is associated with cancerous tumors and cancer metastases, there are several clinical conditions in which activation of HIF-1α is desired. For example, in the case of acute ischemia, where the oxygen tension decreases (i.e., hypoxia conditions), HIF-1α is stabilized and thus activates transcription of various target genes which contribute to angiogenesis. However, such activation is temporary and often can not overcome and correct the damage caused by the acute ischemia.

While reducing the present invention to practice, the present inventor has uncovered that upregulation of MSF-A-dependent HIF-1α activity and/or stabilization of the MSF-A-HIF-1α protein complex can be used to activate HIF-1α and to treat acute ischemia.

Thus, according to another aspect of the present invention there is provided a method of treating acute ischemia in cells of an individual.

The method is effected by providing to the individual an agent capable of upregulating an MSF-A-dependent HIF-1α activity and/or stabilizing an MSF-A-HIF-1α protein complex in cells of the individual to thereby treat the acute ischemia.

The term "individual" as used herein encompasses both males and females at any age which are at risk to develop ischemic diseases. For example, smokers or individuals with high blood pressure, diabetes, hypercholesterolemia, a coronary disease, cerebral vascular diseases and atherosclerosis.

According to preferred embodiments of the present invention the acute ischemia is a result of stroke or acute myocardial infraction.

As used herein the term "upregulating" refers to increasing the expression level and/or activity of MSF-A and/or HIF-1α proteins.

The term "stabilizing" refers to increasing the stability of the MSF-A-HIF-1α protein complex, i.e., enabling the protein complex to retain the interactions between the MSF-A and HIF-1α which consist of the protein complex. It will be appreciated that stabilization of the MSF-A-HIF-1α protein complex can be achieved, for example, by upregulating the expression level and/or activity of the MSF-A and/or the HIF-1α proteins.

Upregulation of the expression level and/or activity of MSF-A or HIF-1α can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like). Preferably, agents capable of increasing the association between MSF-A and HIF-1α can be used along with the present invention.

Following is a list of agents capable of upregulating the expression level and/or activity of MSF-A or HIF-1α.

An agent capable of upregulating expression level of MSF-A or HIF-1α may be an exogenous polynucleotide sequence designed and constructed to express at least a functional portion of the MSF-A or HIF-1α proteins. Accordingly, the exogenous polynucleotide sequence may be a DNA or RNA sequence encoding the MSF-A or HIF-1α molecules, capable of forming the MSF-A-HIF-1α protein complex.

The phrase "functional portion" as used herein refers to part of the MSF-A or HIF-1α proteins (i.e., a polypeptide) which exhibits functional properties of the enzyme such as binding a substrate or another protein, forming a protein complex and the like. According to preferred embodiments of the present invention the functional portion of MSF-A or HIF-1α is a polypeptide sequence including amino acids 1-586 as set forth in SEQ ID NO:3 or a polypeptide sequence including amino acids 1-826 as set forth in SEQ ID NO:11, respectively. Preferably, the functional portion of HIF-1α is a polypeptide sequence including amino acids 37-373, more preferably, amino acids 36-821 as set forth in SEQ ID NO:11.

MSF-A and HIF-1α have been cloned from human, mouse (HIF-1α) and rat (HIF-1α) sources. Thus, coding sequences information for MSF-A and/or HIF-1α is available from several databases including the GenBank database available through http://www.ncbi.nlm.nih.gov/.

To express exogenous MSF-A or HIF-1α in mammalian cells, a polynucleotide sequence encoding MSF-A or HIF-1α (SEQ ID NO:1 or 2, respectively) is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of the present invention can also utilize MSF-A or HIF-1α homologues which exhibit the desired activity. Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:1 or 2, respectively, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter [Zabala M, et al., Cancer Res. 2004, 64(8): 2799-804].

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of MSF-A/or HIF-1α mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide. It will be appreciated that such an expression vector can include the coding sequence of both MSF-A and HIF-1a to enable translation of both proteins.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of MSF-A or HIF-1α since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

It will be appreciated that upregulation of MSF-A and/or HIF-1α can be also effected by administration of MSF-A and/or HIF-1α-expressing cells into the individual.

MSF-A and/or HIF-1α-expressing cells can be any suitable cells, such as cardiac cells, bone marrow and lymphocyte cells which are derived from the individuals and are transfected ex vivo with one or two expression vectors containing the polynucleotide(s) designed to express MSF-A and/or HIF-1α as described hereinabove.

Administration of the MSF-A and/or HIF-1α—expressing cells of the present invention can be effected using any suitable route such as intravenous, intra peritoneal, intra kidney, intra gastrointestinal track, subcutaneous, transcutaneous, intramuscular, intracutaneous, intrathecal, epidural and rectal. According to presently preferred embodiments, the MSF-A and/or HIF-1α—expressing cells of the present invention are introduced to the individual using intravenous, intra cardiac, intra gastrointestinal track and/or intra peritoneal administrations.

MSF-A and/or HIF-1α-expressing cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylidene-acetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 μm. Such microcapsules can be further encapsulated with additional 2-5 μm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 μm (Canaple L. et al., Improving cell encapsulation through size control. J Biomater Sci Polym Ed. 2002; 13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

An agent capable of upregulating the MSF-A or HIF-1α may also be any compound which is capable of increasing the transcription and/or translation of an endogenous DNA or mRNA encoding the MSF-A or HIF-1α and thus increasing endogenous MSF-A or HIF-1α activity, respectively.

An agent capable of upregulating the MSF-A or HIF-1α may also be an exogenous polypeptide including at least a functional portion (as described hereinabove) of the MSF-A or HIF-1α proteins.

Upregulation of MSF-A or HIF-1α can be also achieved by introducing at least one MSF-A or HIF-1α substrate or inducer. Non-limiting examples of such agents include PHD inhibitors, Capsaicin (8-methyl-N-Vanillyl-6nonenamide), DBM (dibenzoylmethane), CPX (ciclopirox olamine), Deferoxamine, Mersalyl, Chromium, $CoCl_2$ which are known to induce HIF-1α expression and/or activity (Paul et al., 2004; J. Cell Physiol. 200: 20-30).

It will be appreciated that stabilization of the MSF-A-HIF1α protein complex can be also effected using a polypeptide capable of stabilizing the MSF-A-HIF1α protein complex.

Each of the upregulating, stabilizing or downregulating agents described hereinabove or the expression vector encoding MSF-A and/or HIF-1α or portions thereof can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the upregulating, stabilizing or downregulating agent or the expression vector encoding MSF-A and/or HIF-1α which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the upregulating, stabilizing or downregulating agent or the expression vector encoding MSF-A and/or HIF-1α) effective to prevent, alleviate or ameliorate symptoms of a disorder (e.g., cancer and/or cancerous tumor or acute ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (See e.g., Fingl, et al., 1975, in "The Pharmacological Basis of Therapeutics", Ch. 1 p. 1).

Dosage amount and interval may be adjusted individually to provide plasma levels of the active ingredient are sufficient to prevent cancer and/or cancerous tumor or acute ischemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, the teachings of the present invention can be used, for example, to treat individuals suffering from acute ischemia. Thus, an expression vector (e.g., a viral vector) including a polynucleotide sequence encoding the MSF-A and/or HIF-1α mRNA (SEQ ID NO:1 and/or 2, respectively) and the suitable promoter sequences to enable expression in heart cells is introduced into the individual via intravenous administration. Expression of such a vector in the heart is expected to upregulate and stabilize the MSF-A-HIF-1α protein complex in the heart, increase HIF-1α transcriptional activity on angiogenesis target genes and thus treat the acute ischemia. Dosage of such an expression vector should be calibrated using cell culture experiments and acute ischemia animal models. Success of treatment is preferably evaluated by determining the plasma levels of Troponin, CPK and other markers of myocardial acute ischemia and the individual general health status.

It will be appreciated, that if such a treatment is employed immediately following the first signs of acute ischemia, i.e., during or immediately following a heart attack, or stroke, it may prevent the complications associated with such a condition.

The agents described hereinabove which are capable of increasing the MSF-A-dependent HIF-1α activity and/or stabilizing an MSF-A-HIF-1α protein complex can be also used in various applications in which upregulation of angiogenesis is desired.

Thus, according to another aspect of the present invention, there is provided a method of inducing angiogenesis in a tissue. The method is effected by contacting the tissue with an agent capable of upregulating an MSF-A-dependent HIF-1α activity and/or stabilizing an MSF-A-HIF-1α protein complex to thereby induce angiogenesis in the tissue.

As used herein the term "angiogenesis" refers to the formation of new blood vessels, usually by sprouting from preexisting blood vessels.

The term "tissue" refers to aggregate of cells having a similar structure and function and including blood vessels. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue and fat tissue.

The tissue according to this aspect of the present invention can be part of an organism or individual (i.e., for in vivo angiogenesis), can be taken out of the organism (e.g., for ex vivo tissue repair) or can be formed ex vivo from cells derived from the organism on a scaffold or a matrix selected suitable for tissue formation.

For example, the agents according to this aspect of the present invention which are capable of upregulating an MSF-A-dependent HIF-1α activity and/or stabilizing an MSF-A-HIF-1α protein complex can be used to induce angiogenesis of a tissue. Briefly, any of the MSF-A and/or HIF-1α upregulating agents of the present invention (e.g., the polynucleotide expressing MSF-A or HIF-1α, the MSF-A or HIF-1α polypeptide or peptide, cells expressing MSF-A or HIF-1α, the compound increasing MSF-A or HIF-1α transcription, translation or stability and/or the MSF-A or HIF-1α substrate) can be provided to a tissue to thereby activate HIF-1α activity and induce angiogenesis.

Thus, the method and agents (which are capable of increasing the MSF-A-dependent HIF-1α activity) according to this aspect of the present invention can be used in vitro, to form a tissue model, ex vivo, for tissue regeneration and/or repair and in vivo for tissue regeneration and/or repair in various clinical conditions such as infarcted heart, brain lesion, spinal cord injury, ischemia and the like.

According to preferred embodiments of this aspect of the present invention, the MSF-A and/or HIF-1α upregulating agents can be attached to, added to or impregnated within a scaffold designed to enable cell growth, angiogenesis and tissue formation. Such a scaffold can be any synthetic or biodegradable scaffold known in the arts. Non-limiting examples of scaffolds which can be used to induce angiogenesis along with the agents of the present invention include the bioengineered polyglycolic acid cloth (PGAC) described in Fukuhara S., et al. (Circ. J. 69:850-7, 2005), hyaluronic acid (HA) hydrogels (Hou S, et al., 2005, J. Neurosci. Methods. June 21; Epub ahead of print), fibrin gel (Royce S M, et al., 2004, J. Biomater. Sci. Polym. Ed. 15(10): 1327-36) and the like.

The present invention also envisages identification of other anti cancer agents which are capable of preventing the formation of or dissociating the MSF-A-HIF-1α protein complex and as such may be used as anti cancer drugs.

Thus, according to another aspect of the present invention there is provided a method of identifying putative anti cancer agents.

As used herein, the phrase "anti cancer agents" refers to chemicals, antibodies, aptamers, peptides and the like which can be used to treat and prevent the growth of cancerous cells or cancerous tumors.

The method is effected by identifying agents which are capable of downregulating an MSF-A dependent HIF-1α activity, preventing the formation of or dissociating the MSF-A-HIF-1α protein complex to thereby identify the putative anti cancer agents.

As is shown in Example 1 of the Examples section which follows an MSF-A-HIF-1α protein complex used for identifying such agents (i.e., the pre-established complex) can be formed in vitro by co-transfection of cells with expression vectors containing the MSF-A (SEQ ID NO:1) and HIF-1α (SEQ ID NO:2) coding sequences.

Alternatively, peptides, which encompass the interaction site of either of the proteins may be used to generate the MSF-A-HIF-1α protein complex of this aspect of the present invention. For example, a peptide which is derived from the N-terminal part of the MSF-A protein (i.e., amino acids 1-25 as set forth in SEQ ID NO:3) along with additional amino acid sequences (as needed) can be used to form the pre-established complex.

Combinatorial chemical, nucleic acid or peptide libraries may be used to screen a plurality of agents.

Screening according to this aspect of the present invention may be effected by contacting the agents with the pre-established complex described hereinabove or with either an MSF-A or an HIF-1α. The MSF-A or the HIF-1α proteins are preferably bound to a solid support to monitor binding of the agent to the MSF-A or the HIF-1α proteins or to monitor dissociation of the pre-established complex, respectively. The solid support may be any material known to those of ordinary skill in the art to which a specific antibody which can recognize the MSF-A or the HIF-1α proteins may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. Molecular immobilizion on a solid support is effected using a variety of techniques known to those in the art.

A number of methods are known in the art for determining intermolecular interactions. Examples include, but are not limited to, ELISA, Biacore, Pull-down assay, immunoprecipitation and the like (see references in the Examples section which follows).

A competitive assay in which at least one of the assay component is labeled may also be employed. Labeling methods and tags are described in the references incorporated to the Examples section which follows.

It will be appreciated that when utilized along with automated equipment, the above-described method can be used to screen multiple agents both rapidly and easily.

Agents identified using the above-described methodology can be further qualified by functional assays, such as by inhibiting the transcriptional activity of a reporter gene (e.g., luciferase) as described in Example 2 of the Examples section which follows.

As is shown in FIGS. 6a-d, an immunoprecipitation experiment followed by an immunoblotting experiment demonstrated that an N-terminal truncated form of MSF-A is unable to form a protein complex with HIF-1α.

Thus, the present invention further provides a method of determining if a molecule is capable of preventing the formation of and/or dissociating an MSF-A-HIF-1α protein complex.

The method is effected by incubating the MSF-A-HIF-1α protein complex or cells harboring the MSF-A-HIF-1α protein complex with the molecule (for example, any one of the peptides set forth by SEQ ID Nos:12-4193 and 4213) and determining the presence, absence or level (amount of complexed vs. uncomplexed proteins) of the MSF-A-HIF-1α protein complex following such incubation. It will be appreciated that absence of the MSF-A-HIF-1α protein complex is indicative of the capacity of the molecule to prevent the formation of and/or dissociate the MSF-A-HIF-1α protein complex.

As is shown in the Examples section which follows, the incubation time used by the present invention to detect the presence or absence of the MSF-A-HIF-1α protein complex was in most cases 24-48 hours following transfection, or 24 hours following subjecting the cells to hypoxia or normoxia.

Thus, according to preferred embodiments incubating is effected for a time period selected from the range of 1-48 hours, more preferably, for a time period of 1-24 hours, most preferably, 1-12 hours.

The term "determining" as used herein with regard to the presence or absence of the protein complex, refers to the detection, identification or isolation of the protein complex (i.e., via immunoprecipitation and affinity columns) and the determination of the presence of both proteins (i.e., MSF-A and HIF-1α) within such a protein complex using e.g., an immunological detection method as is shown in FIGS. 3a-f and the Examples section which follows.

Immunological detection methods: The immunological detection methods used in context of the present invention are fully explained in, for example, "Using Antibodies: A Laboratory Manual" [Ed Harlow, David Lane eds., Cold Spring Harbor Laboratory Press (1999)] and those familiar with the art will be capable of implementing the various techniques summarized hereinbelow as part of the present invention. All of the immunological techniques require antibodies specific to both MSF-A and HIF-1α proteins. Such antibodies can be obtained from any commercial supplier of molecular biology reagents such as Gibco-Invitrogen Corporation (Grand Island, N.Y. USA), Sigma (St. Louis Mo., USA), Santa Cruz (Biotechnology, Inc., Santa Cruz, Calif., USA), Roche (Indianapolis, Ind., USA) and/or by using the MSF-A antibody of the present invention Immunological detection methods suited for use as part of the present invention include, but are not limited to, radio-immunoassay (RIA), enzyme linked immunosorbent assay (ELISA), western blot, immunohistochemical analysis, and fluorescence activated cell sorting (FACS).

Radio-immunoassay (RIA): In one version, this method involves precipitation of the desired substrate, HIF-1α or MSF-A in this case and in the methods detailed hereinbelow, with a specific antibody and radiolabelled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabelled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Immunohistochemical analysis: This method involves detection of a substrate in situ in fixed cells by substrate specific antibodies. The substrate specific antibodies may be enzyme linked or linked to fluorophores. Detection is by microscopy and subjective evaluation. If enzyme linked antibodies are employed, a colorimetric reaction may be required. It will be appreciated that the presence of the MSF-A-HIF-1α complex can be detected in cells by double-labeling immunofluorescence as described in Example 3 of the Examples section which follows.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

According to preferred embodiments of the present invention determination of the presence or absence of the MSF-A-HIF-1α protein complex is effected by sequentially and/or simultaneously exposing the protein complex or cells expressing the protein complex to an anti-MSF-A and anti-HIF-1α antibodies.

As used herein the term "sequentially" refers the use of one antibody in one immunological detection method (i.e., immunoprecipitation or affinity column) and the use of the second antibody in the other immunological detection method (i.e., Western Blot, Eliza, FACS and the like). See for further details the methodology described in the Examples section which follows.

Figure 12A:
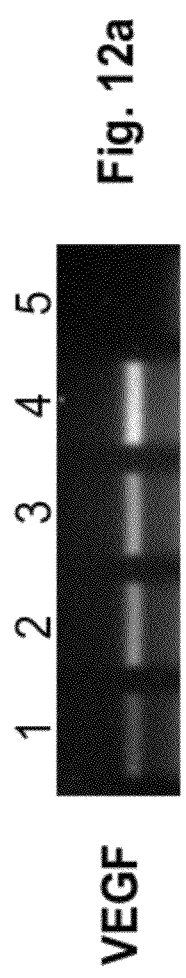
Figure 12B:
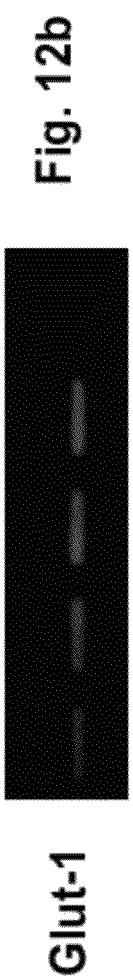
Figure 12C:

The term "simultaneously" as used herein refers to the use of both antibodies by the same time, using for example, double immunohistochemistry (see FIGS. 12a-c and Example 3 of the Examples section which follows).

As is mentioned before, the association of MSF-A with the HIF-1α protein upregulates HIF-1α transcriptional activity (see Example 2 of the Examples section which follows). In addition, HIF-1α over-expression is associated with a failure of anti cancer therapy [Escuin, 2004 (Supra)].

Thus, the present invention also contemplates a method of determining the prognosis of an individual having cancer.

The method is effected by determining the presence or absence of an MSF-A-HIF-1α protein complex in cancerous cells derived from the individual, wherein the presence of such a protein complex is indicative of poor prognosis of the individual.

As used herein "prognosis" refers to the probable outcome or course of a disease; the chance of recovery. Thus, individuals with poor prognosis have less chances of recovery than individuals with good prognosis.

It will be appreciated that individuals in which the MSF-A-HIF-1α protein complex is detected have relatively poor prognosis as compared with individuals lacking such a protein complex.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Experimental Methods

Metabolic labeling of PC-3 cells—Metabolic labeling of PC-3 cells was performed using [$^{35}$S] methionine (ICN Biomedicals, Inc., CA) essentially as described in Mabjeesh, N. J. et al. (Geldanamycin induces degradation of hypoxia-inducible factor 1 alpha protein via the proteasome pathway in prostate cancer cells. Cancer Res., 62: 2478-2482, 2002).

Preparation of whole cell lysates—Cells were washed twice with ice-cold PBS, harvested whole cell extracts (WCE) were prepared by lysing the cells with 100 mM potassium phosphate (pH 7.8) and 0.2% Triton X-100 supplemented with protease and phosphatase inhibitors as described elsewhere (Mabjeesh N J et al. 2ME2 inhibits tumor growth and angiogenesis by disrupting microtubules and dysregulating HIF. *Cancer Cell* 2003; 3: 363-375).

Immunoblotting—Proteins (30-60 µg/lane) from WCEs were resolved by 7.5% SDS-PAGE, electro-blotted to nitrocellulose membranes and incubated with the indicated primary antibodies, followed by horseradish peroxidase-conjugated secondary antiserum (Amersham Biosciences, Piscataway, N.J.). Immunoreactivity was visualized by Amersham enhanced chemiluminescence reagent (Amersham Biosciences, Piscataway, N.J.). For sequential blotting with additional antibodies, the membranes were stripped from the first primary antibody using a restore Western blot stripping buffer (Pierce, Rockford, Ill.) and were re-probed using the second primary antibody as indicated.

Immunoprecipitation—Cells were washed twice with ice-cold PBS, lysed in 20 mM Na-HEPES, pH 7.5, 0.5% Nonidet P-40, 0.1M NaCl, 2 mM EDTA, 10% Glycerol and 2 mM DTT supplemented with protease and phosphatase inhibitors, and were subjected to immunoprecipitation using anti-HIF-1α antibody and protein G-agarose beads (Pierce, Ill.) according to the manufacturer's instructions.

Construction of the p3xFlag-HIF-1α vector—HIF-1α cDNA (GenBank accession No. NM_001530; SEQ ID NO:2) was subcloned at NotI/XbaI sites of the p3XFLAG-myc-CMV-25 vector (Sigma-Aldrich Corp., St Louis, Mo., USA) to provide Flag-tagged HIF-1α at its N-terminal using the following PCR primers: forward 5'-acgtgeggccgcgatg-gagggcgccggcggcgcgaacg-3' (SEQ ID NO:8) and reverse 5'-cagttctagattatcagttaacttgatccaaagctctgag-3' (SEQ ID NO:9).

Construction of the pcDNA3.1-HIF-1α expression vector—HIF-1α cDNA was cut from the p3xFlag-HIF-1α vector at the NotI/XbaI sites and pasted to the pcDNA3.1(+) expression vector (Invitrogen Life Technologies, Carlsbad, Calif.) to obtain the untagged HIF-1α wild-type.

Construction of the MSF-A expression vector (p3xFLAG-MSF-A)—Total RNA prepared from PC-3 cells was subjected to an RT-PCR reaction using the forward [5'-GAC-TAAGCTTATGAAGAAGTCTTACTCAGGAGGCACGC-GG-ACC-3' (SEQ ID NO:4)] and reverse [5'-ACGTTCTA-GATTACTA-CATCTCTGGGGCTTCTGGCTCCTTCTC-CTCC-3' (SEQ ID NO:5)] PCR primers designed according to MSF-A cDNA sequence (GenBank Accession No AF189713, SEQ ID NO:1). The resultant MSF-A cDNA was subcloned into the p3xFLAG-myc-CMV-25 (Sigma-Aldrich Corp., St Louis, Mo., USA) at HindIII/XbaI sites to provide the FLAG sequence at the amino terminal of the recombinant protein. The sequence of the cloned MSF-A vector was validated by sequence analysis.

Construction of ΔN-MSF-A expression vector (p3xFlag-ΔN-MSF-A)—The p3xFLAG-MSF-A vector was subjected to PCR using the forward [5'-GACAAGCTTGCCT-TGAAAAGATCTTTTGAGGTC-3' (SEQ ID NO:6)] and reverse (SEQ ID NO:5)] PCR primers and the resultant N-terminal truncated MSF-A cDNA (ΔN-MSF-A; deletion of the first 25 amino acids, SEQ ID NO:7) was subcloned into the p3xFLAG-myc-CMV-25 at the HindIII/XbaI sites.

Construction of ΔG-MSF-A expression vector (p3XFlag-ΔG-MSF-A)—The MSF-A mutant lacking the GTP binding domain [ΔG; deletion of amino acids GQSGLGKS (SEQ ID NO:4198) which correspond to amino acids 305-312 as set forth by SEQ ID NO:3] was generated by two PCR reactions using the vector containing the wild-type MSF-A (p3xFLAG-MSF-A) as a template. In the first PCR reaction, the forward 5'-GACTAAGCTTATGAAGAAGTCTTACT-CAGGAGGCACGCGGACC-3' (SEQ ID NO:4) primer corresponding to the N-terminal and an internal reverse primer 5'-TGGATTTGAAGAGGGTGTTGATTAAGGT-GACCACCATGATGTTGAACTCG AAGCCC-3' (SEQ ID NO:4199) lacking 24 nucleotides corresponding to the GTP binding sequence (SEQ ID NO:4198). In the second reaction, the antisense sequence of SEQ ID NO:4199 was used as a forward internal primer 5'-GGGCTTCGAGTTCAACAT-CATGGTGGTCACCTTAATCAACACCCTCTTCAA ATCCA-3' (SEQ ID NO:4216) and the reverse primer was 5'-ACGTTCTAGATTACTA-CATCTCTGGGGCTTCTGGCTCCTTCTCCTCC-3' (SEQ ID NO:5) corresponding to the C-terminus of MSF-A. The overlapping two PCR products were used as a template to obtain the full-length of ΔG mutant of MSF-A using the external primers (SEQ ID NOs:4 and 5). The product was subcloned into p3XFlag-myc-CMV-25 vector at the HindIII and XbaI sites.

Stable transfection—PC-3 cell were seeded at 50% confluence in 100 mm-diameter dishes and grown in complete medium for overnight. Transfections were carried out with p3XFlag-CMV-myc-25 which includes a neomycin-resistance gene. Cells were transiently transfected with either the empty vector (EV; p3xFLAG-myc-CMV-25) or the vector carrying MSF-A (p3xFLAG-MSF-A). After 48 hours, the medium was replaced with fresh medium supplemented with 1 gr/ml of neomycin (G418; Sigma-Aldrich Co., Saint Louis, Mo.) and was changed every 3 days. Two to three weeks later, neomycin-resistant colonies were isolated and grown in medium supplemented with 500 mg/ml of neomycin. Cells were screened for Flag-MSF-A expression by Western blotting. To avoid clonal variation of the stably-transfected cells, 30 neomycin resistant clones of PC-3 stably transfected with the empty vector were pooled together and designated "PC-3-Neo" and 30 resistant clones stably-transfected with MSF-A were pooled together and designated as "PC-3-MSF-A".

Reporter gene assay and luminescence measurements—HRE-dependent luciferase activity was performed using the pBI-GL construct (pBI-GL V6L) containing six tandem copies of the VEGF hypoxia response element as previously described (Mabjeesh et al., 2002; Post and Van Meir, 2001). Cells were grown in E-well plates and then transiently transfected in triplicate with a total of 1 µg DNA including 0.1 µg of the reporter plasmid, pBI-GL V6L. Duplicate sets of transfected cell-culture plates were then separated and incubated for 16 hours under either normoxic or hypoxic conditions. Luciferase enzymatic activity was measured using the commercial kit TROPIX (Bedford, Mass.) in the Galaxy luminometer (BMG Labtechnologies LUMIstar) following the manufacturer's instructions. Arbitrary Luciferase activity units were normalized to the amount of protein in each assay point.

Isolation and analysis of RNA—Total RNA was extracted from cells by using RNeasy Mini Kit (Qiagen Inc., Valencia, Calif.) according to the manufacturer's protocol. Total RNA from xenograft-derived tumors, which were frozen in liquid $N_2$ immediately after dissection, was prepared using TRI REAGENT (Sigma-Aldrich Co., Saint Louis, Mo.) following the manufacturer's instructions. One µg total RNA was reverse transcribed into cDNA using Reverse-iT $1^{st}$ Strand Synthesis Kit (ABgene, Epsom, United Kingdom) using anchored oligo dT as first strand primer. PCR was performed in 25 μl reaction mixture using ReddyMix PCR master mix (ABgene, Epsom, United Kingdom) with 0.3 μM of each primer and 50 ng template. Semi-quantitative RT-PCR was performed using β-actin as an internal control to normalize gene expression for the PCR templates. PCR cycle number was optimized for each primer set. Representative samples were run at different cycle numbers and the optimal cycle number was selected in the region of linearity between cycle number and PCR product intensity. Sequences of the PCR primers, number of cycles, annealing temperature and product size for each gene were as follow:

VEGF (GenBank Accession No. NM_00376): forward primer 5'-tcttcaagccatcctgtgtg-3' (SEQ ID NO:4200), reverse primer 5'-tctctcctatgtgctggcct-3' (SEQ ID NO:4201), 22 cycles, annealing temperature 57° C., 144 by PCR product.

HIF-1α (GenBank Accession No. NM_001530): forward primer 5'-ggacaagtcaccacaggaca-3' (SEQ ID NO:4202), reverse primer 5'-gggagaaaatcaagtcgtgc-3' (SEQ ID NO:4203), 25 cycles, annealing temperature 56° C., 169 by PCR product.

β-actin (GenBank Accession No. NM_001101): forward primer 5'-ctcctgagcgcaagtactcc-3' (SEQ ID NO:4204), reverse primer 5'-ctgcttgctgatccacatctg-3' (SEQ ID NO:4205), 17 cycles, annealing temperature 55° C., 86 by PCR product.

ET-1 (GenBank Accession No. NM_001955): forward primer 5'-ccatgagaaacagcgtcaaa-3' (SEQ ID NO:4206), reverse primer 5'-agtcaggaaccagcagagga-3' (SEQ ID NO:4207), 22 cycles, annealing temperature 57° C., 213 by PCR product.

CA-IX (GenBank Accession No. NM_001216): forward primer 5'-caaagaaggggatgaccaga-3' (SEQ ID NO:4208), reverse primer 5'-gaagtcagagggcaggagtg-3' (SEQ ID NO:4209), 26 cycles, annealing temperature 57° C., 568 by PCR product.

Glut-1 (GenBank Accession No. NM_006516): forward primer 5'-gggcatgtgcttccagtatgt-3' (SEQ ID NO:4210), reverse primer 5'-accaggagcacagtgaagat-3' (SEQ ID NO:4211), 33 cycles, annealing temperature 57° C., 72 by PCR product.

MSF-A (GenBank Accession No. AF189713): forward primer (SEQ ID NO:4), reverse primer (SEQ ID NO:5 or 4199), 22 cycles, annealing temperature 55° C., PCR products of 1761 by or 940 bp, respectively.

The PCR products were visualized by UV illumination following electrophoresis through 2% agarose containing 0.5 μg/ml ethidium bromide at 50 V for 1 hour.

HIF-1α protein stability assays—Cells were plated into 6-well plates and grown to 70% confluence. The cells were subjected to either cycloheximide (CHX) treatment or to metabolic labeling and pulse chase assay. CHX was added to the cells at a final concentration of 10 μg/ml for the indicated time in the FIGS. 16a-c. Subsequently, the cells were washed and harvested for immunoblotting. Cells were metabolically labeled as previously described (Mabjeesh, N. J., et al., 2002, Cancer Res 62: 2478-2482). Briefly, the medium was changed to methionine- and cysteine-free as well as serum-free RPMI 1640 medium for 2 hours, following which the cells were labeled by incubation with methionine- and cysteine-free medium containing $^{35}$S-methionine (Amersham Biosciences Corp., Piscataway, N.J.) at a final concentration of 100 μCi/well at 37° C. for 1.5 hours. Subsequently, the radioactive medium was removed and cells were re-cultured in complete medium for the indicated times. The cells were washed twice with ice-cold PBS, lysed, and subjected to immunoprecipitation using the anti-HIF-1α antibody Immunoprecipitates were analyzed on SDS-PAGE and visualized by autoradiography.

Immunohistochemistry with anti-CD34 and anti-Ki67—For immunohistochemical staining paraffin-embedded tissue was sectioned at 3 μm and mounted on Superfrost/plus slides (Menzel-Glaser, Braunschweig, Germany). Sections were processed by a labeled-(strept)-avidin-biotin (LAB-SA) method using a Histostain Plus Kit (Zymed, San Francisco, Calif.) and following exactly the manufacturer's instructions. Sections were pre-treated for 12 minutes at 97° C. with the Target Retrieval buffer (Zymed, San Francisco, Calif.) at pH 6.0 using a temperature-controlled microwave (H2800 model processor, Energy Beam Sciences Inc., Apawa, Mass.). The sections were treated with 3% $H_2O_2$ for 5 minutes, followed by 10 minutes incubation with the universal blocker, Cas-Block (Zymed, San Francisco, Calif.). After blocking, sections were incubated for 30 minutes at room temperature with anti-CD34 (at a 1:50 dilution) or anti-Ki67 (at a 1:25 dilution). Slides were then washed with the TNT wash buffer (NEN, CITY, COUNTRY) and incubated for 30 minutes with species-specific biotinylated secondary antibody (1:200 dilution, Vector Laboratories, Burlingame, Calif.). A biotinylated secondary antibody was applied for 10 minutes, followed by a 10-minute incubation with peroxidase conjugated streptavidin (HRP-SA). The slides were thoroughly washed after each incubation using the Optimamax wash buffer (Biogenex, San Roman, Calif.). The immunoreaction was visualized by an HRP-based chromogen (Substrate System) including diamino-benzidine brown chromogene (Liquid DAB Substrate Kit, Zymed). The sections were then counterstained with Mayen's hematoxylin dehydrated in ascending ethanol concentration, cleared in xylene and mounted for microscopic examination. For negative controls, the exact procedure was done with the omission of either the primary or the secondary antibody. For quantitative analysis of Ki67 and CD34 staining, positive staining cells and microvessels were counted and their density expressed as the number of positive cells per total number of cells or capillaries per total section area excluding necrotic areas, respectively.

Production of sequence-directed antibodies against MSF-A protein—A peptide of 15 amino acids corresponding to the amino terminal part of MSF-A protein (amino acids 3-17; KSYSGGTRTSSGRLR; SEQ ID NO:4212) was synthesized, conjugated to a carrier protein and injected into rabbits (Convance Research Products Inc., Denver, Pa.). The sequence of the peptide was selected from the region that is not homologous to any other member within the overall septin family. The sera drawn from the rabbits were tested for MSF-A immunoreactivity using IP and Western blotting.

Immunofluorescence and confocal microscopy—Exponentially growing cells were plated on 12-mm glass coverslips (Fisher Scientific, Pittsburgh, Pa.) into 24-well plates and cells were allowed to attach overnight. The following day, cells were subjected to hypoxia for 16 hours. Cells were fixed for 10 minutes at room temperature with the PHEMO buffer (PIPES 0.068 M, HEPES 0.025 M, EGTA 0.015 M, $MgCl_2$ 0.003 M, 10% DMSO, pH 6.8) containing 3.7% formaldehyde, 0.05% glutaraldehyde, 0.5% Triton X-100. Coverslips were blocked for 10 minutes in 10% goat serum/PBS and processed for double-labeling immunofluorescence with monoclonal mouse anti-HIF-1α, and polyclonal rabbit anti-MSF-A antibodies. The secondary antibodies were Alexa Fluor 488 goat anti-mouse antibody and Rhodamine Red-X goat anti-rabbit antibodies. Coverslips were then mounted onto glass slides and examined with a Zeiss axioplasm laser scanning confocal microscope using a Zeiss×100 1.3 oil-immersion objective.

In vitro Proliferation Assays

Cell proliferation assay with XTT reagent—For cell proliferation assay, PC-3-Neo and PC-3-MSF-A cells were seeded in 96 well-plates (1000 cells/well in 200 µl) using a 3-bis-(2-methoxy-4-nitro-5 sulfenyl)-(2H)-tetrazolium-5-carboxanilide (XTT) kit (Biological Industries Ltd. Kibbutz Beit Haemek, Israel). Wells filled with media served as a control. On the next day, the cells were cultured either under normoxic or hypoxic conditions. XTT reagent was added at days 0, 2, 4 and 6 following the manufacturer's instructions. The absorbance of the samples was measured using a microplate reader at a wavelength of 450 nm using Elisa reader 680 (Bio-rad, Hercules, Calif.). All experiments were performed in triplicate.

Plating Efficiency assay—PC-3-Neo and PC-3-MSF-A cells were cultured in 100 mm-diameter plate (1000 cells/plate) and incubated to allow colony formation. The cultures were monitored on a daily basis and when colonies were visible (approximately after 2 weeks) cells were fixed and stained with 90% EtOH, 5% Acetic acid, 0.01% Coomassie brilliant blue (Sigma-Aldrich, Saint Louis, Mo.). Plating was done in triplicates. Colonies containing ≥20 cells were counted. Plating efficiency (%) was calculated as number of colonies formed/number of cells plated×100.

Soft Agar Foci assay—The assay tests the anchorage-independent growth of the cell in soft agar. Suspensions of PC-3-Neo or PC-3-MSF-A cells in 0.22% soft agar were poured on 35 mm-diameter plate (5000 cells/plate) pre-cast with 0.5% soft agar and were cultured for 4 weeks. Colonies (≥20 cells) were counted.

Tumor models and immunohistochemistry—PC-3-Neo or PC-3-MSF-A cells ($3 \times 10^6$) were subcutaneously (s.c.) injected into the right hinds of CD1/nude mice. All procedures were performed in compliance with the Tel Aviv Sourasky Medical Center Animal Care and Use Committee and NIH guidelines. Animals were monitored for tumor development twice a week. Tumor parameters were measured with calipers, and tumor volume was calculated according to the formula: tumor volume=width$^2$×length×0.52. After 6 weeks, animals were sacrificed and tumors were excised as quickly as possible, weighed and cut into 2 pieces. One piece of tumor was fixed with 4% buffered formalin for 24 hours, embedded in Paraplast (Oxford Labware, St. Louis, Mo., USA) until immunohistochemical staining and the second piece of the tumor was immediately frozen in liquid $N_2$ and kept at −80° C. for RNA analysis.

Tumor array and dot blot analysis—An MSF-A cDNA [HindIII/EcoRI; SEQ ID NO:4214 (nucleotides 1-721 of SEQ ID NO:1)] was labeled with $\alpha^{32}$P-dCTP (Qiagen Inc., Valencia, Calif.) and used to probe the Human Matched Tumor/Normal Expression Array from Clontech Cat. #7840-1 (Mountain View, Calif.) under high stringency conditions following the instructions of the manufacturer. Washed filters were exposed to autoradiographic films. For normalization, the membrane was stripped and re-probed with a labeled β-actin probe (Ambion, Austin, Tex., USA). Dots densities were analyzed using densitometry and each MSF-A dot was normalized to its corresponding β-actin dot. The ratio between tumoral and normal expression of each pair was then calculated.

Data analysis—Experiments presented in all Figures of the present invention are representative of three or more different repetitions. Quantification of band densities was performed using the public domain NIH Image (version 1.61). Statistical analysis was performed using a one-way ANOVA test ($p<0.05$ was considered statistically significant).

Example 1

MSF-A Associates with HIF-1 Alpha In Vitro and In Vivo

Prostate cancer cells (PC-3) express increased levels of HIF-1α protein under normoxic conditions (Zhong H et al. Increased expression of hypoxia inducible factor-1alpha in rat and human prostate cancer. Cancer Res 1998; 58: 5280-5284). To identify proteins, which regulate HIF-1 transcriptional activity under aerobic/normoxic conditions, PC-3 cells were used in a set of immunoprecipitation (IP) and immunoblotting (IB) analyses, as follows.

Experimental Results

Figure 1:
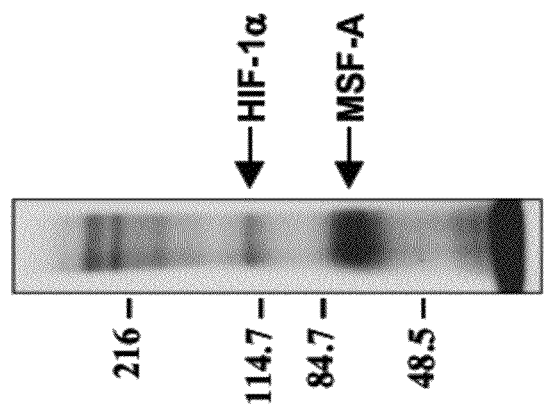

MSF-A co-immunoprecipitated with HIF-1α—PC-3 cells were metabolically labeled with [$^{35}$S]-methionine and whole cell lysates were subjected to immunoprecipitation using a purified mouse monoclonal anti-HIF-1α antibody (BD Transduction Laboratories, Lexington, Ky.). The immunoprecipitated proteins were analyzed on an SDS-PAGE and were visualized by autoradiography. As is shown in FIG. 1, several protein bands were detected in the immunoprecipitate protein mixture. Of these proteins, a 70 kDa protein, displayed a strong band signal (FIG. 1), suggesting strong association with the HIF-1α protein. Another relatively strong band, of 120 kDa, corresponded to the HIF-1α protein. To determine the identity of the 70-kDa protein, a larger scale of a non-radioactive PC-3 cell preparation was subjected to silver staining, following which the 70-kDa band was eluted and its amino acid sequence was analyzed using MALDI-TOF-MS. The protein was identified as a myeloid/lymphoid leukemia septin-like fusion protein A (MSF-A, GenBank Accession No. AAF23374, SEQ ID NO:3). This septin-like protein was first identified as part of a fusion protein with MLL in a therapy-induced acute myeloid leukemia patient [Osaka M, Rowley J D, Zeleznik-Le N J. MSF (MLL septin-like fusion), a fusion partner gene of MLL, in a therapy-related acute myeloid leukemia with a t(11;17)(q23;q25). Proc Natl Acad Sci USA 1999; 96: 6428-6433]. The exact function and cellular localization of MSF-A protein have not been elucidated. Recent studies suggested novel functions for septins in vesicle trafficking, cytokenesis and oncogenesis (Kartmann B, Roth D. Novel roles for mammalian septins: from vesicle trafficking to oncogenesis. J Cell Sci 2001; 114: 839-844).

Figure 2:
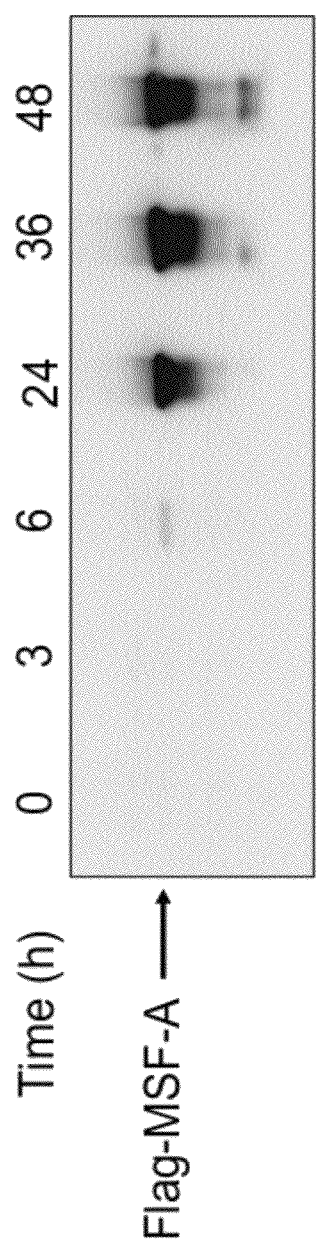

Confirmation of MSF-A/HIF-1α interaction—Since the MSF-A protein has not been previously characterized, antibodies capable of recognizing this protein have not been available prior to the present study. In order to confirm the interaction between MSF-A and HIF-1α, an in vitro system comprising of co-transfected cells was established. In a preliminary experiment, PC-3 or HEK 293 cells were transiently transfected with the p3xFlag-MSF-A expression vector and cell lysates of transfected cells were subjected to Western Blot analysis using an anti-Flag antibody (Sigma-Aldrich Corp., St Louis, Mo., USA). As is shown in FIG. 2, a time-dependent expression of the recombinant 70-kDa FLAG-tagged protein was observed.

To confirm the interaction between the HIF-1α and the MSF-A proteins, HEK 293 cells were transiently co-transfected with the p3xFlag-MSF-A and the pcDNA3.1-HIF-1α vectors, and were grown for 24 hours under normoxic conditions (i.e., conditions of 20% oxygen), following which whole cell extracts (WCE) were subjected to co-immunoprecipitation (IP) using anti-FLAG or anti-HIF-1α antibodies.

Following IP, the proteins were subjected to SDS-PAGE and immunoblotting (IB) using the counterpart antibody. As is shown in FIGS. 3a-d, following transfection with both expression vectors (i.e., pcDNA3.1-HIF-1α and p3xFlag-MSF-A) immunoprecipitates generated using either the anti-HIF-1α antibody or the anti-Flag antibody included the reciprocal proteins, i.e., the Flag-MSF-A or HIF-1α proteins, respectively. These findings clearly demonstrate a strong association between the two recombinant proteins (i.e., MSF-A and HIF-1α) in vitro. On the other hand, as is further shown in FIGS. 3e-f, the Flag antibody (which represents the MSF-A protein) failed to co-immunoprecipitate HIF-1β protein.

To further confirm the HIF-1α/MSF-A interaction, HEK 293 cells were transiently co-transfected with both the p3xFlag-MSF-A and p3xFlag-HIF-1α vectors. Twenty-four hours following transfection, cells were grown under normoxia (i.e., 20% oxygen) or hypoxia (i.e., 1% oxygen) for additional 24 hours, following which anti-HIF-1α antibody was used in IP experiments. IP samples were further subjected to Western Blot analysis using either anti-HIF-1α antibody or anti-Flag antibody. As is shown in FIGS. 4a-b, the anti-HIF-1α antibody was capable of precipitating both Flag-HIF-1α and Flag-MSF-A proteins under normoxia conditions, and to a lesser extent under hypoxia conditions.

The p300 co-activator is associated with HIF-1α and MSF-A proteins—To test the hypothesis that proteins, which are known to interact with the HIF-1α protein, such as the co-activator p300, are associated with MSF-A and HIF-1α, cells were co-transfected with the pcDNA3.1-HIF-1α and the p3xFlag-MSF-A expression vectors and IP experiments were performed using either anti-FLAG or anti-HIF-1α antibodies. As shown in FIGS. 5a-c, while the anti-HIF-1α antibody was capable of precipitating the p300 protein in both cells co-transfected with the pcDNA3.1-HIF-1α and the p3xFlag-cmv-25 expression vector alone and cells co-transfected with the pcDNA3.1-HIF-1α and the p3xFlag-MSF-A vectors, the anti-Flag antibody was capable of precipitating the p300 protein only in cells that were co-transfected with the pcDNA3.1-HIF-1α and the p3xFlag-MSF-A vectors. These results demonstrate that the MSF-A protein interacts with the HIF-1α protein complex.

Altogether, these results demonstrate that MSF-A strongly associates with HIF-1α or HIF-1α complexes.

Example 2

MSF-A Upregulates HIF-1 Transcriptional Activity

To investigate the effect of MSF-A binding on HIF-1α function, the transcriptional activity of the HIF-1 complex was determined using a reporter gene assay as previously described (Mabjeesh N J et al. 2ME2 inhibits tumor growth and angiogenesis by disrupting microtubules and dysregulating HIF. Cancer Cell 2003; 3: 363-375).

Experimental Results

MSF-A overexpression upregulates HIF-1 transcriptional activity—The effect of MSF-A on HIF-1α transcriptional activity was determined in PC-3 cells which were transiently co-transfected with a reporter plasmid containing the luciferase gene under the control of hypoxia response element (HRE) from the VEGF promoter (Post, D. E. and Van Meir, E. G. Generation of bidirectional hypoxia/HIF-responsive expression vectors to target gene expression to hypoxic cells. Gene Ther., 8: 1801-1807, 2001) and with either the p3xFlag-MSF-A vector or the expression vector alone (p3xFlag-cmv-25). Following transfection, cells were grown under normoxia or exposed to hypoxia. In cells co-transfected with the luciferase reporter plasmid and the expression vector alone, hypoxia induced luciferase activity by more than 15-fold as compared to normoxia. However, in cells co-transfected with the luciferase reporter plasmid and the MSF-A vector (p3xFlag-MSF-A), hypoxia induced luciferase activity by 50-fold as compared to normoxia (FIG. 6). Similar results were obtained when HEK 293 cells were transfected with the same vectors (not shown).

These results demonstrate that MSF-A over-expression enhances HIF-1 transcriptional activity on target genes containing the HRE sequence. Thus, MSF-A upregulates the endogenous transcriptional activity of HIF-1α.

Example 3

Association of ΔN-MSF-A with HIF-1α Results in Inhibition of HIF-1α Transcriptional Activity Members of the evolutionarily conserved septin family of genes have a well-conserved GTP binding domain and possess a GTPase activity. SEPT9 has been shown to have a complex genomic architecture, such that up to 15 different isoforms are possible by the shuffling of five alternate N-termini and three alternate C-termini. The MSF-A protein exhibits sequence homology with other members of the MSF superfamily except for the first 25 amino acids at the N-terminal part (Kartmann B, Roth D. Novel roles for mammalian septins: from vesicle trafficking to oncogenesis. J Cell Sci 2001; 114: 839-844).

To investigate the role of the unique N-terminal sequence of MSF-A or the common GTP-binding domain of MSF-A in the association and the activation of HIF-1α (i.e., transcriptional activation of other genes), constructs of the ΔN-MSF-A (lacking the N-terminus) and ΔG-MSF-A (lacking the GTP binding site) were prepared and transiently expressed in cells.

Experimental Results

The activation of HIF-1α by MSF-A is dependent on the intact N-terminus of MSF-A protein and does not require the GTP binding domain—As is shown in FIG. 7, while the expression of wild-type (WT) MSF-A induced HIF-1α activity (as detected by the luciferase reporter gene), the expression of increasing amounts of the ΔN mutant of MSF-A (p3xFlag-ΔN-MSF-A) induced a dose-dependent inhibition of HIF-1α transcriptional activity.

These results demonstrate the use of the ΔN-MSF-A polypeptide (SEQ ID NO:10), or a polynucleotide encoding same (e.g., a polynucleotide set forth by SEQ On the other hand, the expression of the ΔG mutant of MSF-A had no significant effect on HIF-1α activity (FIG. 8). Further IP experiments showed that both the ΔN-MSF-A and ΔG-MSF-A protein products are capable of binding the HIF-1α protein (FIGS. 9a-c).

Altogether, these results indicate that the protein-protein association between MSF-A and HIF-1α is not sufficient to activate HIF-1α transcriptional activity and that full activation of HIF-1α by MSF-A requires both, the GTP binding site and the intact N-terminus of MSF-A.

Example 4

MSF-A Over-Expression Induces Cell Proliferation and Colony Formation

To further understand the mechanisms involved in upregulation of HIF-1α activity via the association with MSF-A and to understand the role of MSF-A in cancer cells, PC-3 cells were stably transfected with MSF-A (using the p3xFLAG-MSF-A vector) and neomycin resistant clones were obtained.

Experimental Results

MSF-A stable PC-3 transfectants express MSF-A to various extents and exhibit increase HIF-1α transcriptional activity—The expression level of both recombinant MSF-A and endogenous HIF-1α were analyzed using Western Blot analyses. As is shown in FIG. 10a, using the anti-Flag antibody various extents of expression levels were observed in the different MSF-A transfectants. In addition, the HRE-reporter gene assay showed that MSF-A stably expressing cells exhibit increased HIF-1 transcriptional activity (FIG. 10b). As an internal control, cells were co-transfected with both Rinella SV40-Luciferase and the firefly HRE-Luciferase and were subjected to dual Luciferase assay. There were no changes in Rinella SV40-Luciferase activity under hypoxia or between the different clones compared to empty vector control or parental PC-3 cells (data not shown).

MSF-A increases the expression of HIF-downstream genes—To avoid clonal variation of MSF-A over-expressing cells, 30 neomycin resistant clones from each expression vector were pooled [i.e., EV-transfected (designated PC-3 Neo) and MSF-A-transfected (PC-3-MSF-A)] and the pooled cells were tested for HIF-1 transcriptional activity. As is shown in FIG. 11, PC-3-MSF-A cells exhibited a significant increase in HIF-1 transcriptional activity (tested by the luciferase assay) as compared with PC-3-Neo cells. To further demonstrate the effect of MSF-A on HIF-1 target genes, semi-quantitative RT-PCR analyses were performed. Briefly, total RNA was prepared from both PC-3-Neo and PC-3-MSF-A pooled cells and RT-PCR was employed using specific primers for VEGF (SEQ ID NOs:4200 and 4201), HIF-1α (SEQ ID NOs:4202 and 4203), β-actin (SEQ ID NOs: 4204 and 4205), ET-1 (SEQ ID NOs:4206 and 4207), CA-IX (SEQ ID NOs:4208 and 4209) and Glut1 (SEQ ID NOs:4210- and 4211) (FIGS. 12a-f). These RT-PCR analyses demonstrated that while the HIF-1α mRNA level was unchanged in both PC-3-MSF-A and PC-3-Neo cells (FIG. 12e), the mRNA levels of the angiogenic factor VEGF were significantly higher in PC-3-MSF-A cells than in PC-3-Neo cells (FIG. 12a). Other HIF-1 target genes including Glut1 (FIG. 12b), CA-IX (FIG. 12d) and ET-1 (FIG. 12c) were also upregulated to various extents in PC-3-MSF-A cells.

MSF-A increases cell proliferation and colony formation—To test the effect of MSF-A on cell proliferation, the XTT assay was employed on PC-3-MSF-A and PC-3-Neo cells. As is shown in FIG. 13, under both normoxia and hypoxia, the proliferation rate of PC-3-MSF-A cells was higher to a greater extent than the proliferation rate of PC-3-Neo cells. In addition, when grown in soft agar, PC-3-MSF-A cells formed significantly more colonies, each exhibiting a larger size as compared with PC-3-Neo cells grown (FIGS. 14a-g). Moreover, PC-3-MSF-A cells also showed higher plating efficiency (49.3%) as compared to PC-3-Neo cells (16.8%) (p<0.001).

Altogether, these results demonstrate that stable over-expression of MSF-A in PC-3 cells enhances proliferation and upregulates HIF-1 target genes in vitro.

Example 5

MSF-A Affects HIF-1α Stabilization

To elucidate the mechanism by which MSF-A involves with HIF-1 activity, the effects of MSF-A expression on HIF-1α protein stability was examined. As shown in FIG. 12e, MSF-A expression does alter HIF-1α mRNA levels. The present inventor hypothesized that MSF-A affects HIF-1α activity by modulating HIF-1α post-transcriptional/translational events. To this end, PC-3 stably transfected cells were employed under normoxia or hypoxia and the effect on HIF-1α ubiquitination was studied.

Experimental Results

MSF-A stabilizes HIF-1α protein by preventing its ubiquitination—The hypoxic induction of HIF-1α was studied at shorter rate limiting time periods rather than at times enabling to reach steady state levels. After 4 hours of exposure to hypoxia, the levels of HIF-1α protein expressed in PC-3-MSF-A cells was significantly higher than in PC-3-Neo cells (FIG. 15a-b). As is shown in FIGS. 15a-b, the differences in HIF-1α expression levels were dependent on the time of hypoxia induction. While the level of HIF-1α was higher in PC-3-MSF-A cells after 4 hours of hypoxia, similar levels of HIF-1α were obtained in PC-3-Neo and PC-3-MSF-A cells after 8 hours of hypoxia induction (FIGS. 15a-b). Therefore, the effect of MSF-A on HIF-1α protein stability was further examined using the protein translation inhibitor cycloheximide (CHX) (FIGS. 16a-c) and a pulse-chase assay (FIGS. 17a-b). In the presence of CHX new protein synthesis is inhibited, thus HIF-1α levels would predominantly reflect the degradation process of HIF-1α protein. PC-3-Neo and PC-3-MSF-A cells were exposed to CHX for various incubation periods (between 0-45 minutes) and HIF-1α protein levels were analyzed by Western blot analysis and normalized to those of α-tubulin. Within 20 minutes of exposure to CHX, HIF-1α protein levels from PC-3-Neo cells were decreased to about 50% (FIGS. 16a-c). Although the intensity of the HIF-1α signal is different at the zero time-point, the degradation rate of HIF-1α protein was faster in PC-3-Neo than in PC-3-MSF-A cells (FIGS. 16a-c). This was further confirmed when cells were labeled with $^{35}$S-methionine and pulse-chased, after which HIF-1α protein levels were analyzed. The half-life of HIF-1α protein from PC-3-Neo cells was around 25 minutes compared to 45 minutes in PC-3-MSF-A cells (FIGS. 17a-b). As is further shown by the slope of the two curves, the rates of HIF-1α protein loss were slower in PC-3-MSF-A cells than in PC-3-Neo cells (FIG. 17b).

The pattern of HIF-1α immunoreactive bands in different MSF-A stable clones was examined under hypoxia (where degradation does not take place). As is shown in FIGS. 18a-b, the various clones exhibited differences in the higher molecular weight bands of HIF-1α protein which likely reflect ubiquitinated- and polyubiquitinated-HIF-1α (Ub-HIF-1α) species. The pattern of HIF-1α ubiquitination was inversely correlated with the levels of MSF-A protein expression (FIG. 18b). These results demonstrate that over-expression of MSF-A reduced HIF-1α ubiquitination species (i.e., the rate of degradation). These results suggest that the increase transcriptional activity of HIF-1α which was induced by over-expression of MSF-A is likely to be a result of stabilization of the HIF-1α protein by the MSF-A protein.

To study the ubiquitination of the endogenous HIF-1α in cells over-expressing MSF-A protein, the proteasome inhibitor MG-132 was used. Under these conditions HIF-1α is subjected to ubiquitination but can not be degraded through the proteasome. As is shown in FIGS. 19a-b, increasing doses of MG-132 induced the expression of HIF-1α and Ub-HIF-1α in PC-3-Neo cells. On the other hand, the pattern of Ub-HIF-1α levels in PC-3-MSF-A cells was less intense and exhibited lower molecular weight species (FIG. 19a). To confirm the ubiquitination forms of HIF-1α, PC-3-Neo and PC-3-MSF-A were treated with MG-132 and subjected to IP with HIF-1α antibody. Immunoprecipitates were immunoblotted in parallel with either HIF-1α (FIG. 20a) or ubiquitin (FIG. 20b) antibodies. Again, the levels of Ub-HIF-1α protein were lower in PC-3-MSF-A cells than in PC-3-Neo cells (FIG. 20a).

Altogether, these results demonstrate that the activation of HIF-1 by MSF-A is mediated through HIF-1α protein stabilization. MSF-A protein interacts with HIF-1α protein under normoxic conditions to modulate its ubiquitination and thus escaping proteasomal degradation.

Example 6

Preparation and Characterization of MSF-A Antibodies

To further understand MSF-A role in the MSF-A-HIF-1α complex, MSF-A specific antibodies were generated and employed in Western Blot and fluorescence immunohistochemistry, as follows.

Experimental Results

Characterization of an MSF-A antibody—Following immunization with the N-terminal MSF-A peptide, sera was drawn from the immunized rabbits and was tested on whole cell extracts prepared from PC-3 cells which were stably transfected with either the expression vector alone or the MSF-A vector (p3xFLAG-MSF-A). As is shown in FIGS. 10a-c, while the anti-Flag antibody recognized the typical 70-kDa band only in MSF-A transfected cells (FIG. 21a), the immune serum recognized a 70 kDa band in cells transfected with the expression vector alone or in cells transfected with the MSF-A expression vector (FIG. 21c). In addition, as is further shown in FIG. 21c, the immune serum recognized a slightly higher molecular weight band in MSF-A transfected cells, but not in cells transfected with the expression vector alone. The higher molecular weight band represents the Flag-tagged MSF-A in MSF-A transfected cells. Noteworthy, the preimmune serum which was diluted to the same extent (i.e., 1:500), revealed no binding signal (FIG. 21b).

Confirmation of MSF-A antibody specificity—To further characterize the new anti-MSF-A antibody (i.e., the immune serum), anti-Flag immunoprecipitates, which were prepared from cells transfected with the p3xFLAG-MSF-A vector, were subjected to immunoblotting using the new anti-MSF-A antibody. The immune serum (i.e., the new anti-MSF-A antibody) was capable of recognizing the typically immunoprecipitated Flag-MSF-A protein (FIGS. 22a-d). Flag-MSF-A was not recognized by other antibodies tested (data not shown).

Thus, these results demonstrate the generation of a new anti-MSF-A antibody, which is capable of specifically interacting with the 70-kDa MSF-A protein using Western Blot.

Example 7

MSF-A and HIF-1 Alpha Co-Localize at the Cell Nuclei

To determine the localization of MSF-A, biochemical fractionation and laser scanning confocal microscopy (LSCM) were employed, as follows.

Experimental Results

MSF-A is expressed in the nuclear fraction of a variety of cancerous cell lines—To identify the cellular localization of MSF-A, cytosolic and nuclear extracts were prepared from CL-1 and PC-3 cells which were grown under normoxia or hypoxia for overnight. The nuclear and cytosolic fractions of the cells were subjected to Western Blot analysis using the anti-HIF-1α antibody following by the anti-MSF-A antibody (i.e., the immune serum). As is shown in FIG. 23a, in both CL-1 and PC-3 cells upon hypoxic exposure HIF-1α protein was localized and accumulated in the nuclear fraction. On the other hand, MSF-A was more predominantly localized in the nuclear fraction without any significant change in its levels after hypoxia (FIG. 23b). A slight increase in the expression level of MSF-A protein was noted following hypoxia (FIG. 23b). On the other hand, there was no significant difference in the expression level of α-tubulin between the nuclear and cytosolic fractions (FIG. 23c).

To further confirm the nuclear localization of MSF-A, PC3 cells were grown under normoxia or hypoxia for 24 hours, following which they were subjected to MSF-A immunohistochemistry and laser scanning confocal microscopy (LSCM). As is shown in FIGS. 24a-d, the MSF-A staining was predominantly in the nucleus. Further confirmation of the nuclear localization of MSF-A was obtained using anti-MSF-A/anti-HIF-1α double immunohistochemistry. As is shown in FIGS. 25a-f, MSF-A and HIF-1α co-localize to the cell nucleus. HIF-1α was barely detectable under normoxic conditions but accumulated in the nucleus after exposure to hypoxia (FIGS. 25a-b, green staining) while MSF-A was detected in the nucleus under both conditions, normoxia and hypoxia (FIGS. 25c-d, red staining). Overlay of both staining showed co-localization of HIF-1α with MSF-A in the nucleus (FIGS. 25e-f). Nuclear localization of MSF-A was further confirmed by double-labeling with DAPI (data not shown). The results are consistent with the predicted sequence analysis of MSF-A protein that contains a bipartite nuclear targeting sequence at amino acids 2-18 as set forth in SEQ ID NO:3.

Thus, these results demonstrate that MSF-A is a nuclear protein which associates and co-localizes with HIF-1α.

Evidence for HIF-1α/MSF-A interaction in vivo—To further confirm that the association of MSF-A with HIF-1α also occurs in vivo, prostate cancer PC-3 and CL-1 cells, which express substantial levels of the HIF-1α protein under normoxic conditions were used in an IP-IB experiment. PC-3 or CL-1 cells were grown under normoxia or hypoxia and whole cell extracts were then subjected to co-immunoprecipitation using the anti-HIF-1α antibody. The immunoprecipitates were then subjected to Western Blot analysis using either the anti-HIF-1α or the anti-MSF-A antibody. As is shown in FIGS. 26a-c, under normoxic conditions, the anti-HIF-1α antibody was capable of immunoprecipitating both HIF-1α and MSF-A proteins. Under hypoxia, although there was a higher amount of HIF-1α protein within the immunoprecipitate its interaction with MSF-A protein was much weaker as demonstrated in two different cell lines. Thus, under hypoxic conditions, MSF-A dissociates from HIF-1α. These results are in good agreement with the results observed with 293 transfected cells (see FIGS. 3a-f for comparison). FIG. 27 depicts one suggested model for MSF-A and HIF-1α interaction under normoxia and hypoxia.

Altogether, these results demonstrate that while under normoxia conditions MSF-A associates with HIF-1α, and under hypoxia conditions MSF-A dissociates from HIF-1α. Thus, the interaction between endogenous HIF-1α and MSF-A protein is $O_2$-dependent.

Example 8

The Effects of MSF-A on HIF-1, Tumor Growth and Angiogenesis In Vivo

The effects of MSF-A on HIF-1, tumor growth and angiogenesis in vivo. To examine the effect of MSF-A on tumor growth, subcutaneous xenograft mouse tumor models were induced by the PC-3-MSF-A and PC-3-Neo cells.

Experimental Results

In this xenograft model, tumors derived from PC-3-MSF-A cells appeared earlier and exhibited increased mean volume (about 2-fold) compared to tumors derived from PC-3-Neo cells (FIG. 28). Although the difference in tumor volume was not statistically significant, the mean weight of PC-3-MSF-A tumors was significantly heavier than the wild-type tumors (FIG. 29). Most importantly, the phenotype of the tumors was strikingly different. Macroscopic and histological examination showed that PC-3-MSF-A tumors were more pleomorphic, aggressive and invasive, and there were only scattered small areas of necrosis, whereas a large area of central necrosis was observed in PC-3-Neo cell derived xenografts (not shown). It was also found that MSF-A overexpression significantly increased intratumoral cell proliferation and vascular density (FIGS. 30a-h). RT-PCR analysis of RNA derived from the tumors showed that the expression level of selected HIF-target genes, including VEGF and CA-IX, were elevated in PC-3-MSF-A tumors compared to PC-3-Neo tumors (FIGS. 31a-f). As a control, it is shown that PC-3-MSF-A tumor cells still express higher levels of MSF-A mRNA (FIG. 31a). Collectively, the in vitro and in vivo data indicate that MSF-A affects HIF-1 transcriptional activation, cell proliferation and tumor angiogenesis.

Example 9

MSF-A Expression in Common Human Tumors

Since under normal oxygen conditions HIF is induced by a number of oncogenes (e.g., AKT, Src, Ras), and since MSF-A was found to upregulate HIF-1α expression in vitro, the present inventor has hypothesized that MSF-A is involved in HIF-1α expression in cancerous cells. To investigate whether MSF-A is expressed in cancerous cells, whole cells extracts prepared from various cancerous cell lines were subjected to Western Blot using the new anti-MSF-A antibody (i.e., the immune serum).

Experimental Results

To examine the expression level of MSF-A in common human cancers, an expression array with matched tumor/normal cDNAs from 68 tumors and corresponding normal tissues from individual patients was employed. The array was hybridized with a probe (SEQ ID NO:4214) which reacts with all variants of SEPT9 including MSF-A. For normalization, the array was re-probed with a β-actin control probe (Ambion, Austin, Tx, USA), quantified and analyzed for comparison between normal versus tumor expression profile. As shown in FIG. 32a, strikingly SEPT9 gene was significantly over-expressed in ovarian tumor samples compared to other samples tested. Interestingly, a lesser degree of SEPT9 over-expression was observed among samples of other female reproductive system including breast and uterus (FIG. 32a). On the other hand, there was almost no change noticed in expression level samples from renal, prostate or gastrointestinal tract tumors (FIG. 32a).

To specifically follow the expression level of MSF-A, the RT-PCR analysis was extended in prostate cancer where it was originally found to interact with HIF-1α. RNA samples from various prostate cell lines and xenografts exhibited higher expression level of MSF-A mRNA in prostate cancer samples compared to those of RNA derived from normal prostate tissue (FIGS. 32b-d).

Analysis and Discussion

In the present study, a novel regulatory pathway was identified in which MSF-A, a member of the mammalian septin gene family affects tumorigenesis through, at least in part, the activation of the HIF-dependent response system. These results show that MSF-A protein directly interacts with HIF-1α but not with HIF-1β. Overexpression of MSF-A leads to activation of HIF-1 and upregulation HIF-downstream genes, in vitro and in vivo. Most importantly, the findings of the present study demonstrate that MSF-A promotes proliferation, tumor growth and vascularization.

HIF-1 is a master regulator of the hypoxic response pathway not only in physiological processes but also in pathophysiological states such as ischemia and cancer (Maxwell and Ratcliffe, 2002; Semenza, 2003; Wenger, 2002). Apart from the relatively well-characterized mechanisms of hypoxic HIF-1α subunit stabilization, many growth factors and cytokines are known to stabilize HIF-1α under normoxic conditions. Despite this great diversity, most of these growth factors might stabilize HIF-1α via common cellular kinase pathways including PI-3K and MAPK pathways, activated by cell type-specific receptors (Wenger, 2002). However, so far it is not completely understood how HIF-1α is stabilized in cancer cells under "normoxic" conditions. The importance and potential therapeutic benefits of the HIF pathway have driven the search for new regulatory components. To that end, new candidates which affect the HIF pathway were searched for. Co-immunoprecipitation experiments revealed an interaction between MSF-A and HIF-1α. MSF-A is a splice variant of the SEPT9 of the mammalian septin gene family (Macara et al., 2002) and was first found as a fusion partner gene of MLL in a case of therapy-related acute myeloid leukemia with a t(11,17)(q23;q25) translocation (Osaka et al., 1999; Taki, Ohnishi, Shinohara, Sako, Bessho, Yanagisawa and Hayashi, 1999). Septins were originally discovered in yeast and found to be involved in diverse cellular processes, including cytokinesis, vesicle trafficking, apoptosis and maintenance of cell polarity (Hall and Russell, 2004). The family of human septins shows considerable homology in the core GTP-binding domain, but divergence in the N and C terminals (Hall and Russell, 2004; Kartmann and Roth, 2001). While most of the available data on the biology of septins are derived from yeast, little is known on the physiological and the pathophysiological significance of septins in mammals. A number of evidences suggest a role of septins in oncogenesis. Some of septin genes (SEPT5, 6, 9 & 11) are involved in chromosomal translocations in myeloid leukemias with the formation of chimeric MLL fusion proteins (Hall and Russell, 2004). Second, it was found recently that SEPT9 is altered in ovarian cancer (Burrows, Chanduloy, McIlhatton, Nagar, Yeates, Donaghy, Price, Godwin, Johnston and Russell, 2003) consistent with the results of the present study and that SEPT9 is amplified and over-expressed in breast cancer (Montagna, Lyu, Hunter, Lukes, Lowther, Reppert, Hissong, Weaver and Ried, 2003). Very recently, Scott et al. has reported a meticulous analysis of SEPT9 expression in a wide range of human tumors (Scott et al., 2005). SEPT9 was found to be over-expressed in breast, CNS, endometrium, kidney, liver, lung, lymphoid, esophagus, ovary, pancreas, skin, soft tissue and thyroid (Scott et al., 2005). In this study MSF-A was found to be specifically upregulated in prostate cancer cell lines and xenografts. Interestingly, HIF-1α overexpression is also observed in the majority of human cancers (Zhong, De Marzo, Laughner, Lim, Hilton, Zagzag, Buechler, Isaacs, Semenza and Simons, 1999). Since in most cancers the mechanisms of how HIF-1α is over-expressed are yet not known while VHL is not mutated, these data support the hypothesis that the interaction between these two cellular processes may have a role in tumor progression in certain cancers.

MSF-A expression augments the activity of HIF-1 and induces higher proliferation rates both, under normoxia and hypoxia as well as in vitro and in vivo. Furthermore, MSF-A affects the pattern of tumor necrosis with overall increased vascularity within tumors. This is the first observation that a septin protein has effects on tumor angiogenesis.

A number of septins have been shown to bind and hydrolyze guanine nucleotide. However, the role of GTP binding and hydrolysis in septin function has not been fully elucidated (Field, al-Awar, Rosenblatt, Wong, Alberts and Mitchison, 1996; Gladfelter, Bose, Zyla, Bardes and Lew, 2002; Mendoza, Hyman and Glotzer, 2002; Robertson, Church, Nagar, Price, Hall and Russell, 2004; Versele and Thorner, 2004). Deletion of the GTP binding domain in MSF-A, led to no change in HIF-1 activity. There was neither activation nor inhibition of HIF-1 function while the mutant lacking the GTP binding site still has the ability to interact with HIF-1α protein. On the other hand, deletion of the most variable N-terminal domain of MSF-A exhibited dominant negative effect on HIF transcriptional activity and still has been bound to HIF-1α. These results indicate that binding of MSF-A to HIF-1α is not sufficient to activate the HIF complex but requires binding and/or hydrolysis of GTP upon MSF-A as well as intact N-terminal. It was shown previously that Rac1 of the small GTPase Rho family is activated in response to hypoxia and is required for the induction of HIF-1α protein expression and transcriptional activity in hypoxic cells (Hirota and Semenza, 2001). Very recently, Nagata and Inagaki have identified a Rho-guanine nucleotide exchange factor (GEF) as a binding partner for MSF-A, describing the first link between septins and Rho signaling (Nagata and Inagaki, 2005). It is reasonable to speculate that the activation of HIF-1 by Rho could be mediated through interactions involving MSF-A.

Mechanistically, these data show that MSF-A affects HIF-1α protein at the posttranslational level through stabilizing the protein and preventing its ubiquitination. Although the interaction between HIF-1α and MSF-A was predominantly under normoxia, the hypoxic induction of HIF-1 was also increased with overexpression of MSF-A. It is not clear yet whether MSF-A inhibits HIF-1α ubiquitination by preventing its proline hydroxylation or by modulating VHL E3-ligase activity. Further studies are necessary to elucidate the exact mechanism by which MSF-A stabilizes HIF-1α.

The interactions between HIF-1α and MSF-A, in addition to their colocalization, and the functional activation of HIF-1 by MSF-A may represent the role of SEPT9 function in tumorigenesis.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

References

Additional References are Cited in Text

Bardos, J. I., and Ashcroft, M. (2004). Hypoxia-inducible factor-1 and oncogenic signalling. Bioessays 26, 262-269.

Brahimi-Horn, M. C., and Pouyssegur, J. (2005). The hypoxia-inducible factor and tumor progression along the angiogenic pathway. Int Rev Cytol 242, 157-213.

Bruick, R. K., and McKnight, S. L. (2001). A conserved family of prolyl-4-hydroxylases that modify HIF. Science 294, 1337-1340.

Burrows, J. F., Chanduloy, S., McIlhatton, M. A., Nagar, H., Yeates, K., Donaghy, P., Price, J., Godwin, A. K., Johnston, P. G., and Russell, S. E. (2003). Altered expression of the septin gene, SEPT9, in ovarian neoplasia. J Pathol 201, 581-588.

Carmeliet, P., Dor, Y., Herbert, J. M., Fukumura, D., Brusselmans, K., Dewerchin, M., Neeman, M., Bono, F., Abramovitch, R., Maxwell, P., et al. (1998). Role of HIF-1alpha in hypoxia-mediated apoptosis, cell proliferation and tumour angiogenesis. Nature 394, 485-490.

Epstein, A. C., Gleadle, J. M., McNeill, L. A., Hewitson, K. S., O'Rourke, J., Mole, D. R., Mukherji, M., Metzen, E., Wilson, M. I., Dhanda, A., et al. (2001). C. elegans EGL-9 and mammalian homologs define a family of dioxygenases that regulate HIF by prolyl hydroxylation. Cell 107, 43-54.

Field, C. M., al-Awar, O., Rosenblatt, J., Wong, M. L., Alberts, B., and Mitchison, T. J. (1996). A purified *Drosophila* septin complex forms filaments and exhibits GTPase activity. J Cell Biol 133, 605-616.

Gladfelter, A. S., Bose, I., Zyla, T. R., Bardes, E. S., and Lew, D. J. (2002). Septin ring assembly involves cycles of GTP loading and hydrolysis by Cdc42p. J Cell Biol 156, 315-326.

Hall, P. A., Jung, K., Hillan, K. J., and Russell, S. H. (2005). Expression profiling the human septin gene family. J Pathol 206, 269-278.

Hall, P. A., and Russell, S. E. (2004). The pathobiology of the septin gene family. J Pathol 204, 489-505.

Hewitson, K. S., McNeill, L. A., Riordan, M. V., Tian, Y. M., Bullock, A. N., Welford, R. W., Elkins, J. M., Oldham, N. J., Bhattacharya, S., Gleadle, J. M., et al. (2002). Hypoxia-inducible factor (HIF) asparagine hydroxylase is identical to factor inhibiting HIF (FIH) and is related to the cupin structural family. J Biol Chem 277, 26351-26355.

Hirota, K., and Semenza, G. L. (2001). Rac1 activity is required for the activation of hypoxia-inducible factor 1. J Biol Chem 276, 21166-21172.

Hopfl, G., Ogunshola, O., and Gassmann, M. (2004). HIFs and tumors—causes and consequences. Am J Physiol Regul Integr Comp Physiol 286, R608-623.

Ivan, M., Kondo, K., Yang, H., Kim, W., Valiando, J., Ohh, M., Salic, A., Asara, J. M., Lane, W. S., and Kaelin, W. G., Jr. (2001). HIFalpha targeted for VHL-mediated destruction by proline hydroxylation: implications for $O_2$ sensing. Science 292, 464-468.

Jeong, J. W., Bae, M. K., Ahn, M. Y., Kim, S. H., Sohn, T. K., Bae, M. H., Yoo, M. A., Song, E. J., Lee, K. J., and Kim, K. W. (2002). Regulation and destabilization of HIF-1alpha by ARD1-mediated acetylation. Cell 111, 709-720.

Kartmann, B., and Roth, D. (2001). Novel roles for mammalian septins: from vesicle trafficking to oncogenesis. J Cell Sci 114, 839-844.

Kim, W., and Kaelin, W. G., Jr. (2003). The von Hippel-Lindau tumor suppressor protein: new insights into oxygen sensing and cancer. Curr Opin Genet Dev 13, 55-60.

Lando, D., Peet, D. J., Gorman, J. J., Whelan, D. A., Whitelaw, M. L., and Bruick, R. K. (2002). FIH-1 is an asparaginyl hydroxylase enzyme that regulates the transcriptional activity of hypoxia-inducible factor. Genes Dev 16, 1466-1471.

Mabjeesh, N. J., Post, D. E., Willard, M. T., Kaur, B., Van Meir, E. G., Simons, J. W., and Zhong, H. (2002). Geldanamycin induces degradation of hypoxia-inducible factor 1alpha protein via the proteosome pathway in prostate cancer cells. Cancer Res 62, 2478-2482.

Macara, I. G., Baldarelli, R., Field, C. M., Glotzer, M., Hayashi, Y., Hsu, S. C., Kennedy, M. B., Kinoshita, M., Longtine, M., Low, C., et al. (2002). Mammalian septins nomenclature. Mol Biol Cell 13, 4111-4113.

Mahon, P. C., Hirota, K., and Semenza, G. L. (2001). FIH-1: a novel protein that interacts with HIF-1alpha and VHL to mediate repression of HIF-1 transcriptional activity. Genes Dev 15, 2675-2686.

Maxwell, P. H., Dachs, G. U., Gleadle, J. M., Nicholls, L. G., Harris, A. L., Stratford, I. J., Hankinson, O., Pugh, C. W., and Ratcliffe, P. J. (1997). Hypoxia-inducible factor-1 modulates gene expression in solid tumors and influences both angiogenesis and tumor growth. Proc Natl Acad Sci USA 94, 8104-8109.

Maxwell, P. H., and Ratcliffe, P. J. (2002). Oxygen sensors and angiogenesis. Semin Cell Dev Biol 13, 29-37.

Melillo, G. (2004). HIF-1: a target for cancer, ischemia and inflammation—too good to be true? Cell Cycle 3, 154-155.

Mendoza, M., Hyman, A. A., and Glotzer, M. (2002). GTP binding induces filament assembly of a recombinant septin. Curr Biol 12, 1858-1863.

Metzen, E., Berchner-Pfannschmidt, U., Stengel, P., Marxsen, J. H., Stolze, I., Klinger, M., Huang, W. Q., Wotzlaw, C., Hellwig-Burgel, T., Jelkmann, W., et al. (2003). Intracellular localisation of human HIF-1 alpha hydroxylases: implications for oxygen sensing. J Cell Sci 116, 1319-1326.

Montagna, C., Lyu, M. S., Hunter, K., Lukes, L., Lowther, W., Reppert, T., Hissong, B., Weaver, Z., and Ried, T. (2003). The Septin 9 (MSF) gene is amplified and overexpressed in mouse mammary gland adenocarcinomas and human breast cancer cell lines. Cancer Res 63, 2179-2187.

Nagata, K., and Inagaki, M. (2005). Cytoskeletal modification of Rho guanine nucleotide exchange factor activity: identification of a Rho guanine nucleotide exchange factor as a binding partner for Sept9b, a mammalian septin. Oncogene 24, 65-76.

Osaka, M., Rowley, J. D., and Zeleznik-Le, N. J. (1999). MSF (MLL septin-like fusion), a fusion partner gene of MLL, in a therapy-related acute myeloid leukemia with a t(11;17)(q23;q25). Proc Natl Acad Sci USA 96, 6428-6433.

Post, D. E., and Van Meir, E. G. (2001). Generation of bidirectional hypoxia/HIF-responsive expression vectors to target gene expression to hypoxic cells. Gene Ther 8, 1801-1807.

Quintero, M., Mackenzie, N., and Brennan, P. A. (2004). Hypoxia-inducible factor 1 (HIF-1) in cancer. Eur J Surg Oncol 30, 465-468.

Robertson, C., Church, S. W., Nagar, H. A., Price, J., Hall, P. A., and Russell, S. E. (2004). Properties of SEPT9 isoforms and the requirement for GTP binding. J Pathol 203, 519-527.

Ryan, H. E., Lo, J., and Johnson, R. S. (1998). HIF-1 alpha is required for solid tumor formation and embryonic vascularization. Embo J 17, 3005-3015.

Ryan, H. E., Poloni, M., McNulty, W., Elson, D., Gassmann, M., Arbeit, J. M., and Johnson, R. S. (2000). Hypoxia-inducible factor-1alpha is a positive factor in solid tumor growth. Cancer Res 60, 4010-4015.

Scott, M., Hyland, P. L., McGregor, G., Hillan, K. J., Russell, S. E., and Hall, P. A. (2005). Multimodality expression profiling shows SEPT9 to be overexpressed in a wide range of human tumours. Oncogene.

Semenza, G. L. (2003). Targeting HIF-1 for cancer therapy. Nat Rev Cancer 3, 721-732.

Semenza, G. L. (2004). Hydroxylation of HIF-1: oxygen sensing at the molecular level. Physiology (Bethesda) 19, 176-182.

Taki, T., Ohnishi, H., Shinohara, K., Sako, M., Bessho, F., Yanagisawa, M., and Hayashi, Y. (1999). AF17q25, a putative septin family gene, fuses the MLL gene in acute myeloid leukemia with t(11;17)(q23;q25). Cancer Res 59, 4261-4265.

Vaupel, P. (2004). The role of hypoxia-induced factors in tumor progression. Oncologist 9 Suppl 5, 10-17.

Versele, M., and Thorner, J. (2004). Septin collar formation in budding yeast requires GTP binding and direct phosphorylation by the PAK, Cla4. J Cell Biol 164, 701-715.

Welsh, S. J., and Powis, G. (2003). Hypoxia inducible factor as a cancer drug target. Curr Cancer Drug Targets 3, 391-405.

Wenger, R. H. (2002). Cellular adaptation to hypoxia: O2-sensing protein hydroxylases, hypoxia-inducible transcription factors, and O2-regulated gene expression. Faseb J 16, 1151-1162.

Zhong, H., Agani, F., Baccala, A. A., Laughner, E., Rioseco-Camacho, N., Isaacs, W. B., Simons, J. W., and Semenza, G. L. (1998). Increased expression of hypoxia inducible factor-1alpha in rat and human prostate cancer. Cancer Res 58, 5280-5284.

Zhong, H., De Marzo, A. M., Laughner, E., Lim, M., Hilton, D. A., Zagzag, D., Buechler, P., Isaacs, W. B., Semenza, G. L., and Simons, J. W. (1999). Overexpression of hypoxia-inducible factor 1alpha in common human cancers and their metastases. Cancer Res 59, 5830-5835.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08785373B2). An electronic copy of the "Sequence Listing" will also be available from the USPTO upon request and payment of the fee set forth in 37 CFR 1.19(b)(3).

What is claimed is:

1. A method of treating prostate cancer and/or inhibiting a growth of a prostate cancerous tumor and/or prostate cancerous metastases in an individual in need thereof comprising providing to the individual an MSF-A derived peptide or peptide analogue, of up to 30 amino acid resides in length, which includes the amino acid sequence set forth in SEQ ID NO: 4213, thereby treating the prostate cancer and/or inhibiting the growth of the prostate cancerous tumor and/or the prostate cancerous metastases in the individual.

2. The method of claim 1, wherein said MSF-A derived peptide or peptide analogue further comprises a modification of said peptide or peptide analogue for increasing penetration into cells or increasing stability while in a body.

3. The method of claim 2, wherein said modification comprises an N terminus modification, a C terminus modification, a peptide bond modification, a backbone modification or a residue modification.

* * * * *